US012704459B2

(12) United States Patent
Kenten et al.

(10) Patent No.: US 12,704,459 B2
(45) Date of Patent: Aug. 11, 2026

(54) METHODS, COMPOSITIONS, AND KITS FOR ASSAY SIGNAL AMPLIFICATION

(71) Applicant: MESO SCALE TECHNOLOGIES, LLC., Rockville, MD (US)

(72) Inventors: John Kenten, Boyds, MD (US); George Sigal, Rockville, MD (US); Alexander K. Tucker-Schwartz, Bethesda, MD (US)

(73) Assignee: MESO SCALE TECHNOLOGIES, LLC., Rockville, MD (US)

( * ) Notice: Subject to any disclaimer, the term of this patent is extended or adjusted under 35 U.S.C. 154(b) by 966 days.

(21) Appl. No.: 17/849,917

(22) Filed: Jun. 27, 2022

(65) Prior Publication Data

US 2023/0020070 A1 Jan. 19, 2023

Related U.S. Application Data

(60) Provisional application No. 63/215,660, filed on Jun. 28, 2021.

(51) Int. Cl.
*C12Q 1/6816* (2018.01)
*C07F 15/00* (2006.01)
*G01N 21/64* (2006.01)
*G01N 21/66* (2006.01)
*G01N 33/533* (2006.01)
*G01N 33/58* (2006.01)

(52) U.S. Cl.
CPC ..... *G01N 21/6428* (2013.01); *C07F 15/0053* (2013.01); *C12Q 1/6816* (2013.01); *G01N 21/66* (2013.01); *G01N 33/533* (2013.01); *G01N 33/582* (2013.01); *G01N 2021/6439* (2013.01)

(58) Field of Classification Search
None
See application file for complete search history.

(56) References Cited

U.S. PATENT DOCUMENTS 3,996,345 A 12/1976 Ullman et al.
4,235,601 A 11/1980 Deutsch et al.
4,342,566 A 8/1982 Theofilopoulos et al.
4,442,204 A 4/1984 Greenquist et al.
4,595,661 A 6/1986 Cragle et al.
4,988,617 A 1/1991 Landegren et al.
(Continued)

FOREIGN PATENT DOCUMENTS

CN 1446050 A 10/2003
CN 101198707 A 6/2008
(Continued)

OTHER PUBLICATIONS

Buijs et al., "Interference by antiruthenium antibodies in the Roche thyroid-stimulating hormone assay," Ann Clin Biochem 48(3):276-281 (2011).

(Continued)

*Primary Examiner* — Joseph G. Dauner
(74) *Attorney, Agent, or Firm* — MEDLER FERRO WOODHOUSE & MILLS PLLC

(57) ABSTRACT

The invention relates to methods, compositions, kits, and assay systems for assay signal amplification. Also provided herein is a signal amplification reagent, wherein the signal amplification reagent is an antibody or antigen-binding fragment thereof.

24 Claims, 37 Drawing Sheets

(56) References Cited

U.S. PATENT DOCUMENTS 5,026,653 A 6/1991 Lee et al.
5,028,535 A 7/1991 Buechler et al.
5,093,268 A 3/1992 Leventis et al.
5,147,806 A 9/1992 Kamin et al.
5,185,243 A 2/1993 Ullman et al.
5,200,314 A 4/1993 Urdea
5,238,808 A 8/1993 Bard et al.
5,240,863 A 8/1993 Shibue et al.
5,308,754 A 5/1994 Kankare et al.
5,324,457 A 6/1994 Zhang et al.
5,561,043 A 10/1996 Cantor et al.
5,589,136 A 12/1996 Northrup et al.
5,591,581 A 1/1997 Massey et al.
5,597,910 A 1/1997 Gudibande et al.
5,620,851 A 4/1997 Axelrod et al.
5,629,156 A 5/1997 Shah et al.
5,629,157 A 5/1997 Goodman
5,635,347 A 6/1997 Link et al.
5,641,623 A 6/1997 Martin
5,643,713 A 7/1997 Liang et al.
5,652,107 A 7/1997 Lizardi et al.
5,656,731 A 8/1997 Urdea
5,660,991 A 8/1997 Lakowicz et al.
5,665,539 A 9/1997 Sano et al.
5,667,974 A 9/1997 Birkenmeyer et al.
5,679,519 A 10/1997 Oprandy
5,705,402 A 1/1998 Leland et al.
5,714,089 A 2/1998 Bard et al.
5,714,320 A 2/1998 Kool
5,731,147 A 3/1998 Bard et al.
5,759,773 A 6/1998 Tyagi et al.
5,776,672 A 7/1998 Hashimoto et al.
5,786,141 A 7/1998 Bard et al.
5,837,446 A 11/1998 Cozzette et al.
5,846,485 A 12/1998 Leland et al.
5,854,033 A 12/1998 Lizardi
5,866,434 A 2/1999 Massey et al.
5,871,921 A 2/1999 Landegren et al.
5,925,517 A 7/1999 Tyagi et al.
5,942,391 A 8/1999 Zhang et al.
6,048,687 A 4/2000 Kenten et al.
6,054,274 A 4/2000 Sampson et al.
6,066,448 A 5/2000 Wohlstadter et al.
6,077,668 A 6/2000 Kool
6,136,268 A 10/2000 Ala-Kleme
6,140,135 A 10/2000 Landegren et al.
6,143,495 A 11/2000 Lizardi et al.
6,183,960 B1 2/2001 Lizardi
6,207,369 B1 3/2001 Wohlstadter et al.
6,210,884 B1 4/2001 Lizardi
6,214,552 B1 4/2001 Heroux et al.
6,235,472 B1 5/2001 Landegren et al.
6,287,824 B1 9/2001 Lizardi
6,291,187 B1 9/2001 Kingsmore et al.
6,316,229 B1 11/2001 Lizardi et al.
6,316,607 B1 11/2001 Massey et al.
6,323,009 B1 11/2001 Lasken et al.
6,329,150 B1 12/2001 Lizardi et al.
6,344,329 B1 2/2002 Lizardi
6,368,801 B1 4/2002 Faruqi
6,444,661 B1 9/2002 Barton et al.
6,468,741 B1 10/2002 Massey et al.
6,479,233 B1 11/2002 Bard et al.
6,511,809 B2 1/2003 Baez et al.
6,531,283 B1 3/2003 Kingsmore et al.
6,558,928 B1 5/2003 Landegren
6,569,647 B1 5/2003 Zhang et al.
6,632,609 B2 10/2003 Lizardi
6,646,118 B2 11/2003 Kwiatkowski et al.
6,673,533 B1 1/2004 Wohlstadter et al.
RE38,442 E 2/2004 Zhang et al.
6,709,815 B1 3/2004 Dong et al.
6,797,474 B2 9/2004 Lizardi
6,808,939 B2 10/2004 Sigal et al.
6,878,515 B1 4/2005 Landegren
6,939,720 B2 9/2005 Chandler et al.
6,977,722 B2 12/2005 Wohlstadter et al.
7,074,564 B2 7/2006 Landegren et al.
7,192,703 B2 3/2007 Sun et al.
7,306,904 B2 12/2007 Landegren et al.
7,314,711 B2 1/2008 Richter et al.
7,320,860 B2 1/2008 Landegren et al.
7,351,528 B2 4/2008 Landegren
7,618,776 B2 11/2009 Lizardi
7,790,388 B2 9/2010 Landegren et al.
7,807,448 B2 10/2010 Glezer et al.
7,842,246 B2 11/2010 Wohlstadter et al.
7,883,848 B2 2/2011 Ericsson
7,883,849 B1 2/2011 Dahl
7,914,983 B2 3/2011 Palaniappan et al.
7,932,060 B2 4/2011 Nadeau et al.
8,013,134 B2 9/2011 Fredriksson
8,053,188 B2 11/2011 Gullberg et al.
8,080,393 B2 12/2011 Koch et al.
8,163,499 B2 4/2012 Singh et al.
8,222,047 B2 7/2012 Duffy et al.
8,236,574 B2 8/2012 Duffy et al.
8,268,554 B2 9/2012 Schallmeiner
8,338,776 B2 12/2012 Walt et al.
8,343,526 B2 1/2013 Billadeau et al.
8,741,559 B2 6/2014 Treiber et al.
8,770,471 B2 7/2014 Cong et al.
9,499,573 B2 11/2016 Bergmann et al.
9,618,510 B2 4/2017 Aghvanyan et al.
9,714,937 B2 7/2017 Dunaway et al.
9,731,297 B2 8/2017 Glezer et al.
9,777,338 B2 10/2017 Glezer et al.
9,921,166 B2 3/2018 Glezer et al.
9,976,177 B2 5/2018 Terbrueggen
10,114,015 B2 10/2018 Glezer et al.
10,184,884 B2 1/2019 Anderson et al.
10,189,023 B2 1/2019 Glezer et al.
10,201,812 B2 2/2019 Glezer et al.
10,272,436 B2 4/2019 Glezer et al.
10,281,678 B2 5/2019 Chamberlin et al.
10,408,823 B2 * 9/2019 Aghvanyan .......... C12Q 1/6844
10,908,157 B2 * 2/2021 Aghvanyan ........ G01N 33/5306
11,242,570 B2 2/2022 Glezer
11,525,825 B2 12/2022 Aghvanyan et al.
11,697,840 B2 * 7/2023 Glezer ................ C12Q 1/6837 435/6.1
12,359,264 B2 7/2025 Glezer et al.
12,411,131 B2 * 9/2025 Aghvanyan .......... C12Q 1/6832
12,553,887 B2 2/2026 Kenten et al.
2001/0041340 A1 * 11/2001 Kingsmore .......... C12Q 1/6804 435/6.12
2001/0053519 A1 12/2001 Fodor et al.
2002/0035247 A1 3/2002 Kwiatkowski et al.
2002/0051986 A1 5/2002 Baez et al.
2002/0064779 A1 5/2002 Landegren et al.
2002/0102592 A1 8/2002 Landegren
2002/0127658 A1 9/2002 Amouyal
2002/0155490 A1 10/2002 Skinner et al.
2003/0077670 A1 4/2003 Cheng et al.
2004/0022677 A1 2/2004 Wohlstadter et al.
2004/0023207 A1 2/2004 Polansky
2004/0023271 A1 2/2004 Kum et al.
2004/0121382 A1 6/2004 Liu et al.
2004/0142323 A1 7/2004 Boyde
2004/0189311 A1 9/2004 Glezer et al.
2004/0209261 A1 10/2004 Keys et al.
2004/0248103 A1 12/2004 Feaver et al.
2004/0265897 A1 12/2004 Lizardi
2005/0003432 A1 1/2005 Hall et al.
2005/0009015 A1 1/2005 Gregg et al.
2005/0009050 A1 1/2005 Nadeau
2005/0014140 A1 1/2005 Erikson et al.
2005/0052646 A1 3/2005 Wohlstadter et al.
2005/0142033 A1 6/2005 Glezer et al.
2005/0282158 A1 12/2005 Landegren
2005/0287526 A1 12/2005 Landegren et al.
2006/0078894 A1 4/2006 Winkler et al.
2007/0154899 A1 7/2007 Coull et al.
2007/0161029 A1 7/2007 Li et al.

(56) References Cited

U.S. PATENT DOCUMENTS

| | | | | |
|---|---|---|---|---|
| 2007/0259381 | A1 | 11/2007 | Rissin et al. | |
| 2007/0259385 | A1 | 11/2007 | Rissin et al. | |
| 2007/0259448 | A1 | 11/2007 | Rissin et al. | |
| 2008/0188638 | A1 | 8/2008 | Breitenkamp et al. | |
| 2009/0011943 | A1 | 1/2009 | Drmanac et al. | |
| 2009/0176318 | A1 | 7/2009 | Kolpashchikov | |
| 2009/0178934 | A1 | 7/2009 | Jarvius et al. | |
| 2009/0191553 | A1 | 7/2009 | Hendrickson | |
| 2009/0203155 | A1 | 8/2009 | Chiku | |
| 2010/0075862 | A1 | 3/2010 | Duffy et al. | |
| 2010/0129819 | A1 | 5/2010 | Hu et al. | |
| 2010/0261292 | A1 | 10/2010 | Glezer et al. | |
| 2011/0022331 | A1 | 1/2011 | Clinton et al. | |
| 2011/0027772 | A1 | 2/2011 | Ahn et al. | |
| 2011/0177054 | A1 | 7/2011 | Gibbings et al. | |
| 2011/0212537 | A1 | 9/2011 | Rissin et al. | |
| 2012/0196774 | A1 | 8/2012 | Fournier et al. | |
| 2012/0252692 | A1 | 10/2012 | Kutyavin | |
| 2012/0289428 | A1 | 11/2012 | Duffy et al. | |
| 2013/0059741 | A1 | 3/2013 | Weiner | |
| 2013/0171066 | A1 | 7/2013 | Sellegren et al. | |
| 2013/0323756 | A1 | 12/2013 | Tullis et al. | |
| 2014/0087379 | A1 | 3/2014 | Bashkirov et al. | |
| 2014/0194311 | A1 | 7/2014 | Gullberg | |
| 2014/0272939 | A1 | 9/2014 | Aghvanyan et al. | |
| 2014/0274775 | A1 | 9/2014 | Glezer et al. | |
| 2014/0315189 | A1 | 10/2014 | Glezer et al. | |
| 2015/0044674 | A1 | 2/2015 | Fredriksson et al. | |
| 2017/0089892 | A1 * | 3/2017 | Aghvanyan .......... | C12Q 1/6832 |
| 2017/0168047 | A1 | 6/2017 | Aghvanyan et al. | |
| 2017/0362668 | A1 | 12/2017 | Glezer et al. | |
| 2018/0074082 | A1 | 3/2018 | Glezer et al. | |
| 2019/0002971 | A1 | 1/2019 | Koslover et al. | |
| 2019/0011441 | A1 | 1/2019 | Glezer | |
| 2019/0391140 | A1 | 12/2019 | Aghvanyan et al. | |
| 2019/0391170 | A1 | 12/2019 | Kochar et al. | |
| 2021/0190778 | A1 | 6/2021 | Aghvanyan et al. | |
| 2022/0033918 | A1 | 2/2022 | Glezer | |
| 2022/0099661 | A1 | 3/2022 | Kenten et al. | |
| 2022/0357318 | A1 | 11/2022 | Aghvanyan et al. | |
| 2023/0175043 | A1 | 6/2023 | Kenten et al. | |
| 2023/0407380 | A1 | 12/2023 | Glezer et al. | |
| 2024/0229110 | A1 | 7/2024 | Kenten et al. | |
| 2024/0368676 | A1 | 11/2024 | Kenten et al. | |
| 2025/0060361 | A1 | 2/2025 | Aghvanyan et al. | |
| 2025/0327141 | A1 | 10/2025 | Glezer et al. | |
| 2025/0362291 | A1 | 11/2025 | Aghvanyan et al. | |

FOREIGN PATENT DOCUMENTS

| | | | |
|---|---|---|---|
| CN | 101988920 | A | 3/2011 |
| CN | 102317779 | A | 1/2012 |
| CN | 103703145 | B | 4/2014 |
| CN | 104114718 | A | 10/2014 |
| CN | 108374052 | A | 8/2018 |
| EP | 1985714 | A1 | 10/2008 |
| EP | 2500435 | A1 | 9/2012 |
| JP | H04-262799 | A | 9/1992 |
| JP | H08-505050 | A | 6/1996 |
| JP | H10-504105 | A | 4/1998 |
| JP | H11-508040 | A | 7/1999 |
| JP | 2000-300267 | A | 10/2000 |
| JP | 2005-521409 | A | 7/2005 |
| JP | 2005-522405 | A | 7/2005 |
| JP | 2006-511807 | A | 4/2006 |
| JP | 2007-525661 | A | 9/2007 |
| JP | 2009-106220 | A | 5/2009 |
| JP | 2009-222712 | A | 10/2009 |
| JP | 2020-529585 | A | 10/2020 |
| KR | 10-2013-0003127 | A | 1/2013 |
| WO | 90/05910 | A1 | 5/1990 |
| WO | 91/17442 | A1 | 11/1991 |
| WO | 94/14961 | A1 | 7/1994 |
| WO | 95/35390 | A1 | 12/1995 |
| WO | 96/35812 | A1 | 11/1996 |
| WO | 99/32662 | A1 | 7/1997 |
| WO | 97/36931 | A1 | 10/1997 |
| WO | 98/12539 | A1 | 3/1998 |
| WO | 98/57154 | A1 | 12/1998 |
| WO | 99/14599 | A1 | 3/1999 |
| WO | 99/49079 | A1 | 9/1999 |
| WO | 99/58962 | A1 | 11/1999 |
| WO | 99/63347 | A2 | 12/1999 |
| WO | 00/03233 | A1 | 1/2000 |
| WO | 00/04193 | A1 | 1/2000 |
| WO | 01/35100 | A2 | 5/2001 |
| WO | 01/38580 | A2 | 5/2001 |
| WO | 01/84146 | A2 | 11/2001 |
| WO | 03/022028 | A2 | 3/2003 |
| WO | 03/033722 | A2 | 4/2003 |
| WO | 2004/045543 | A2 | 6/2004 |
| WO | 2004/061131 | A1 | 7/2004 |
| WO | 2004/094456 | A2 | 11/2004 |
| WO | 2005/059509 | A2 | 6/2005 |
| WO | 2009/029073 | A1 | 3/2009 |
| WO | 2009/067009 | A1 | 5/2009 |
| WO | 2009/092386 | A2 | 7/2009 |
| WO | 2010/059820 | A1 | 5/2010 |
| WO | 2010/118411 | A2 | 10/2010 |
| WO | 2011/047087 | A2 | 4/2011 |
| WO | 2011/143583 | A1 | 11/2011 |
| WO | 2012/007511 | A1 | 2/2012 |
| WO | 2012/049316 | A1 | 4/2012 |
| WO | 2012/060083 | A1 | 5/2012 |
| WO | 2012/104261 | A1 | 8/2012 |
| WO | 2012/152942 | A1 | 11/2012 |
| WO | 2012/160083 | A1 | 11/2012 |
| WO | 2013/113699 | A1 | 8/2013 |
| WO | 2014/031984 | A1 | 2/2014 |
| WO | 2014/160192 | A1 | 10/2014 |
| WO | 2014/165061 | A1 | 10/2014 |
| WO | 2015/175856 | A1 | 11/2015 |
| WO | 2016/164477 | A1 | 10/2016 |
| WO | 2017/015636 | A1 | 1/2017 |
| WO | 2017/093271 | A1 | 6/2017 |
| WO | 2018/017156 | A1 | 1/2018 |
| WO | 2020/092835 | A1 | 5/2020 |
| WO | 2020/142313 | A1 | 7/2020 |
| WO | 2022/051485 | A2 | 3/2022 |

OTHER PUBLICATIONS

Gessl et al., “Anti-ruthenium antibodies mimic macro-TSH in electrochemiluminescent immunoassay,” Clin Chem Lab Med 52(11):1589-1594 (2014).

Lin et al., “A Sulfhydryl-Reactive Ruthenium (II) Complex and Its Conjugation to Protein G as a Universal Reagent for Fluorescent Immunoassays,” PLoS One 7(4):e36086 (2012).

Ohba et al., “Falsely elevated thyroid hormone levels caused by antiruthenium interference in the Elecsys assay resembling the syndrome of inappropriate secretion of thyrotropin,” Endocr J 59(8):663-667 (2012).

Sargeant et al., “Platform Perfection,” Medical Product Outsourcing, May 17, 2010. Accessed at <https://www.mpo-mag.com/issues/2010-05/view_features/platform-perfection>.

Zhu et al., “Electrochemiluminescence Immunosensor Based on Au Nanocluster and Hybridization Chain Reaction Signal Amplification for Ultrasensitive Detection of Cardiac Troponin I,” ACS Sens 4(10):2778-2785 (2019).

International Search Report in International Application No. PCT/US2022/035068, dated Jan. 12, 2022.

Adler et al., “Detection of rViscumin in plasma samples by immuno-PCR,” Biochemical and Biophysical Research Communications 300:757-763 (2003).

Andras et al., “Strategies for Signal Amplification in Nucleic Acid Detection,” Molecular Biotechnology 19:29-44 (2001).

Baner et al., “Signal Amplification of Padlock Probes by Rolling Circle Replication,” Nucleic Acids Research 26(22):5073-5078 (1998).

Break et al., “Utilization of the N-PLEX™ Platform for the Detection of Antisense Oligonucleotides (ASOs) in Plasma,” Molecular

(56) References Cited

OTHER PUBLICATIONS

Therapy; 2020 ASGCT Annual Meeting Abstracts, 28(4-S1):549 (2020).
Chan, "General principle of immunoassay." Immunoassay: A Practical Guide, pp. 1-23 (1987).
Dahl et al., "Circle-to-Circle Amplification for Precise and Sensitive DNA Analysis," Proceedings of the National Academy of Sciences USA 101(13):4548-4553 (2004).
Darmanis et al., "Self-Assembly of Proximity Probes for Flexible and Modular Proximity Ligation Assays," BioTechniques 46(4):443-450 (2007).
Darmanis et al., "Sensitive Plasma Protein Analysis by Microparticle-Based Proximity Ligation Assays," Molecular Cell Proteomics 9(2): 327-335 (2010).
Darmanis et al., "ProteinSeq: High-Performance Proteomic Analyses by Proximity Ligation and Next Generation Sequencing," PLOS One 6(9) p. e25583 (2011).
Dean et al., "Rapid Amplification of Plasmid and Phage DNA Using Phi29 DNA Polymerase and Multiply-Primed Rolling Circle Amplification," Genome Research 1095-1099 (2001).
Ericsson et al., "A Dual-Tag Microarray Platform for High-Performance Nucleic Acid and Protein Analyses," Nucleic Acids Research 36(8):e45 (2008).
Faruqi et al., "High-Throughput Genotyping of Single Nucleotide Polymorphisms With Rolling Circle Amplification," BMC Genomics 2:4 (2001).
Fire et al., "Rolling Replication of Short DNA Circles," Proceedings of the National Academy of Sciences USA 92:4641-4645 (1995).
Flamme et al., "Applications of Ruthenium Complexes Covalently Linked to Nucleic Acid Derivatives," *Molecules*, 23:1515 (2018).
Fredriksson et al., "Multiplexed Protein Detection by Proximity Ligation for Cancer Biomarker Validation," Nature Methods 4(4):327-329 (2007).
Fredriksson et al., Supplementary Table 2, "Multiplexed Protein Detection by Proximity Ligation for Cancer Biomarker Validation," Nature Methods 4(4):327-329 (2007).
Fredriksson et al., "Protein Detection Using Proximity-Dependent DNA Ligation Assays," Nature Biotechnology 20:473-477 (2002).
Gajadhar et al., "A Proximity Ligation Assay Using Transiently Transfected, Epitope-Tagged Proteins: Application for In Situ Detection of Dimerized Receptor Tyrosine Kinases," Bio Techniques 48(2):145-151 (2010).
Ghesquiere et al., "What Does the Future Hold for Photo-Oxidizing $Ru^{II}$Complexes with Polyazaaromatic Ligands in Medicinal Chemistry?" Curr Top Med Chem. 12:185-196 (2012).
Gill et al., "Nucleic Acid Isothermal Amplification Technologies—A Review," Nucleosides, Nucleotides, and Nucleic Acids 27:224-243 (2008).
Griffiths et al., "Miniaturising the Laboratory in Emulsion Droplets," Trends in Biotechnology 24(9):395-402 (2006).
Gu et al., "Protein tag-mediated conjugation of oligonucleotides to recombinant affinity binders for proximity ligation," New Biotechnology 30(2):144-152 (2013).
Gullberg M. et al., "A Sense of Closeness: Protein Detection by Proximity Ligation," Current Opinion in Biotechnology 14:82-86 (2003).
Gustafsdottir et al., "Detection of Individual Microbial Pathogens by Proximity Ligation," Clinical Chemistry 52(6):1152-1160 (2006).
He, "Development of on-chip proximity ligation assay with in situ single molecule sequencing readout," Masters Dissertation, Uppsala University (2011).
Heyduk et al., "Molecular Pincers: Antibody-Based Homogeneous Protein Sensors," Analytical Chemistry 80(13):5152-5159 (2008).
Hochman et al., "An Active Antibody Fragment (Fv) Composed of the Variable Portions of Heavy and Light Chains," Biochemistry 12(6):1130-1135 (1973).
Holder et al., "Assignment of Neisseria Meningitidis Serogroup A and C Class-Specific Anticapsular Antibody Concentrations to the New Standard Reference Serum CDC1992," Clinical and Diagnostic Laboratory Immunology 2(2):132-137 (1995).
Hu et al., "Quantitation of Femtomolar Protein Levels Via Direct Readout With the Electrochemical Proximity Assay," Journal of the American Chemical Society 134(16):7066-7072 (2012).
Jeong et al., "Isothermal DNA Amplification In Vitro: The Helicase-Dependent Amplification System," Cellular and Molecular Life Sciences 66:3325-3336 (2009).
Kopecky et al., "Quantification of HDL Proteins, Cardiac Events, and Mortality in Patients with Type 2 Diabetes on Hemodialysis," Clin J Am Soc Nephrol 10:224-231 (2015).
Kumar et al., "Development & evaluation of biotinylated DNA probe for clinical diagnosis of chikungunya infection in patients' acute phase serum & CSF samples," Indian J Med Res. 138:117-124 (2013).
Landegren et al., "A Ligase-Mediated Gene Detection Technique," Science 241:1077:1080 (1988).
Lee et al., "Diffractometric Detection of Proteins using Microbead-based Rolling Circle Amplification," Analytical Chemistry 82(1):197 (2010).
Leuchowius et al., "Parallel Visualization of Multiple Protein Complexes in Individual Cells in Tumor Tissue," Molecular & Cellular Proteomics 12:1563-1571 (2013).
Lizardi et al., "Mutation Detection and Single-Molecule Counting Using Isothermal Rolling-Circle Amplification," Nature Genetics 19:225-232 (1998).
Marchese et al., "Optimization and Validation of a Multiplex, Electrochemiluminescence-Based Detection Assay for the Quantitation of Immunoglobulin G Serotype-Specific Antipneumococcal Antibodies in Human Serum," Clinical and Vaccine Immunology 16(3):387-396 (2009).
Mendoza et al., "High-Throughput Microarray-Based Enzyme-Linked Immunosorbent Assay (ELISA)," BioTechniques 27(4):778-788 (1999).
Meso Scale Discovery Inc: "Sandwich Immunogenicity Assays for Protein Drugs," Meso Scale Discovery, Inc. Rockville, Maryland USA (Nov. 1, 2012).
Nallur et al., "Signal Amplification by Rolling Circle Amplification on DNA Microarrays," Nucleic Acids Research 29(23):e118 (2001).
Niemeyer et al., "Fluorometric Polymerase Chain Reaction (PCR) Enzyme-Linked Immunosorbent Assay for Quantification of Immuno-PCR Products in Microplates," Analytical Biochemistry 246:140-145 (1997).
Nilsson et al., "Padlock Probes: Circularizing Oligonucleotides for Localized DNA Detection," Science 265:2085-2088 (1994).
Nolan et al., "Multiplexed and Microparticle-Based Analyses: Quantitative Tools for the Large-Scale Analysis of Biological Systems," Cytometry Part A 69A:318-325 (2006).
Nong et al., "Solid-phase Proximity Ligation Assays for Individual or Parallel Protein Analyses with Readout via Real-Time PCR or Sequencing," Nat. Protocols, 8(6): 1234-1248 (2013).
Nordengrahn et al., "Evaluation of a Novel Proximity Ligation Assay for the Sensitive and Rapid Detection of Foot-and-Mouth Disease Virus," Veterinary Microbiology 127:227-236 (2008).
Olink Bioscience: DuoLink II Probemaker PLUS, Duolink II Probemaker MINUS, Product Insert Doc No. 0564 (2012).
Porter et al., "Subunits of Immunoglobulins and Their Relationship to Antibody Specificity," Journal of Cellular Physiology 67(Sup 1):51-64 (1966).
Ribas et al., "Human apolipoprotein A-II enrichment displaces paraoxonase from HDL and impairs its antioxidant properties: a new mechanism linking HDL protein composition and antiatherogenic potential," Circ Res 95(8):789-797 (2004).
Samiotaki et al., "Dual-Color Detection of DNA Sequence Variants by Ligase-Mediated Analysis," Genomics 20:238-242 (1994).
Schallmeiner et al., "Sensitive Protein Detection Via Triple-Binder Proximity Ligation Assays," Nature Methods 4(2):135-137 (2007).
Schweitzer et al., "Multiplexed Protein Profiling on Microarrays by Rolling-Circle Amplification," Nature Biotechnology 20:359-365 (2002).
Schweitzer et al., "Immunoassays With Rolling Circle DNA Amplification: A Versatile Platform for Ultrasensitive Antigen Detection," Proceedings of the National Academy of Sciences USA 97(18):10113-10119 (2000).

(56) References Cited

OTHER PUBLICATIONS

Shibayama et al., "Nucleic acid (DNA/RNA) quantitative method," *Bunseki J.* 7:268-274 (2018).
Soderberg et al., "Direct observation of individual endogenous protein complexes in situ by proximity ligation," Nature Methods 3(12):995-1000 (2006).
Soderberg et al., "Characterizing Proteins and Their Interactions in Cells and Tissues Using the In Situ Proximity Ligation Assay," Methods 45:227-232 (2008).
Spits et al., "Whole-Genome Multiple Displacement Amplification from Single Cells," Nature Protocols 1(4):1965-1970 (2006).
Tavoosidana et al. "Multiple Recognition Assay Reveals Prostasomes as Promising Plasma Biomarkers for Prostate Cancer," PNAS 108(21):8809-8814 (2011).
Vincent et al., "Helicase-Dependent Isothermal DNA Amplification," European Molecular Biology Organization 5(8):795-800 (2004).
Vuoriluoto et al., "Spatio-Temporal Composition of the Mitotic Chromosomal Passenger Complex Detected Using In Situ Proximity Ligation Assay," Molecular Oncology 5:105-111 (2011).
Watanabe et al., "Proteomic profiling following immunoaffinity capture of high-density lipoprotein: association of acute-phase proteins and complement factors with proinflammatory high-density lipoprotein in rheumatoid arthritis," Arthritis Rheum 64(6):1828-1837 (2012).
Weibrecht et al., "Proximity Ligation Assays: A Recent Addition to the Proteomics Toolbox," Expert Review of Proteomics 7(3):401-409 (2010).
Yamada et al., "Detection of Methicillin-Resistant *Staphylococcus aureus* Using a Specific Anti-PBP2a Chicken IgY Antibody," Japanese Journal of Infectious Diseases 66:103-108 (2013).
Zhang et al., "Amplification of Circularizable Probes for the Detection of Target Nucleic Acids and Proteins," Clinica Chimica Acta 363:61-70 (2006).
Zhang et al., "Ruthenium Polypyridine Complexes Combined with Oligonucleotides for Bioanalysis: A Review," Molecules 19:11933-11987 (2014).
Zhou H. et al., "Two-Color, Rolling-Circle Amplification on Antibody Microarrays for Sensitive, Multiplexed Serum-Protein Measurements," Genome Biology 5:R28 (2004).
International Search Report in PCT/US2012/064263, dated Mar. 15, 2013.
International Search Report in PCT/US2014/024279, dated Jul. 17, 2014.
International Search Report in PCT/US2014/026010, dated Jul. 7, 2014.
International Search Report in PCT/US2015/030925, dated Aug. 27, 2015.
International Search Report in PCT/US2020/020288, dated May 14, 2020.
International Search Report in PCT/US2021/048854, dated Feb. 24, 2023.
International Search Report in PCT/US2023/084737, dated May 15, 2024.
Restriction Requirement in U.S. Appl. No. 14/357,653, dated Jul. 31, 2015.
Non-Final Office Action in U.S. Appl. No. 14/357,653, dated Oct. 26, 2015.
Final Office Action in U.S. Appl. No. 14/357,653, dated Jun. 22, 2016.
Non-Final Office Action in U.S. Appl. No. 14/357,653, dated Jan. 31, 2017.
Non-Final Office Action in U.S. Appl. No. 15/696,953, dated Mar. 27, 2019.
Final Office Action in U.S. Appl. No. 15/696,953, dated Nov. 25, 2019.
Final Office Action in U.S. Appl. No. 15/696,953, dated Jun. 15, 2020.
Non-Final Office Action in U.S. Appl. No. 15/696,953, dated Mar. 9, 2021.
Notice of Allowance issued in U.S. Appl. No. 15/696,953, dated Sep. 27, 2021.
Non-Final Office Action in U.S. Appl. No. 17/504,937, dated Apr. 17, 2023.
Final Office Action in U.S. Appl. No. 17/504,937, dated Oct. 16, 2023.
Non-Final Office Action in U.S. Appl. No. 17/504,937, dated Sep. 25, 2024.
Non-Final Office Action in U.S. Appl. No. 14/206,284, dated Oct. 16, 2015.
Final Office Action in U.S. Appl. No. 14/206,284, dated Jul. 6, 2016.
Non-Final Office Action in U.S. Appl. No. 15/440,191, dated Jun. 20, 2019.
Final Office Action in U.S. Appl. No. 15/440,191, dated Dec. 16, 2019.
Final Office Action in U.S. Appl. No. 15/440,191, dated May 22, 2020.
Non-Final Office Action in U.S. Appl. No. 17/132,380, dated Nov. 24, 2023.
Final Office Action in U.S. Appl. No. 17/132,380, dated May 3, 2024.
Advisory Action in U.S. Appl. No. 17/132,380, dated Jul. 29, 2024.
Notice of Allowance in U.S. Appl. No. 17/132,380, dated Aug. 7, 2024.
Non-Final Office Action in U.S. Appl. No. 14/208,040, dated Dec. 30, 2015.
Final Office Action in U.S. Appl. No. 14/208,040, dated Oct. 11, 2016.
Non-Final Office Action in U.S. Appl. No. 14/208,040, dated Feb. 7, 2017.
Final Office Action in U.S. Appl. No. 14/208,040, dated Jul. 27, 2017.
Non-Final Office Action in U.S. Appl. No. 14/208,040, dated Jan. 16, 2018.
Restriction Requirement in U.S. Appl. No. 16/136,498, dated Mar. 19, 2021.
Non-Final Office Action issued in U.S. Appl. No. 16/136,498, dated Oct. 13, 2021.
Final Office Action issued in U.S. Appl. No. 16/136,498, dated Apr. 20, 2022.
Advisory Action issued in U.S. Appl. No. 16/136,498, dated Jul. 5, 2022.
Non-Final Office Action in U.S. Appl. No. 16/136,498, dated Oct. 14, 2022.
Notice of Allowance in U.S. Appl. No. 16/136,498, dated Feb. 21, 2023.
Notice of Allowance in U.S. Appl. No. 16/136,498, dated Mar. 1, 2023.
Non-Final Office Action in U.S. Appl. No. 15/311,309, dated May 4, 2018.
Final Office Action in U.S. Appl. No. 15/311,309, dated Oct. 26, 2018.
Notice of Allowance issued in U.S. Appl. No. 15/311,309, dated May 9, 2019.
Restriction Requirement in U.S. Appl. No. 16/564,208, dated Nov. 10, 2020.
Non-Final Office Action in U.S. Appl. No. 16/564,208, dated May 10, 2021.
Final Office Action issued in U.S. Appl. No. 16/564,208, dated Oct. 6, 2021.
Advisory Action issued in U.S. Appl. No. 16/564,208, dated Jan. 27, 2022.
Notice of Allowance in U.S. Appl. No. 16/564,208, dated Apr. 25, 2022.
Supplemental Notice of Allowance in U.S. Appl. No. 16/564,208, dated May 18, 2022.
Supplemental Notice of Allowance in U.S. Appl. No. 16/564,208, dated Jul. 21, 2022.
Supplemental Notice of Allowance in U.S. Appl. No. 16/564,208, dated Aug. 17, 2022.
Restriction Requirement in U.S. Appl. No. 17/813,965, dated Mar. 19, 2024.

(56) References Cited

OTHER PUBLICATIONS

Non-Final Office Action in U.S. Appl. No. 17/813,965, dated Jul. 18, 2024.
Non-Final Office Action in U.S. Appl. No. 17/813,965, dated Dec. 19, 2024.
Notice of Allowance in U.S. Appl. No. 17/813,965, dated May 9, 2025.
Restriction Requirement in U.S. Appl. No. 17/434,938, dated Jan. 24, 2025.
Non-Final Office Action in U.S. Appl. No. 17/434,938, dated Jun. 2, 2025.
Notice of Allowance in U.S. Appl. No. 17/434,938, dated Oct. 1, 2025.
Notice of Allowance in U.S. Appl. No. 17/434,938, dated Nov. 5, 2025.
Non-Final Office Action in U.S. Appl. No. 18/043,275, dated Sep. 25, 2025.
Break et al., "Use of the N-PLEX™ Platform for the Detection of Antisense Oligonucleotides (ASOs) in Plasma," Meso Scale Discovery, copyright 2020. Accessed at <https://www.mesoscale.com/~/media/files/scientific%20poster/n-plex-for-detection-of-asos-in-plasma-asgct-2020.pdf>.
GeneLink™ "Thiol SS-C6 Product Specifications—Oligo Modifications." Accessed at <https://www.genelink.com/newsite/products/mod_detail.asp?modid=40>.
Glen Research Report, vol. 4, No. 1, issued Mar. 1991.
MSD, "Use of the N-PLEX™ Platform for the Detection of Antisense Oligonucleotides (ASOs) in Plasma," Scientific Poster for ASGCT 2020. Accessed at <https://www.mesoscale.com/en/technical_resources/search_all_documents/?sc_itemid= 61fe0de9-be0d-4193-8bff-057e55552313>.
Non-Final Office Action issued in U.S. Appl. No. 18/320,411, dated Jan. 9, 2026.
Adamczyk et al., "Design of Acridinium-9-carboxamides and Anti-acridinium Antibodies for Chemiluminescent Signal Enhancement," Bioconjugate Chemistry 12(3): 329-331 (2001).

* cited by examiner

| ECL Assay Signal with Anti-SULFO-TAG Antibody | | | | | | | | | |
|---|---|---|---|---|---|---|---|---|---|
| | | Human ZnT8 20 pg/mL | | Human IA-2 200 pg/mL | | Human TGM-2 (400 pg/mL) | | Mouse IL-1b (20 pg/mL) | |
| | | Biotinylated Capture | SULFO-TAG Detect | Biotinylated Capture | SULFO-TAG Detect | Biotinylated Capture | SULFO-TAG Detect | Biotinylated Capture | SULFO-TAG Detect |
| | Clone Name | F67-7C2-8 | F67-1A7-6 | F71-11A1-2t | F71-10A12-7 | F74-6A5-6 | F69-5E8-3t | RF87-1B3-6 | RF87-6B3-10 |
| Anti-SULFO-TAG Antibody | F136-1B4-8 | 210,149 | | 839,628 | | 291,140 | | 986,699 | |
| | F136-3A12-2 | 77,260 | | 328,276 | | 88,161 | | 337,824 | |
| | F136-3F10-6 | 292,860 | | 1,121,087 | | 432,569 | | 1,469,588 | |
| | F136-5E9-2t | 17,781 | | 97,821 | | 32,062 | | 136,450 | |
| | F136-6F9-3 | 305,881 | | 1,084,435 | | 418,401 | | 1,474,103 | |
| | F136-7D11-4m | 125,401 | | 829,990 | | 274,382 | | 914,267 | |
| | F136-8E1-1 | 64,088 | | 306,621 | | 106,239 | | 480,129 | |
| | F137-6B9-1 | 38,630 | | 373,240 | | 117,454 | | 455,082 | |
| | F144-4G7-3 | 13,923 | | 176,253 | | 58,275 | | 194,376 | |
| | F144-8B2-2 | 32,921 | | 217,305 | | 71,203 | | 288,469 | |
| | F145-10A9-1m | 15,670 | | 260,332 | | 62,039 | | 228,476 | |
| | No Anti-SULFO-TAG | 1,244 | | 2,012 | | 1,265 | | 3,094 | |

FIG. 6

| Anti-SULFO-TAG Antibody Enhancement of Human ZnT8 Calibrator Titration | | | | | | | | | | | | | |
|---|---|---|---|---|---|---|---|---|---|---|---|---|---|
| | Clone Number | F136-1B4-8 | | F136-3F10-6 | | F136-6F9-3 | | F136-7D11-4m | | F136-8E1-1 | | F137-6B9-1 | |
| Standards | Concentration (pg/mL) | Average ECL | Average ECL CV% | Average ECL | Average ECL CV% | Average ECL | Average ECL CV% | Average ECL | Average ECL CV% | Average ECL | Average ECL CV% | Average ECL | Average ECL CV% |
| STD 01 | 100.00 | 1,089,575 | 1.3 | 1,424,443 | 2.0 | 1,445,944 | 0.0 | 842,035 | 9.9 | 463,623 | 2.9 | 231,297 | 4.9 |
| STD 02 | 25.00 | 283,098 | 14.4 | 485,020 | 5.6 | 496,661 | 3.0 | 178,203 | 4.2 | 107,160 | 0.5 | 58,327 | 14.3 |
| STD 03 | 6.25 | 62,414 | 29.0 | 124,156 | 1.6 | 119,301 | 3.8 | 30,381 | 62.3 | 27,532 | 2.9 | 16,284 | 4.5 |
| STD 04 | 1.56 | 21,579 | 0.3 | 37,988 | 2.1 | 29,102 | 9.4 | 13,223 | 2.3 | 8,608 | 0.3 | 7,332 | 5.8 |
| STD 05 | 0.39 | 9,656 | 0.4 | 19,605 | 0.1 | 11,269 | 1.8 | 5,578 | 1.6 | 4,227 | 0.8 | 4,986 | 12.8 |
| STD 06 | 0.10 | 6,410 | 3.2 | 13,471 | 5.2 | 5,869 | 9.8 | 3,875 | 2.1 | 3,152 | 10.4 | 4,427 | 8.6 |
| STD 07 | 0.02 | 5,946 | 4.1 | 12,817 | 2.0 | 5,114 | 4.1 | 3,438 | 1.3 | 2,998 | 6.7 | 4,378 | 3.9 |
| STD 08 | 0.00 | 5,338 | 4.4 | 13,224 | 7.1 | 4,099 | 6.5 | 3,192 | 0.6 | 2,801 | 3.2 | 4,213 | 0.3 |
| | Hill Slope | 1.03 | | 1.09 | | 1.07 | | 1.13 | | 1.05 | | 1.05 | |
| | R squared | 1.00 | | 1.00 | | 1.00 | | 1.00 | | 1.00 | | 1.00 | |
| | LLOD | 0.01 | | 0.01 | | 0.02 | | 0.03 | | 0.03 | | 0.05 | |
| | S/B (STD 04/STD 08) | 4 | | 3 | | 7 | | 4 | | 3 | | 2 | |
| | S/N (STD 04/STD 08) | 20 | | 14 | | 36 | | 21 | | 15 | | 9 | |

FIG. 7

| Anti-SULFO-TAG Antibody Enhancement of Human TGM-2 Calibrator Titration | | | | | | | | | | | | | |
|---|---|---|---|---|---|---|---|---|---|---|---|---|---|
| | Clone Number | F136-1B4-8 | | F136-3F10-6 | | F136-6F9-3 | | F136-7D11-4m | | F136-8E1-1 | | F137-6B9-1 | |
| Standards | Concentration (pg/mL) | Average ECL | Average ECL CV% | Average ECL | Average ECL CV% | Average ECL | Average ECL CV% | Average ECL | Average ECL CV% | Average ECL | Average ECL CV% | Average ECL | Average ECL CV% |
| STD 01 | 1,000.00 | 869,251 | 1.8 | 1,229,535 | 0.6 | 1,219,217 | 2.3 | 992,555 | 30.4 | 293,167 | 4.4 | 378,602 | 18.9 |
| STD 02 | 250.00 | 203,943 | 1.5 | 294,626 | 22.5 | 334,042 | 6.4 | 197,153 | 3.5 | 83,422 | 5.3 | 91,111 | 28.3 |
| STD 03 | 62.50 | 49,051 | 1.2 | 88,863 | 0.9 | 81,365 | 6.4 | 53,615 | 6.4 | 21,041 | 1.7 | 25,648 | 5.7 |
| STD 04 | 15.63 | 17,249 | 4.1 | 31,907 | 1.5 | 22,786 | 0.9 | 14,433 | 0.8 | 7,157 | 1.1 | 9,987 | 1.8 |
| STD 05 | 3.91 | 8,532 | 2.3 | 18,259 | 4.1 | 9,217 | 6.2 | 6,327 | 1.7 | 4,060 | 2.1 | 6,721 | 1.4 |
| STD 06 | 0.98 | 5,804 | 6.4 | 15,699 | 7.3 | 6,492 | 2.6 | 4,433 | 2.4 | 3,466 | 4.3 | 5,881 | 4.7 |
| STD 07 | 0.24 | 6,265 | 1.4 | 15,447 | 0.5 | 5,477 | 5.9 | 3,918 | 3.1 | 3,294 | 0.2 | 6,027 | 0.0 |
| STD 08 | 0.00 | 5,512 | 6.2 | 14,240 | 1.2 | 5,029 | 6.7 | 3,574 | 1.9 | 3,248 | 2.2 | 5,504 | 1.3 |
| | Hill Slope | 1.05 | | 1.02 | | 1.06 | | 1.07 | | 1.12 | | 1.07 | |
| | R squared | 1.00 | | 1.00 | | 1.00 | | 1.00 | | 1.00 | | 1.00 | |
| | LLOD | 0.39 | | 0.20 | | 0.46 | | 0.32 | | 0.47 | | 0.35 | |
| | S/B (STD 04/STD 08) | 3 | | 2 | | 5 | | 4 | | 2 | | 2 | |
| | S/N (STD 04/STD 08) | 16 | | 11 | | 23 | | 20 | | 11 | | 9 | |

FIG. 8

Comparison Data for Human ZnT8 and Human TGM-2 (Assays without Anti-SULFO-TAG Antibody)

| Analyte | | Human ZnT8 | |
|---|---|---|---|
| Capture | | F67-7C2-8 | |
| Detect | | F67-1A7-6 | |
| Standards | Conc. (pg/ml) | Avg ECL | CV% |
| STD 01 | 5,000.00 | 599,672 | 2.4 |
| STD 02 | 1,250.00 | 273,168 | 3.7 |
| STD 03 | 312.5 | 75,165 | 0.8 |
| STD 04 | 78.1 | 19,069 | 2.0 |
| STD 05 | 19.5 | 4,695 | 1.5 |
| STD 06 | 4.9 | 1,310 | 4.5 |
| STD 07 | 1.2 | 397 | 1.8 |
| STD 08 | 0 | 59 | 10.9 |
| Hill Slope | | 1.00 | |
| R squared | | 1.00 | |
| LLOD | | 0.29 | |
| S/B (STD 04/STD 08) | | 326 | |
| S/N (STD 04/STD 08) | | 1,239 | |

| Analyte | | Human TGM-2 | |
|---|---|---|---|
| Capture | | F74-6A5-6 | |
| Detect | | F69-5E8-3t | |
| Standards | Conc. (pg/ml) | Avg ECL | CV% |
| STD 01 | 100,000 | 1,302,398 | 1.8 |
| STD 02 | 25,000 | 409,736 | 4.1 |
| STD 03 | 6250 | 99,438 | 1.9 |
| STD 04 | 1563 | 25,107 | 1.3 |
| STD 05 | 391 | 5,933 | 3.5 |
| STD 06 | 98 | 1,617 | 2.8 |
| STD 07 | 24 | 447 | 7.1 |
| STD 08 | 0 | 72 | 28.7 |
| Hill Slope | | 1.02 | |
| R squared | | 1.00 | |
| LLOD | | 5.11 | |
| S/B (STD 04/STD 08) | | 351 | |
| S/N (STD 04/STD 08) | | 1.439 | |

FIG. 9

| Anti-SULFO-TAG Antibody Enhancement of Mouse IL-23 Calibrator Titration | | | | | | | | | | | | | |
|---|---|---|---|---|---|---|---|---|---|---|---|---|---|
| | Clone Number | F136-1B4-8 | | F136-3F10-6 | | F136-6F9-3 | | F136-7D11-4m | | F136-8E1-1 | | F137-6B9-1 | |
| Standards | Concentration (pg/mL) | Average ECL | Average ECL CV% | Average ECL | Average ECL CV% | Average ECL | Average ECL CV% | Average ECL | Average ECL CV% | Average ECL | Average ECL CV% | Average ECL | Average ECL CV% |
| STD 01 | 79.69 | 371,697 | 6.5 | 425,778 | 8.5 | 508,084 | 2.6 | 322,382 | 15.2 | 144,442 | 5.9 | 165,110 | 0.3 |
| STD 02 | 4.98 | 20,684 | 9.9 | 28,732 | 2.2 | 27,397 | 5.8 | 18,928 | 6.7 | 8,717 | 2.7 | 9,241 | 0.8 |
| STD 03 | 0.31 | 2,290 | 1.1 | 4,842 | 4.5 | 2,586 | 3.5 | 1,836 | 4.1 | 1,101 | 2.4 | 1,383 | 3.1 |
| STD 04 | 0 | 930 | 9.4 | 3,323 | 11.3 | 1,143 | 3.5 | 647 | 5.6 | 596 | 0.4 | 876 | 0.1 |
| | Hill Slope | 1.03 | | 1.02 | | 1.06 | | 1.02 | | 1.03 | | 1.06 | |
| | R squared | 1.00 | | 1.00 | | 1.00 | | 1.00 | | 1.00 | | 1.00 | |
| | LLOD | 0.021 | | 0.114 | | 0.025 | | 0.026 | | 0.051 | | 0.058 | |
| | S/B (STD 02/STD 04) | 22 | | 9 | | 24 | | 29 | | 15 | | 11 | |
| | S/N (STD 02/STD 04) | 111 | | 43 | | 120 | | 146 | | 73 | | 53 | |

FIG. 10

| Anti-SULFO-TAG Antibody Enhancement of Mouse IL-17C Calibrator Titration | | | | | | | | | | | | | |
|---|---|---|---|---|---|---|---|---|---|---|---|---|---|
| | Clone Number | F136-1B4-8 | | F136-3F10-6 | | F136-6F9-3 | | F136-7D11-4m | | F136-8E1-1 | | F137-6B9-1 | |
| Standards | Concentration (pg/mL) | Average ECL | Average ECL CV% | Average ECL | Average ECL CV% | Average ECL | Average ECL CV% | Average ECL | Average ECL CV% | Average ECL | Average ECL CV% | Average ECL | Average ECL CV% |
| STD 01 | 178.13 | 740,503 | 6.8 | 1,005,824 | 3.2 | 1,052,707 | 0.9 | 733,413 | 1.5 | 325,900 | 3.7 | 348,373 | 0.5 |
| STD 02 | 11.13 | 55,314 | 3.4 | 69,500 | 3.8 | 64,867 | 5.3 | 49,239 | 3.3 | 22,511 | 1.6 | 23,026 | 17.8 |
| STD 03 | 0.7 | 14,324 | 0.0 | 18,654 | 3.7 | 17,153 | 0.7 | 8,968 | 18.7 | 4,509 | 6.7 | 6,333 | 1.8 |
| STD 04 | 0 | 10,730 | 3.4 | 14,653 | 1.3 | 12,926 | 3.1 | 7,408 | 3.1 | 3,510 | 14.1 | 5,044 | 1.8 |
| | Hillslope | 1.00 | | 1.04 | | 1.07 | | 1.19 | | 1.06 | | 1.06 | |
| | Rsquared | 1.00 | | 1.00 | | 1.00 | | 1.00 | | 1.00 | | 1.00 | |
| | LLOD | 0.018 | | 0.113 | | 0.090 | | 0.299 | | 0.538 | | 0.178 | |
| | S/B (STD 02/STD 04) | 5 | | 5 | | 5 | | 7 | | 6 | | 5 | |
| | S/N (STD 02/STD 04) | 26 | | 24 | | 25 | | 33 | | 32 | | 23 | |

FIG. 11

Comparison Data for Mouse IL-23 and Mouse IL-17C (Assays without Anti-SULFO-TAG Antibody)

| Analyte | | Mouse IL-23 | |
|---|---|---|---|
| Capture | | AF1619 | |
| Detect | | MAB4991 | |
| Standards | Conc. (pg/ml) | Avg | CV% |
| STD 01 | 20,400 | 373,508 | 1.5 |
| STD 02 | 5,100 | 120,184 | 1.1 |
| STD 03 | 1275 | 31,957 | 1.2 |
| STD 04 | 319 | 8,065 | 1.4 |
| STD 05 | 79.7 | 2,193 | 1.6 |
| STD 06 | 19.9 | 664 | 2.3 |
| STD 07 | 5.0 | 308 | 3.9 |
| STD 08 | 0 | 185 | 9.0 |
| LLOD | | 4.9 | |

| Analyte | | Mouse IL-17C | |
|---|---|---|---|
| Capture | | MAB2306 | |
| Detect | | AF2306 | |
| Standards | Conc. (pg/ml) | Avg | CV% |
| STD 01 | 45,600 | 2,847,357 | 0.5 |
| STD 02 | 11,400 | 1,020,146 | 1.3 |
| STD 03 | 2850 | 260,634 | 1.3 |
| STD 04 | 713 | 62,529 | 2.1 |
| STD 05 | 178 | 15,942 | 1.7 |
| STD 06 | 45 | 4,006 | 1.6 |
| STD 07 | 11 | 1,211 | 1.4 |
| STD 08 | 0 | 205 | 7.0 |
| LLOD | | 2.3 | |

FIG. 12

| Anti-SULFO-TAG Antibody Enhancement of Human IL-10 Calibrator Titration | | | | | | | | | | | | | |
|---|---|---|---|---|---|---|---|---|---|---|---|---|---|
| | Clone Number | F136-1B4-8 | | F136-3F10-6 | | F136-6F9-3 | | F136-7D11-4m | | F136-8E1-1 | | F137-6B9-1 | |
| Standards | Concentration (pg/mL) | Average ECL | Average ECL CV% | Average ECL | Average ECL CV% | Average ECL | Average ECL CV% | Average ECL | Average ECL CV% | Average ECL | Average ECL CV% | Average ECL | Average ECL CV% |
| STD 01 | 10 | 1,258,766 | 1.5 | 1,279,151 | 1.5 | 1,359,035 | 1.5 | 1,097,899 | 1.7 | 612,860 | 4.6 | 811,468 | 2.0 |
| STD 02 | 0.63 | 81,752 | 1.0 | 91,823 | 1.4 | 97,975 | 1.4 | 68,517 | 7.1 | 38,408 | 1.4 | 42,023 | 10.6 |
| STD 03 | 0.04 | 9,142 | 4.6 | 11,581 | 0.5 | 11,463 | 1.3 | 5,846 | 1.0 | 4,340 | 2.8 | 4,570 | 5.3 |
| STD 04 | 0 | 4,378 | 0 2 | 5,928 | 6.6 | 5,172 | 1.7 | 1,330 | 4.9 | 1,771 | 2.4 | 1,605 | 1.4 |
| | Hillslope | 1.01 | | 0.98 | | 0.97 | | 0.99 | | 1.00 | | 1.03 | |
| | Rsquared | 1.00 | | 1.00 | | 1.00 | | 1.00 | | 1.00 | | 1.00 | |
| | LLOD | 0.00063 | | 0.00101 | | 0.00124 | | 0.00131 | | 0.00167 | | 0.00128 | |
| | S/B (STD 02/STD 04) | 19 | | 15 | | 19 | | 52 | | 22 | | 26 | |
| | S/N (STD 02/STD 04) | 93 | | 77 | | 95 | | 257 | | 108 | | 131 | |

FIG. 13

| Comparison Data for Human IL-10 (Assays without Anti-SULFO-TAG Antibody) | | | |
|---|---|---|---|
| Analyte | | Human IL-10 | |
| Capture | | 2108-A82-8 | |
| Detect | | 1299-A06-5 | |
| Standards | Conc. (pg/ml) | Avg | CV% |
| STD 01 | 1,858 | 1,088,999 | 1.7 |
| STD 02 | 465 | 351,459 | 2.2 |
| STD 03 | 116 | 102,710 | 1.9 |
| STD 04 | 29 | 26,564 | 1.6 |
| STD 05 | 7.3 | 6,756 | 3.4 |
| STD 06 | 1.8 | 1,834 | 2.3 |
| STD 07 | 0.5 | 548 | 7.7 |
| STD 08 | 0 | 151 | 21.1 |
| LLOD | | 0.09 | |

FIG. 14

| | | % Signal Inhibition | | % Signal Increase | |
|---|---|---|---|---|---|
| | | 1-(Signal inhibition/Standard Signal) | | (Signal Increase -Signal inhibition)/MAX | |
| # | a-STAG Ab Clone ID | AVR | STDEV (n=9) | AVR | STDEV (n=9) |
| 1 | F136-1B4-8 | 63% | 3% | 71% | 6% |
| 2 | F136-3A12-2 | 22% | 6% | 20% | 2% |
| 3 | F136-3F10-6 | 58% | 3% | 87% | 3% |
| 4 | F136-5E9-2I | 32% | 4% | 27% | 3% |
| 5 | F136-6F9-3 | 55% | 3% | 100% | 0% |
| 6 | F136-7D11-4m | 29% | 4% | 21% | 4% |
| 7 | F136-8E1-1 | 36% | 4% | 39% | 3% |
| 8 | F137-6B9-1 | 21% | 4% | 12% | 3% |
| 9 | F144-4G7-3 | 6% | 9% | 11% | 5% |
| 10 | F144-8B2-2 | 21% | 6% | 22% | 3% |
| 11 | F145-10A9-1m | 15% | 5% | 10% | 2% |
FIG. 16A
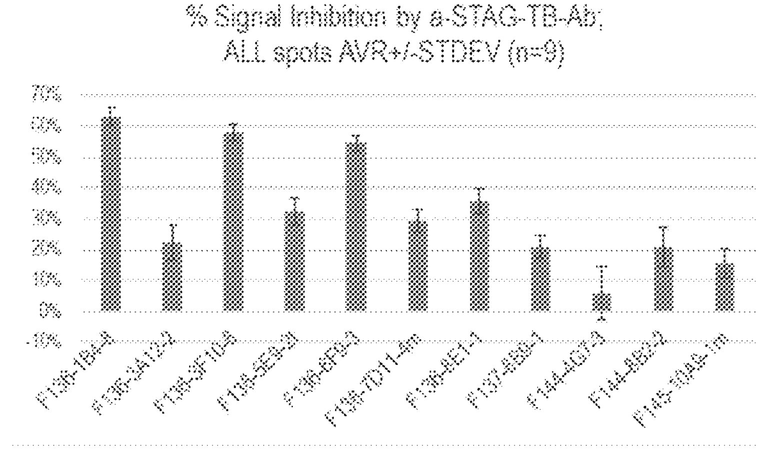
FIG. 16B
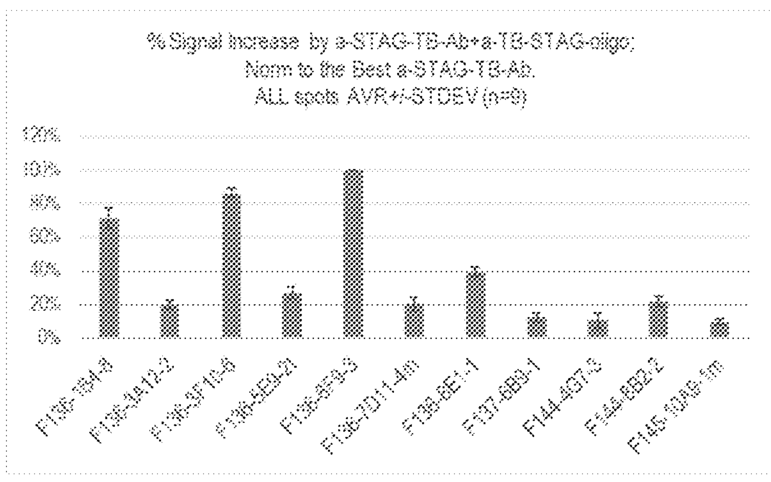
FIG. 16C $Ru^{+2}(SM)_2(A)_1$ $Ru^{+2}(SM)_3$ $Ru^{+2}(bpy)_3$ $Ru^{+2}(bpy)_2(SM)$ A = acid ligand SM = sulfomethyl ligand bpy = bipyridine ligand

| | TAG at 625 nM | TAGs at 395 nM | | |
|---|---|---|---|---|
| Values | $Ru(Bpy)_3$ | $Ru(Bpy)_2SM$ | $Ru(SM)_3$ | $Ru(SM)_2A$ |
| ECL | 393317 | 203263 | 217902 | 224676 |
| StdDev of ECL | 9315 | 3764 | 5752 | 4114 |

$Ru^{+2}(bpy)(SM)(A)$ NHS $Ru^{+2}(bpy)(SM)(A$ $Ru^{+2}(XM)_2(A)_1$

X= $-PO_3^{-2}$, $-CO_2^-$, $-B(OH)_3^-$

METHODS, COMPOSITIONS, AND KITS FOR ASSAY SIGNAL AMPLIFICATION

FIELD OF THE INVENTION

The invention relates to methods, compositions, and kits for assay signal amplification. Also provided herein is a signal amplification reagent, wherein the signal amplification reagent is an antibody or antigen-binding fragment thereof.

BACKGROUND

Immunoassays, e.g., sandwich immunoassays, are commonly used to detect analytes in a sample. Typical immunoassays often are not sensitive enough to accurately detect low abundance analytes in a sample, or the assay instrument itself is limited in detecting low signal levels. Methods to improve assay sensitivity often involve complex optimization procedures, which can be a time- and labor-intensive process. Moreover, the optimized assays can require longer run times and/or complicated analysis methods.

SUMMARY OF THE INVENTION

In embodiments, the invention provides a method of detecting an analyte of interest in a sample, comprising:

(a) contacting a first complex that comprises (A) a first detectable label, wherein the first detectable label is an electrochemiluminescent (ECL) label, and (B) the analyte of interest, with: (I) a signal amplification reagent that specifically binds to the first detectable label and that comprises a binding moiety, and (II) a detectable moiety comprising (1) a binding partner of the binding moiety and (2) one or more of a second detectable label; and (b) measuring (I) the second detectable label or (II) the first and second detectable labels, thereby detecting the analyte of interest;

or (c) contacting a first complex that comprises (A) a first detectable label, wherein the first detectable label is an ECL label, and (B) the analyte of interest, with: (I) a signal amplification reagent that specifically binds to the first detectable label and that comprises an enzyme, and (II) a substrate of the enzyme; and (d) measuring enzyme activity, thereby detecting the analyte of interest;

or (e) contacting a first complex that comprises (A) a first detectable label, wherein the first detectable label is an ECL label, and (B) the analyte of interest, with a signal amplification reagent that specifically binds to the first detectable label and that optionally comprises a second detectable label; and (f) measuring (I) the first detectable label; (II) the second detectable label; or (III) the first and second detectable labels, thereby detecting the analyte of interest;

or (g) contacting a first complex that comprises (A) a first detectable label, wherein the first detectable label is an electrochemiluminescent (ECL) label, and (B) the analyte of interest, with a signal amplification reagent that specifically binds to the first detectable label, wherein the signal amplification reagent comprises a signal amplification (SA) nucleic acid probe, thereby forming a second complex comprising the first complex and the signal amplification reagent; (h) extending the nucleic acid probe to form an extended sequence; and (i) measuring the amount of extended sequence, thereby detecting the analyte of interest. In embodiments, the first complex is on a surface.

In embodiments, the signal amplification reagent comprises a nucleic acid probe, and the surface comprises an anchoring reagent immobilized thereon. In embodiments, the signal amplification reagent comprises a nucleic acid probe, and the method further comprises immobilizing an anchoring reagent on the surface. In embodiments, the anchoring reagent is immobilized on the surface prior to or during step (h) of the method. In embodiments, the anchoring reagent binds to an anchoring region of the extended sequence, and the measuring comprises measuring the amount of extended sequence bound to the surface via the anchoring reagent.

In embodiments, the invention provides a kit for detecting an analyte of interest in a sample comprising, in one or more vials, containers, or compartments: (a) a capture reagent that specifically binds to the analyte; (b) a detection reagent that specifically binds to the analyte, wherein the detection reagent comprises a first detectable label, wherein the first detectable label is an ECL label; and (c) a signal amplification reagent that specifically binds to the first detectable label. In embodiments, the kit further comprises a surface.

In embodiments, the invention provides a method of detecting an analyte of interest in a sample, comprising (a) forming a first complex on a surface comprising the analyte of interest; a capture reagent that specifically binds to the analyte, wherein the capture reagent is immobilized on the surface or wherein the capture reagent is capable of being immobilized to the surface; and a detection reagent that specifically binds to the analyte and that comprises a first nucleic acid probe; (b) extending the first nucleic acid probe to form a first extended sequence comprising a first anchoring region, wherein the first anchoring region binds a first anchoring reagent that is immobilized on the surface; (c) binding the first extended sequence to a first labeled probe comprising a first detectable label, wherein the first detectable label is an ECL label; and:

(d) contacting the first labeled probe bound to the first extended sequence with: (I) a signal amplification reagent that specifically binds to the first detectable label and that comprises a binding moiety, and (II) a detectable moiety comprising (1) a binding partner of the binding moiety and (2) one or more of a second detectable label; and (e) measuring (I) the second detectable label or (II) the first and second detectable labels on the surface, thereby detecting the analyte of interest;

or (f) contacting the first labeled probe bound to the first extended sequence with: (I) a signal amplification reagent that specifically binds to the first detectable label and that comprises an enzyme, and (II) a substrate of the enzyme; and (g) measuring enzyme activity, thereby detecting the analyte of interest;

or (h) contacting the first labeled probe bound to the first extended sequence with a signal amplification reagent that specifically binds to the first detectable label and that optionally comprises a second detectable label; and (i) measuring (I) the first detectable label; (II) the second detectable label; or (III) the first and second detectable labels, thereby detecting the analyte of interest;

or (j) contacting the first labeled probe bound to the first extended sequence with a signal amplification reagent that specifically binds to the first detectable label, wherein the signal amplification reagent comprises a second nucleic acid probe, thereby forming a second complex comprising the signal amplification reagent and the first labeled probe; (k) extending the second nucleic acid probe to form a second extended sequence comprising a second anchoring region, wherein the second anchoring region binds a second anchoring reagent that is immobilized on the surface; and; (l) measuring the amount of (I) the second extended sequence or (II) the first extended sequence and the second extended sequence bound to the surface, thereby detecting the analyte of interest.

In embodiments, the invention provides a kit for detecting an analyte of interest in a sample comprising, in one or more vials, containers, or compartments: (a) a capture reagent that specifically binds to the analyte; (b) a detection reagent that specifically binds to the analyte, wherein the detection reagent comprises a first nucleic acid probe; (c) a first labeled probe comprising a first detectable label, wherein the first detectable label is an ECL label; and (d) a signal amplification reagent that specifically binds to the first detectable label. In embodiments, the kit further comprises a surface.

In embodiments, the invention provides an antibody or antigen-binding fragment thereof comprising an antigen binding domain specific to an ECL label.

In embodiments, the invention provides an antibody or antigen-binding fragment thereof comprising an antigen binding domain specific to: the ECL label and a conjugation linker.

In embodiments, the invention provides a composition comprising: (a) an antibody or antigen-binding fragment thereof provided herein, wherein the antibody or antigen-binding fragment thereof comprises a nucleic acid probe; and (b) a template oligonucleotide that is capable of binding to the nucleic acid probe. In embodiments, the invention provides a kit comprising an antibody or antigen-binding fragment provided herein, wherein the antibody or antigen-binding fragment thereof comprises a nucleic acid probe. In embodiments, the kit further comprises (i) a template oligonucleotide that is capable of binding to the nucleic acid probe, and (ii) a labeled probe comprising a detectable label, wherein the detectable label is an ECL label. In embodiments, the template oligonucleotide is a circular oligonucleotide template. In embodiments, the kit further comprises (iii) an anchoring reagent. In embodiments, the kit further comprises a nucleic acid amplification enzyme (e.g., a polymerase), a surface, a capture reagent, and/or a detection reagent.

In embodiments, the invention provides a composition comprising: (a) an antibody or antigen-binding fragment thereof provided herein, wherein the antibody or antigen-binding fragment thereof comprises an enzyme; and (b) a substrate of the enzyme. In embodiments, the invention provides a kit comprising the antibody or antigen-binding fragment provided herein, wherein the antibody or antigen-binding fragment thereof comprises an enzyme.

In embodiments, the invention provides a composition comprising an antibody or antigen-binding fragment thereof provided herein, wherein the antibody or antigen-binding fragment thereof comprises a detectable label. In embodiments, the invention provides a kit comprising the antibody or antigen-binding fragment provided herein, wherein the antibody or antigen-binding fragment thereof comprises a detectable label.

In embodiments, the invention provides a composition comprising: (a) an antibody or antigen-binding fragment thereof provided herein, wherein the antibody or antigen-binding fragment thereof comprises a binding moiety; and (b) a detectable moiety comprising (i) a binding partner of the binding moiety and (ii) one or more detectable labels. In embodiments, the invention provides a kit comprising the antibody or antigen-binding fragment provided herein, wherein the antibody or antigen-binding fragment thereof comprises a binding moiety.

In embodiments, the invention provides an assay system comprising: at least one memory unit; at least one processing unit programmed according to instructions on the at least one memory unit; and at least one assay system component configured to be controlled by the at least one processing unit, wherein the at least one processing unit is configured to: control the at least one assay system component to perform one or both of: a first measurement of a higher abundance analyte in a sample; and a second measurement of a lower abundance analyte in the sample, wherein the higher abundance analyte is present in the sample at approximately 10 to 100000 higher-fold than the lower abundance analyte, wherein the higher abundance analyte is detected using a detection reagent comprising an ECL label, and wherein the lower abundance analyte is detected using (i) a detection reagent comprising an ECL label and (ii) a signal amplification reagent that specifically binds to the ECL label.

In embodiments, the invention provides one or more non-transitory computer-readable media having instructions stored thereon that, when executed by at least one processing unit, cause the at least one processing unit to: perform, via control of an assay system, one or both of: a first measurement of a higher abundance analyte in a sample; and a second measurement of a lower abundance analyte in the sample, wherein the higher abundance analyte is present in the sample at approximately 10 to 100000 higher-fold than the lower abundance analyte, wherein the higher abundance analyte is detected using a detection reagent comprising an ECL label, and wherein the lower abundance analyte is detected using (i) a detection reagent comprising an ECL label and (ii) a signal amplification reagent that specifically binds to the ECL label.

In embodiments, the invention provides an assay system comprising: at least one memory unit; at least one processing unit programmed according to instructions on the at least one memory unit; and at least one assay system component configured to be controlled by the at least one processing unit, wherein the at least one processing unit is configured to: control the at least one assay system component to perform a measurement of an analyte in a sample, wherein the analyte is capable of being detected in the sample when present at a concentration within 0.0001 to 100000 pg/mL using a single detection reagent comprising an ECL label.

BRIEF DESCRIPTION OF THE DRAWINGS

The following drawings form part of the present specification and are included to further demonstrate exemplary embodiments of certain aspects of the present invention.

In FIG. 1A, a first complex comprising a capture reagent, an analyte, and a detection reagent with multiple first detectable labels is formed on a surface. The capture reagent is immobilized to the surface via the binding of the targeting agent complement on the capture reagent to the targeting agent on the surface. A signal amplification reagent comprising a nucleic acid probe ("Sig. Amp. Reagent with nucleic acid probe") is added to the first complex, thereby forming a second complex. The detection reagent comprises multiple first detectable labels, allowing multiple signal amplification reagents to bind to each detection reagent. In embodiments, the nucleic acid probe of each signal amplification reagent is amplified using the methods described herein. FIG. 1B shows the second complex comprising the capture reagent ("CR"), analyte, detection reagent ("DR") comprising the first detectable label ("$1^{ST}$ Label"), and signal amplification reagent ("SAR") comprising the nucleic acid probe, wherein the nucleic acid probe is extended to form an extended sequence ("extended seq") via a template oligonucleotide ("template oligo"), and a labeled probe is bound to the extended sequence. FIG. 1C shows a further embodiment wherein the detection reagent comprises three first detectable labels, each bound to a first signal amplification reagent that comprises an extended sequence bound to two labeled probes. FIG. 1D shows a further embodiment in which a detection reagent comprises two first detectable labels, wherein each detectable label is bound to a signal amplification reagent comprising a nucleic acid probe, and two template oligonucleotides are hybridized to the two nucleic acid probes, wherein each template oligonucleotide hybridizes to both nucleic acid probes. In embodiments, the two template oligonucleotides are capable of being ligated together to form a circular template.

FIG. 6 shows the results of exemplary immunoassays for screening eleven anti-SULFO-TAG antibody clones as signal amplification reagent. The analytes for the immunoassays were human ZnT8, human IA-2, human TGM-2, or mouse IL-1b. The measured ECL assay signals for each anti-SULFO-TAG antibody in each analyte-specific immunoassay are shown.

FIG. 7 shows the results of an exemplary calibrator titration immunoassay with human ZnT8 as the analyte using six different anti-SULFO-TAG antibody clones as signal amplification reagents. The measured ECL signals with seven different concentrations of human ZnT8 calibrator (numbered as STD 01 to STD 07) and a blank (STD 08) are shown. Hill slope, R squared value, lowest limit of detection (LLOD), signal-to-background ratio (SB) for STD 04 (based on STD 04/STD 08 value), and signal-to-noise ratio (S/N) for STD 04 (based on STD 04/STD 08 value) are shown.

FIG. 8 shows the results of an exemplary calibrator titration immunoassay with human TGM-2 as the analyte using six different anti-SULFO-TAG antibody clones as signal amplification reagents. The measured ECL signals with seven different concentrations of human TGM-2 calibrator (numbered as STD 01 to STD 07) and a blank (STD 08) are shown. Hill slope, R squared value, lowest limit of detection (LLOD), signal-to-background ratio (S/B) for STD 04 (based on STD 04/STD 08 value), and signal-to-noise ratio (S/N) for STD 04 (based on STD 04/STD 08 value) are shown.

FIG. 9 shows the results of exemplary calibration titration immunoassays using the same human ZnT8 and TGM-2 calibrators as shown in FIGS. 7 and 8, but the immunoassays were performed without an anti-SULFO-TAG as signal amplification reagent. The measured ECL signals, Hill slope, R squared value, lowest limit of detection (LLOD), signal-to-background ratio (S/B) for STD 04 (based on STD 04/STD 08 value), and signal-to-noise ratio (S/N) for STD 04 (based on STD 04/STD 08 value) are shown.

FIG. 10 shows the results of exemplary calibrator titration immunoassay with mouse IL-23 as the analyte using six different anti-SULFO-TAG antibody clones as signal amplification reagents. The measured ECL signals with three different concentrations of mouse IL-23 calibrator (numbered as STD 01 to STD 03) and a blank (STD 04) are shown. Hill slope, R squared value, lowest limit of detection (LLOD), signal-to-background ratio (S/B) for STD 02

(based on STD 02/STD 04 value), and signal-to-noise ratio (S/N) for STD 02 (based on STD 02/STD 04 value) are shown.

FIG. 11 shows the results of exemplary calibrator titration immunoassay with mouse IL-17C as the analyte using six different anti-SULFO-TAG antibody clones as signal amplification reagents. The measured ECL signals with three different concentrations of mouse IL-17C calibrator (numbered as STD 01 to STD 03) and a blank (STD 04) are shown. Hill slope, R squared value, lowest limit of detection (LLOD), signal-to-background ratio (S/B) for STD 02 (based on STD 02/STD 04 value), and signal-to-noise ratio (S/N) for STD 02 (based on STD 02/STD 04 value) are shown.

FIG. 12 shows the results of exemplary calibration titration immunoassays using the same mouse IL-23 and IL-17C calibrators as shown in FIGS. 10 and 11, but the immunoassays were performed without an anti-SULFO-TAG as signal amplification reagent. The measured ECL signals and lowest limit of detection (LLOD) are shown.

FIG. 13 shows the results of exemplary calibrator titration immunoassay with human IL-10 as the analyte using six different anti-SULFO-TAG antibody clones as signal amplification reagents. The measured ECL signals with three different concentrations of human IL-10 calibrator (numbered as STD 01 to STD 03) and a blank (STD 04) are shown. Hill slope, R squared value, lowest limit of detection (LLOD), signal-to-background ratio (S/B) for STD 02 (based on STD 02/STD 04 value), and signal-to-noise ratio (S/N) for STD 02 (based on STD 02/STD 04 value) are shown.

FIG. 14 shows the results of exemplary calibration titration immunoassays using the same human IL-10 calibrators as shown in FIG. 13, but the immunoassays were performed without an anti-SULFO-TAG as signal amplification reagent. The measured ECL signals and lowest limit of detection (LLOD) are shown.

Figure 15:
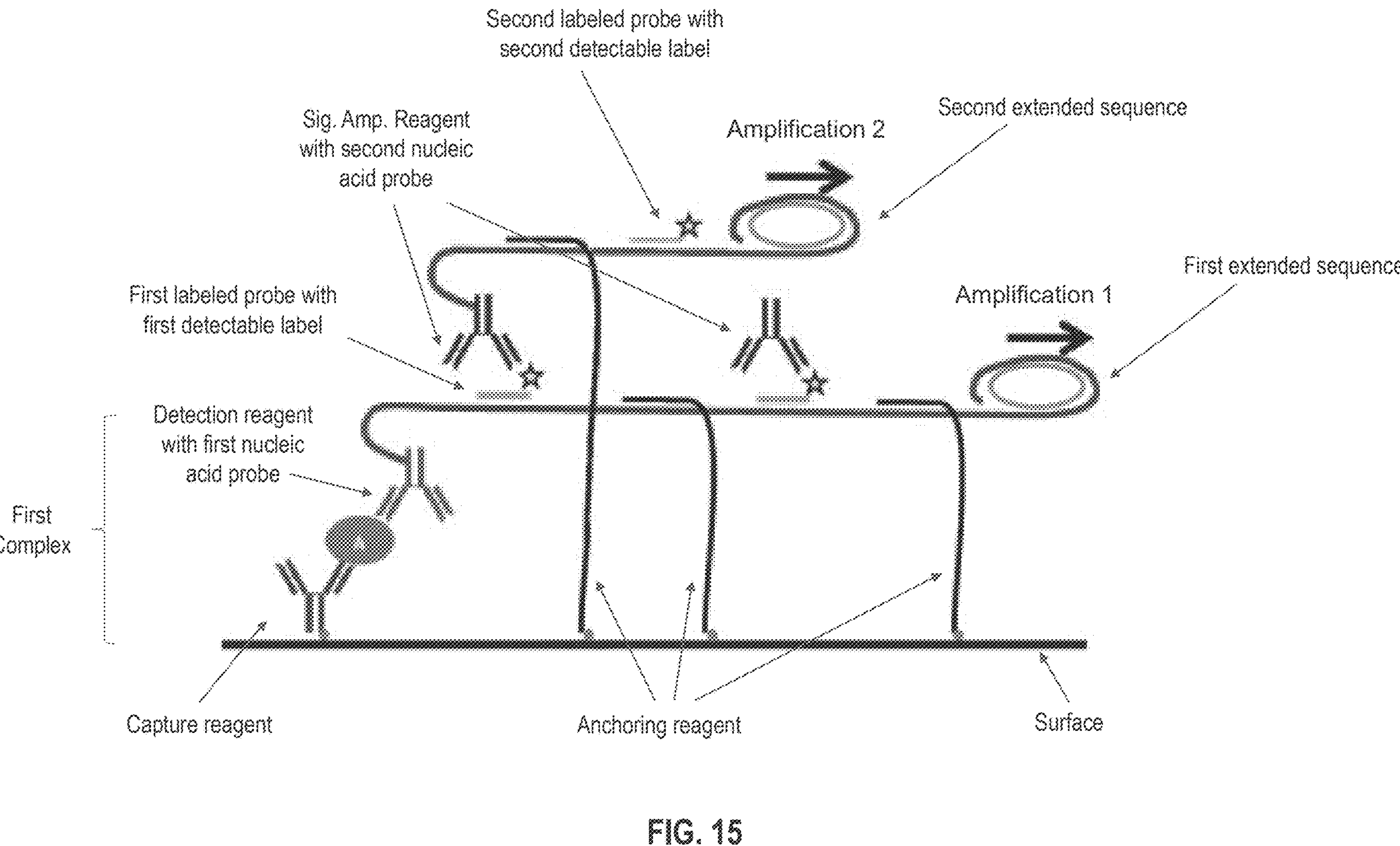

FIG. 15 illustrates an embodiment of the methods described herein. A first complex comprising a capture reagent, an analyte, and a detection reagent with a first nucleic acid probe is formed on a surface. The first nucleic acid probe is extended ("Amplification 1") to form a first extended sequence. A plurality of first labeled probes, each comprising a first detectable label, binds to the first extended sequence. Multiple signal amplification reagents, each comprising a second nucleic acid probe, bind to the first detectable labels. Each of the second nucleic acid probes is extended ("Amplification 2") to form a second extended sequence. One or more second labeled probes, each comprising a second detectable label, binds to the second extended sequence.

FIGS. 16A-16C show the results of exemplary assays performed to measure the signal inhibition and signal enhancement of the anti-SULFO-TAG antibody clones shown in FIG. 6. FIG. 16A shows the percent (%) signal inhibition and % signal increase for each of the anti-SULFO-TAG antibody clones. FIG. 16B shows a bar graph plot of the % signal inhibition for each of the antibody clones. FIG. 16B shows a bar graph plot of the % signal increase for each of the antibody clones.

Figure 17:
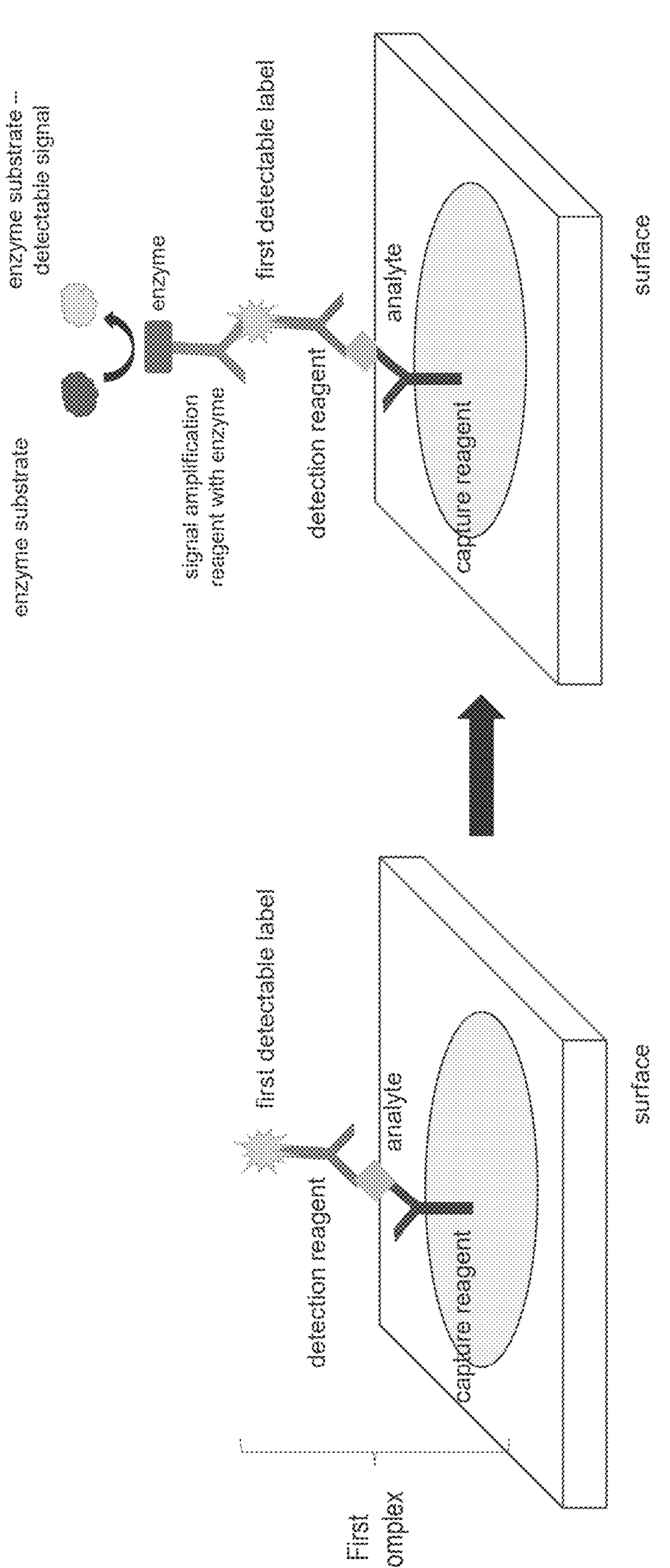

FIG. 17 shows an embodiment of the methods described herein. A first complex comprising a capture reagent, an analyte, and a detection reagent with a first detectable label is on a surface. A signal amplification reagent comprising an enzyme and enzyme substrate are added to the first complex in one or more steps. The enzyme acts upon the substrate to produce a detectable signal.

Figures 18A, 18B:
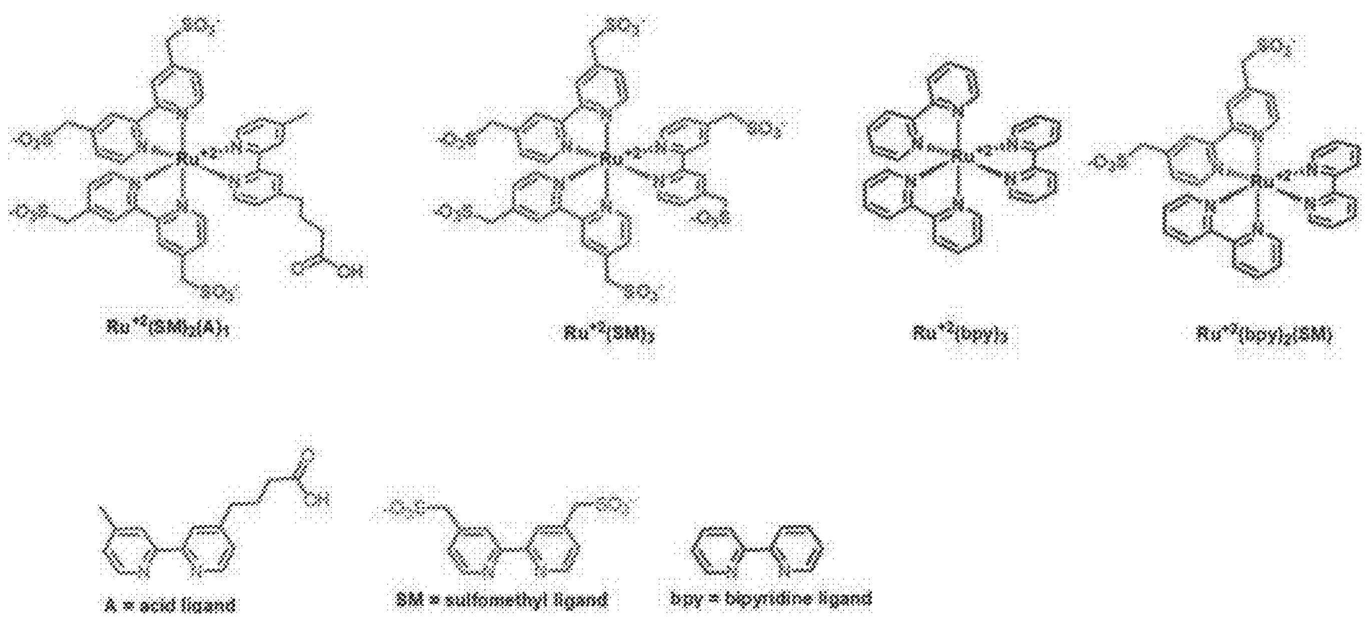

FIG. 18A shows exemplary organometallic $Ru^{2+}$ compounds ("TAG compounds") with varying numbers of sulfo-methyl-bipyridine ("SM"), bipyridine ("Bpy"), or acid ("A") ligands. FIG. 18B shows the ECL generation ability from the exemplary TAG compounds.

Figure 19A:
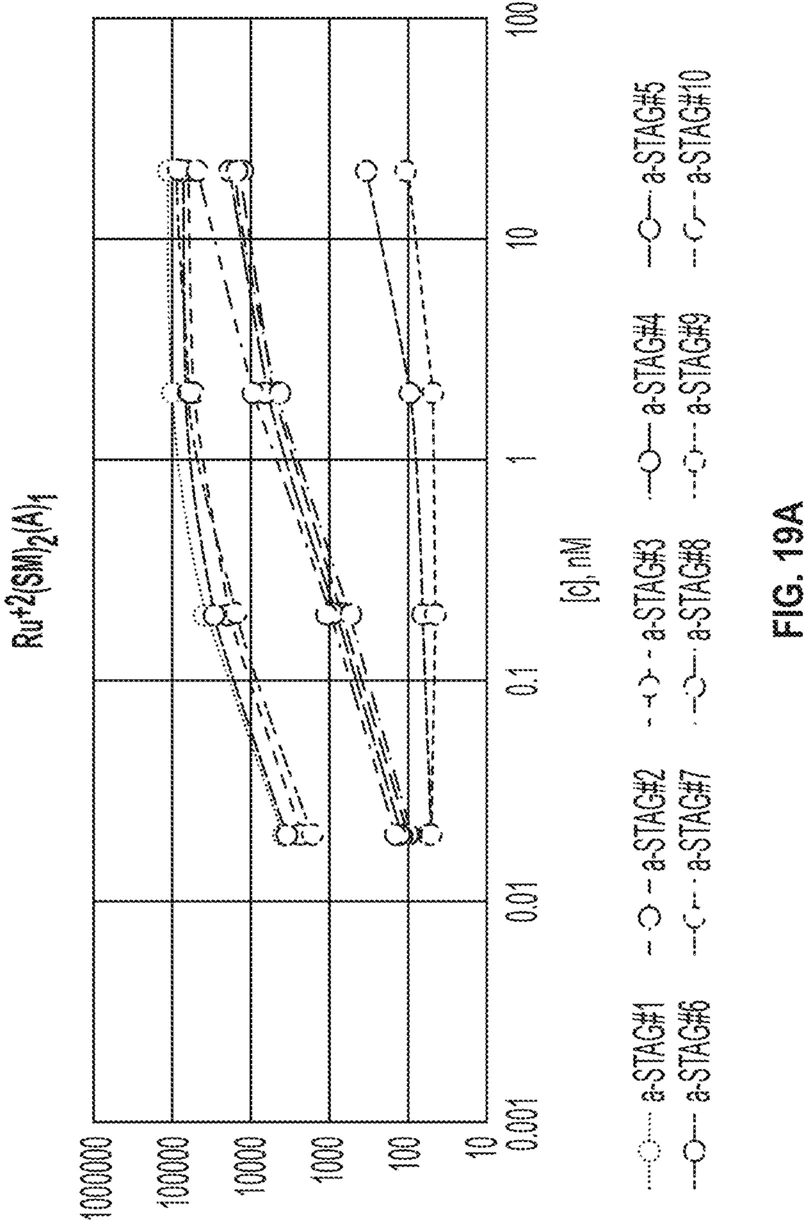
Figure 19B:
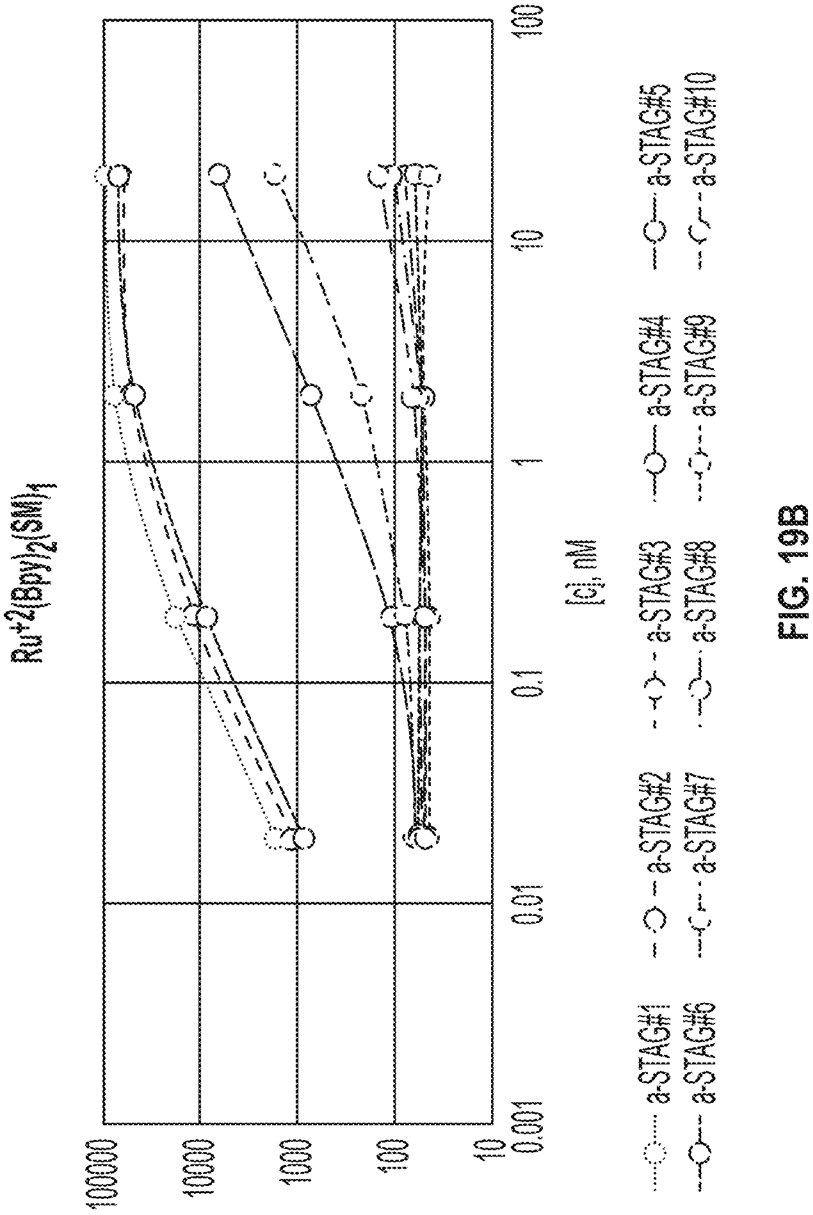
Figure 19C:
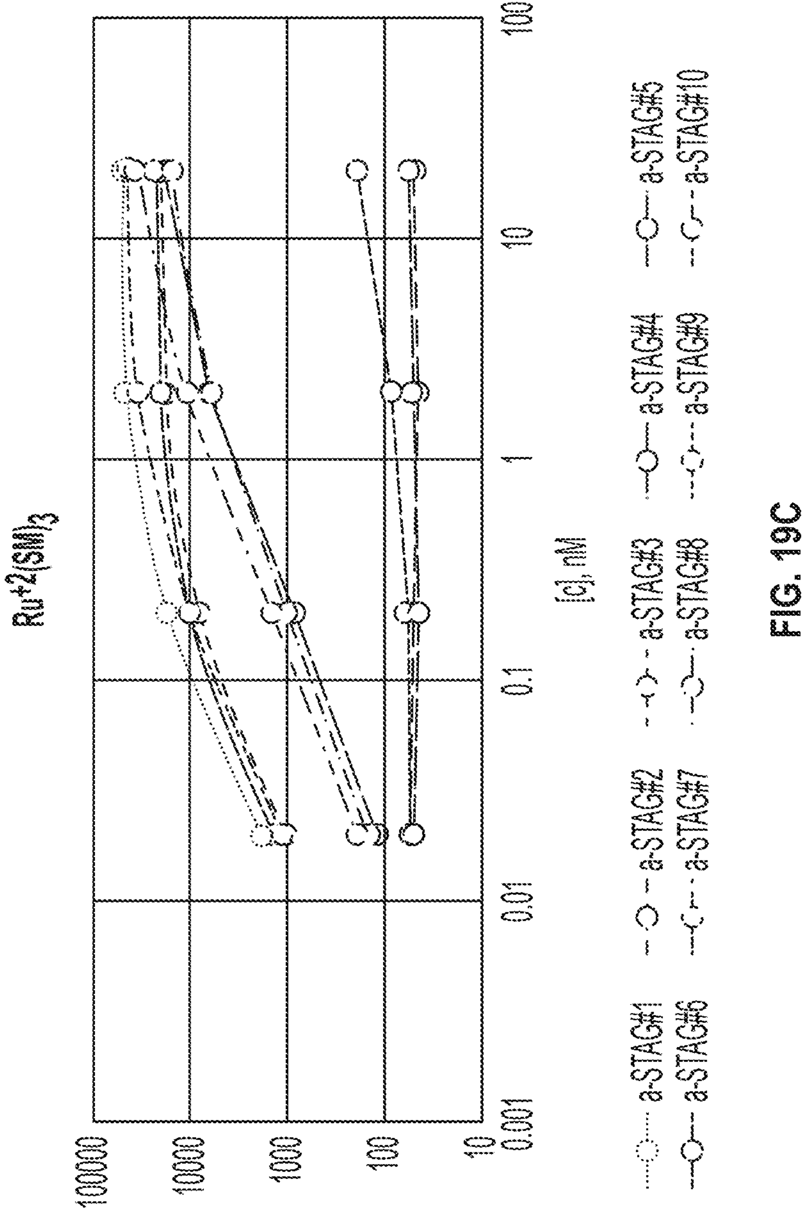
Figure 19D:
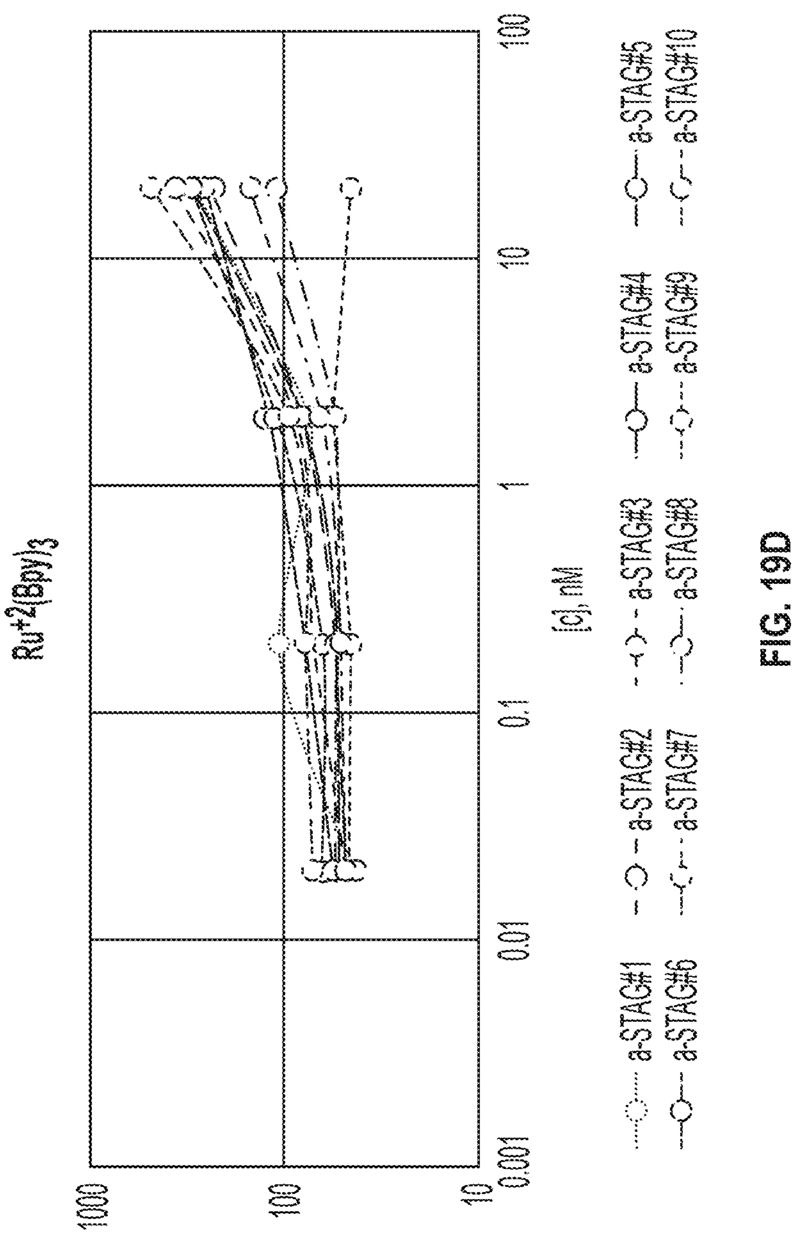
Figure 19E:
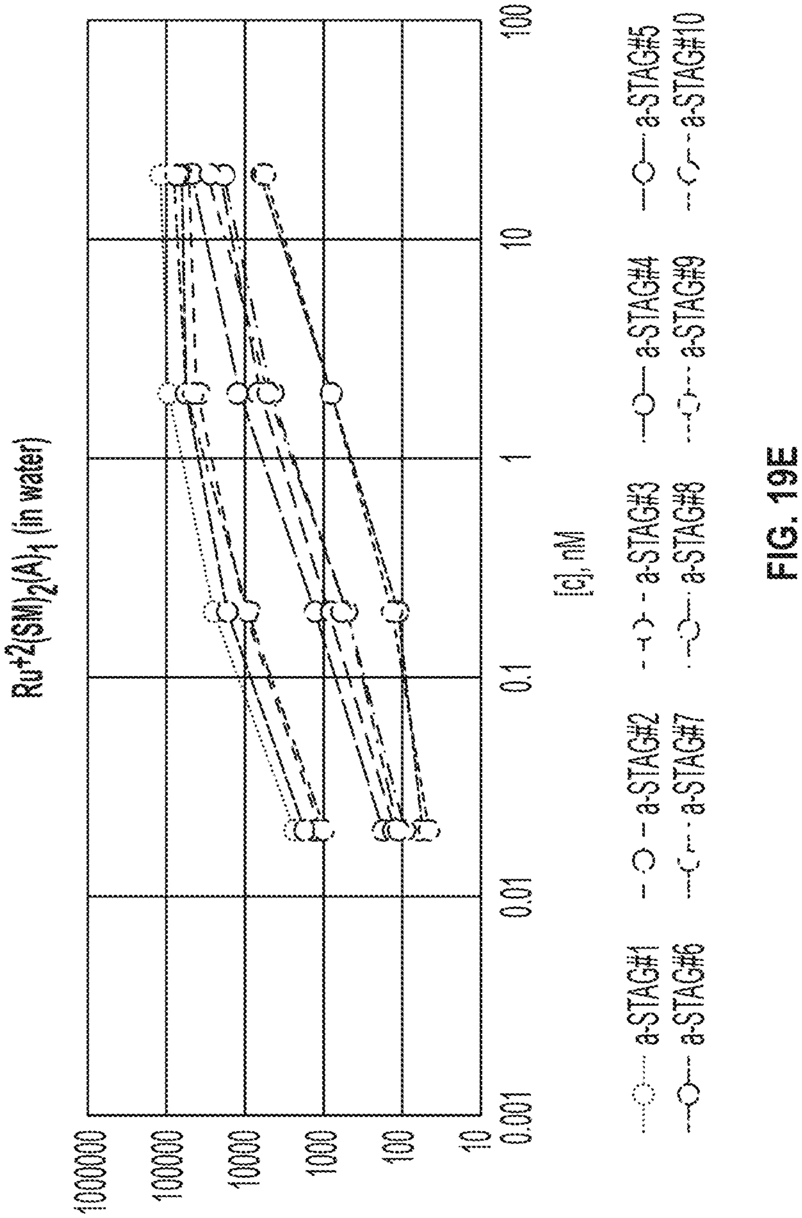
Figure 19F:
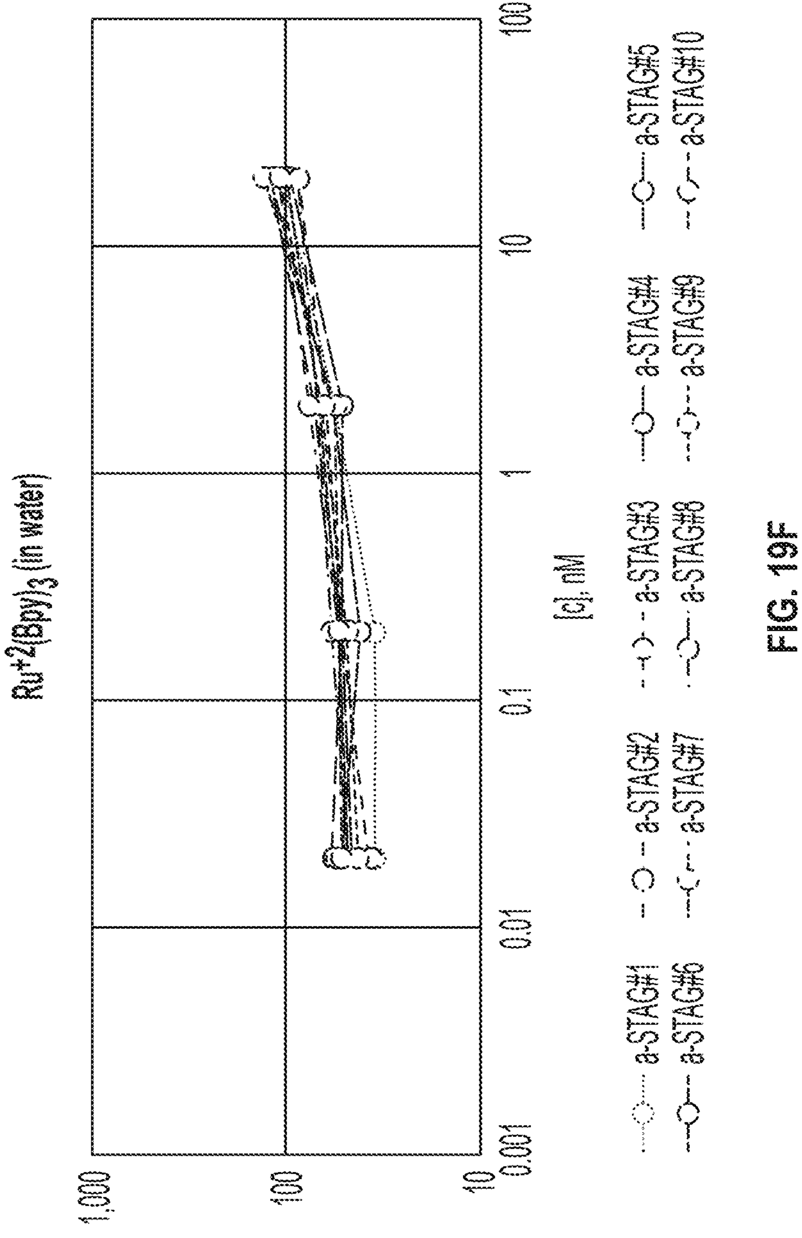
Figure 19G:
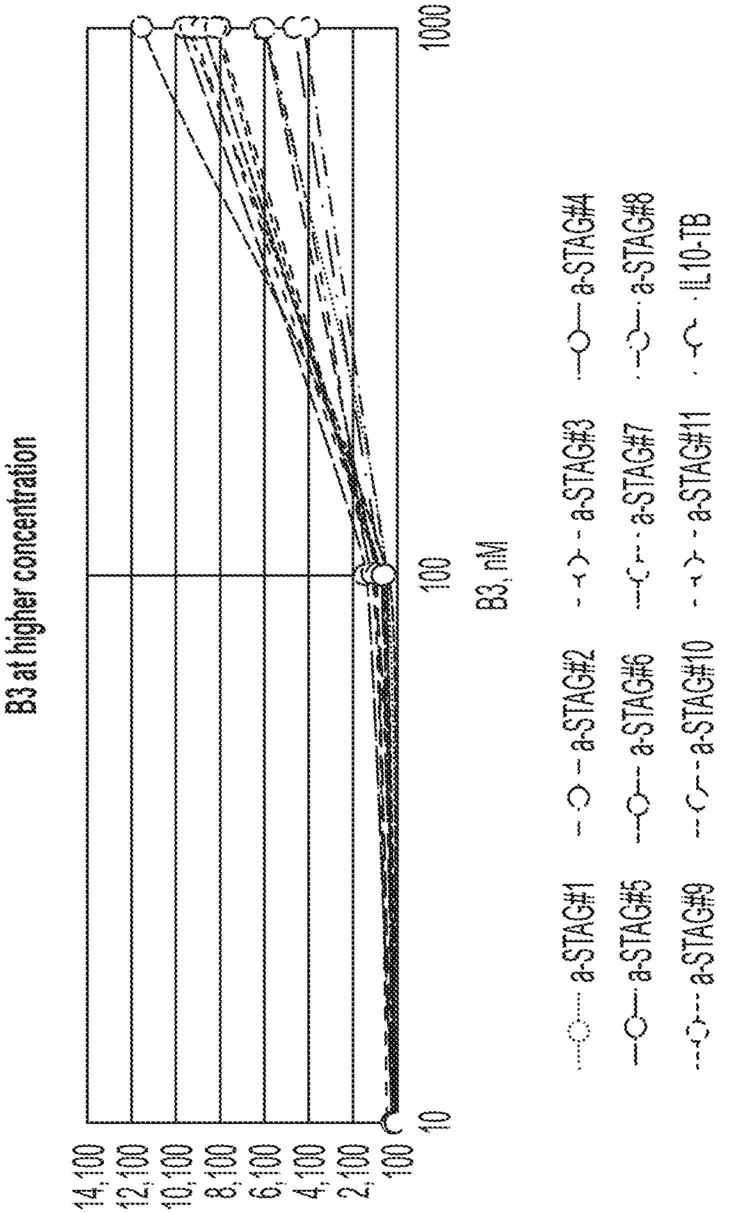
Figure 20A:
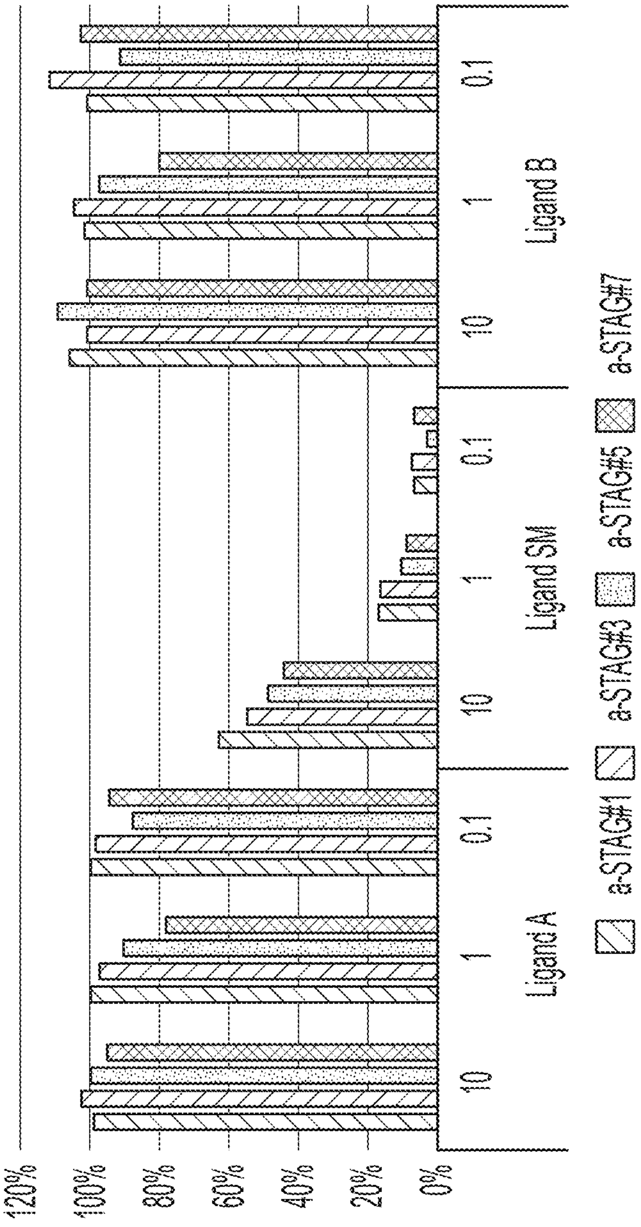
Figure 20B:
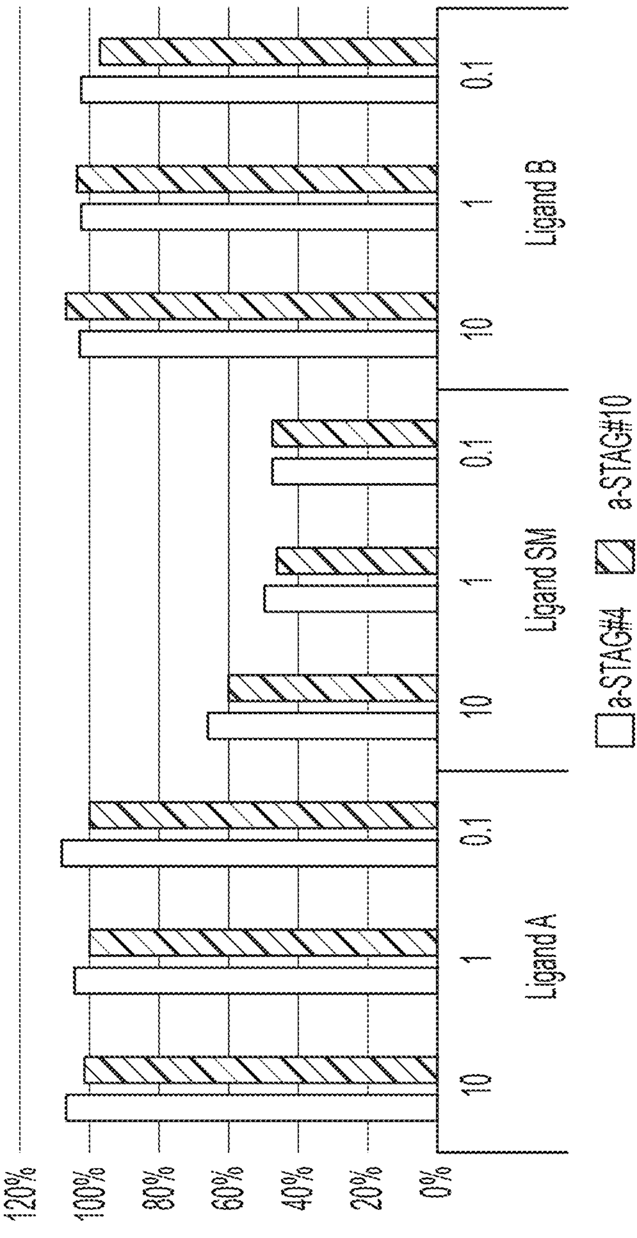
Figure 20C:
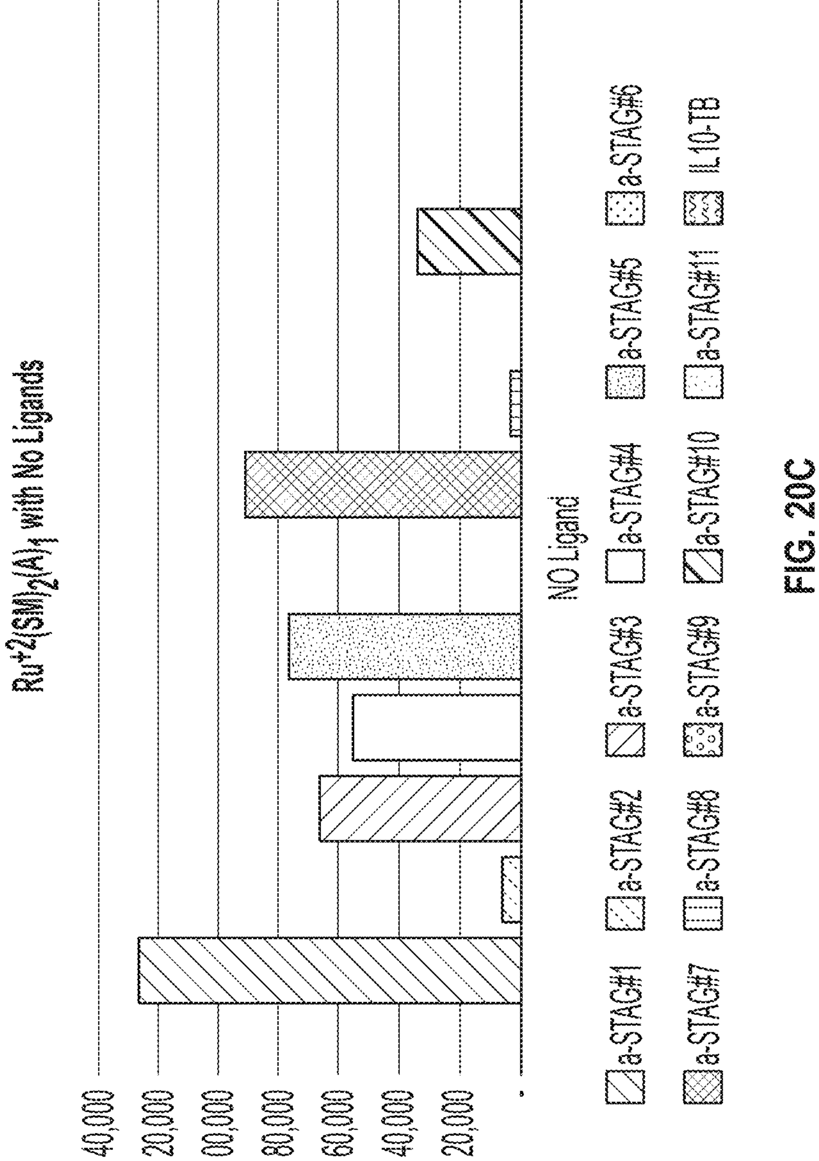
Figure 20D:
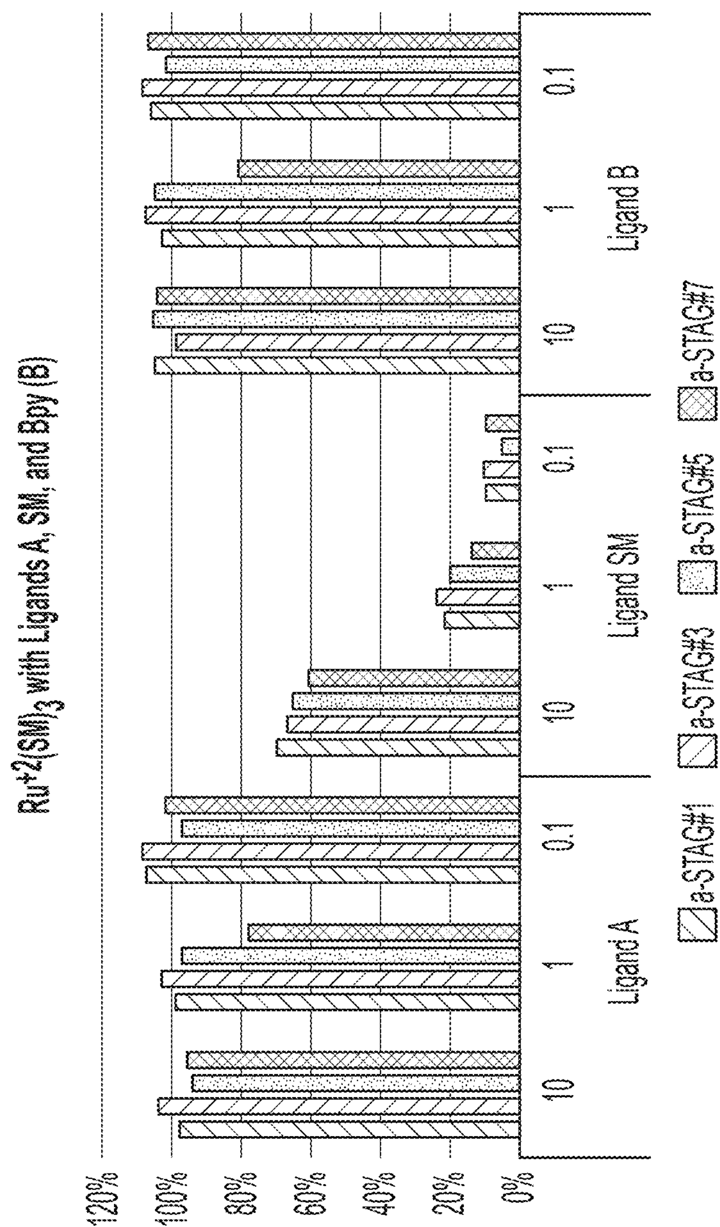
Figure 20E:
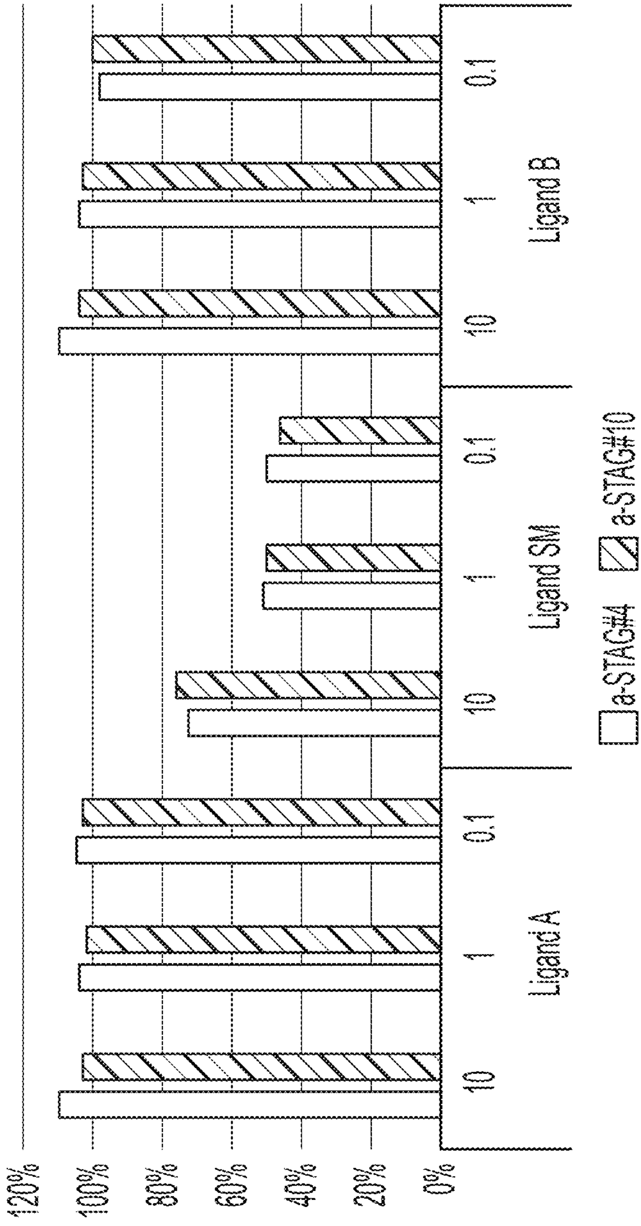
Figure 20F:
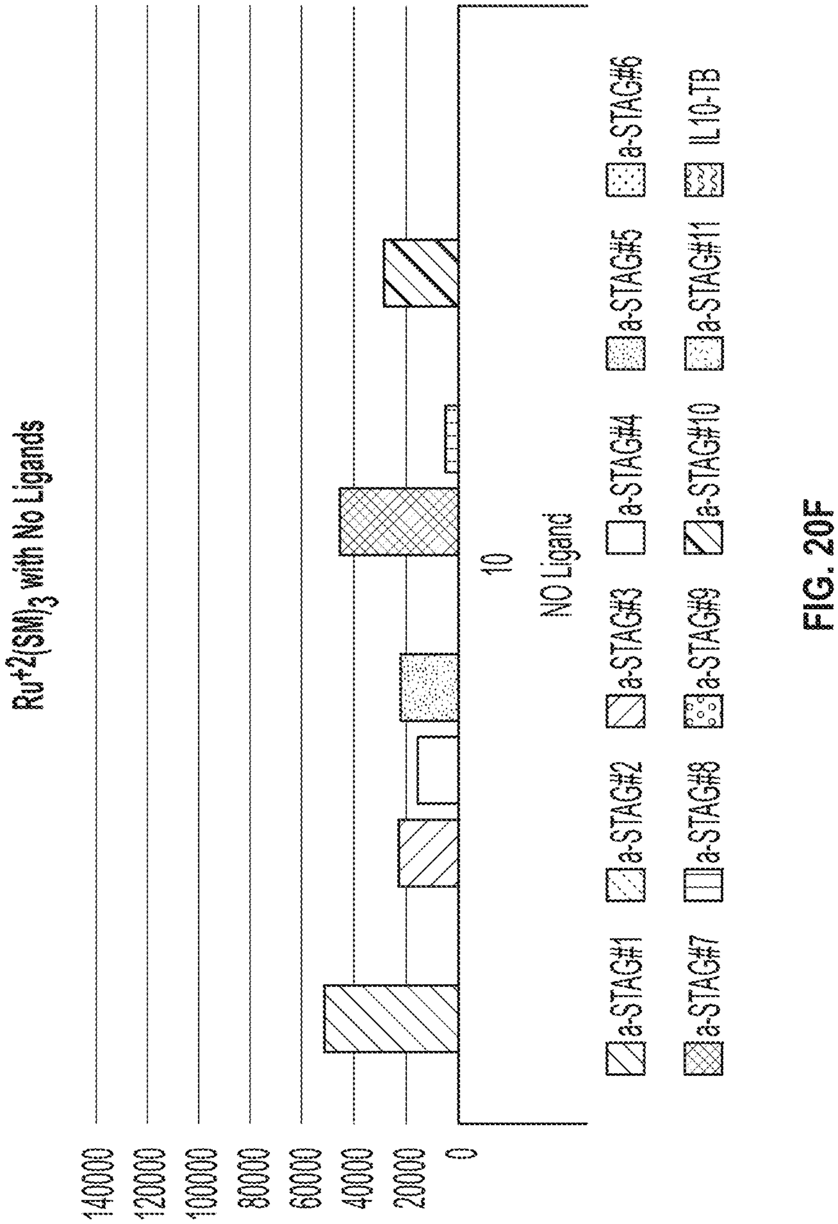
Figure 20G:
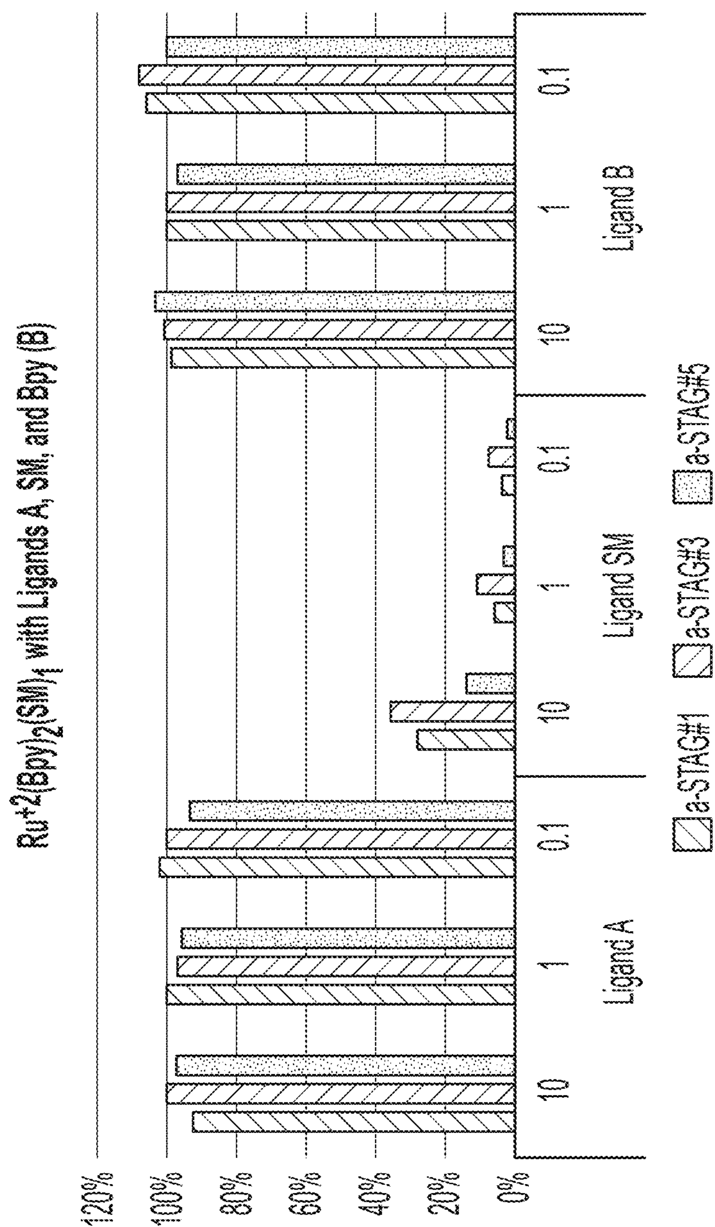
Figure 20H:
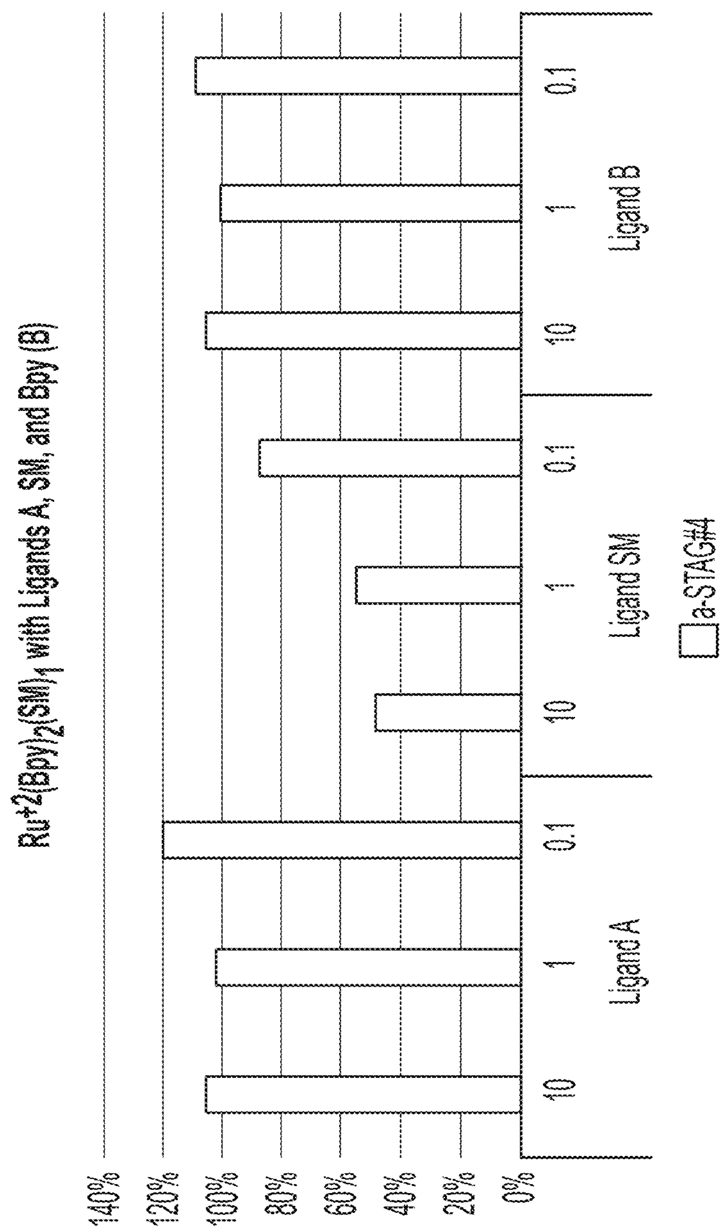
Figure 20I:
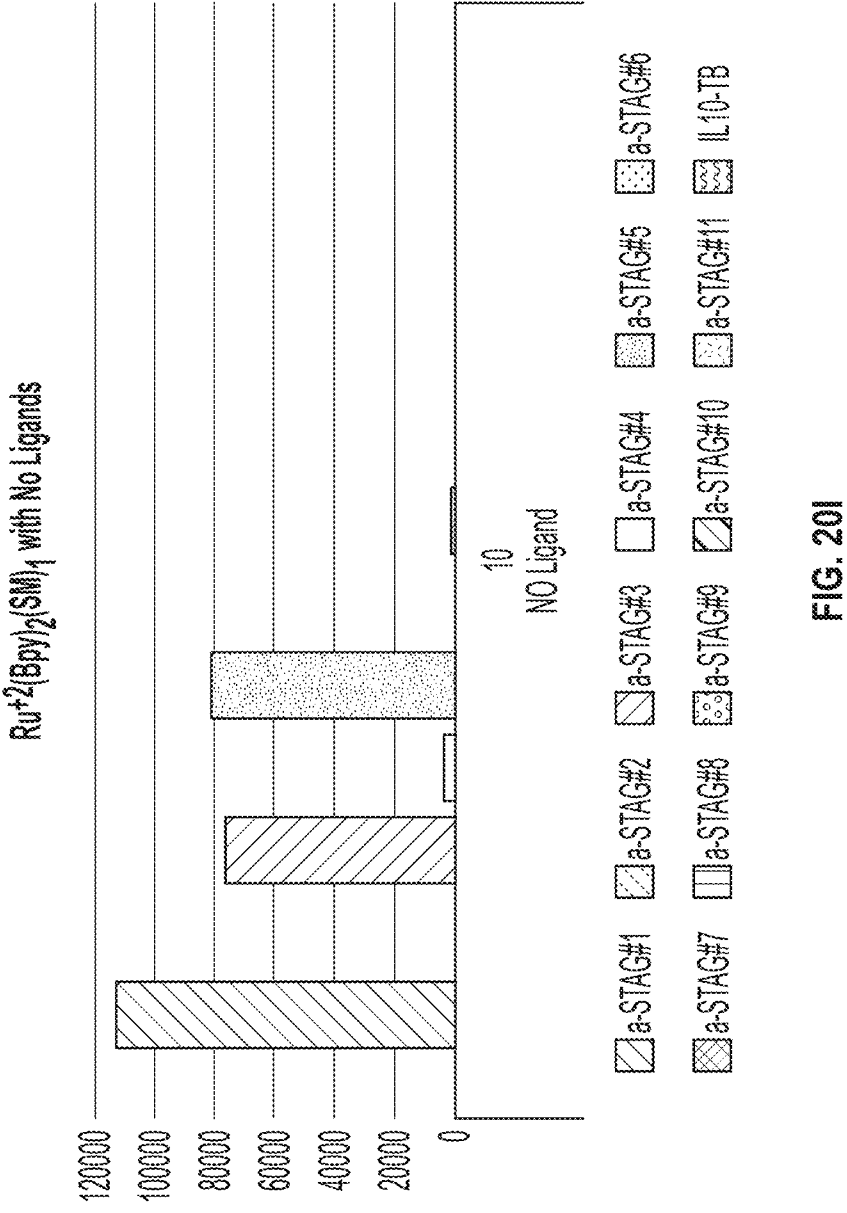

FIGS. 19A-19F show the results of exemplary binding assays with TAG the compounds shown in FIG. 18A and the anti-SULFO-TAG antibody clones described in Example 4. ECL signal from the anti-SULFO-TAG antibodies were measured, with higher signal indicative of stronger binding affinity. FIG. 19G shows antibody binding to the $Ru^{+2}(Bpy)_3$ compound at higher concentration (from 10 to 1000 nM).

FIGS. 20A-20I show the results of exemplary competitive binding assays between the TAG compounds shown in FIG. 18A and the SM, Bpy, or A ligands shown in FIG. 18A, with the anti-SULFO-TAG antibody clones described in Example 4. The graphs show the remaining ECL signal after anti-SULFO-TAG antibodies were exposed to 2 μM of each ligand, then varying concentrations of each of the TAG compounds. Lower ECL signal is indicative of stronger binding affinity to a particular ligand. The three panels in the right-most column show ECL signals from exposing the anti-SULFO-TAG antibody clones to 10 nM of the TAG compounds alone (without ligands).

Figure 21:
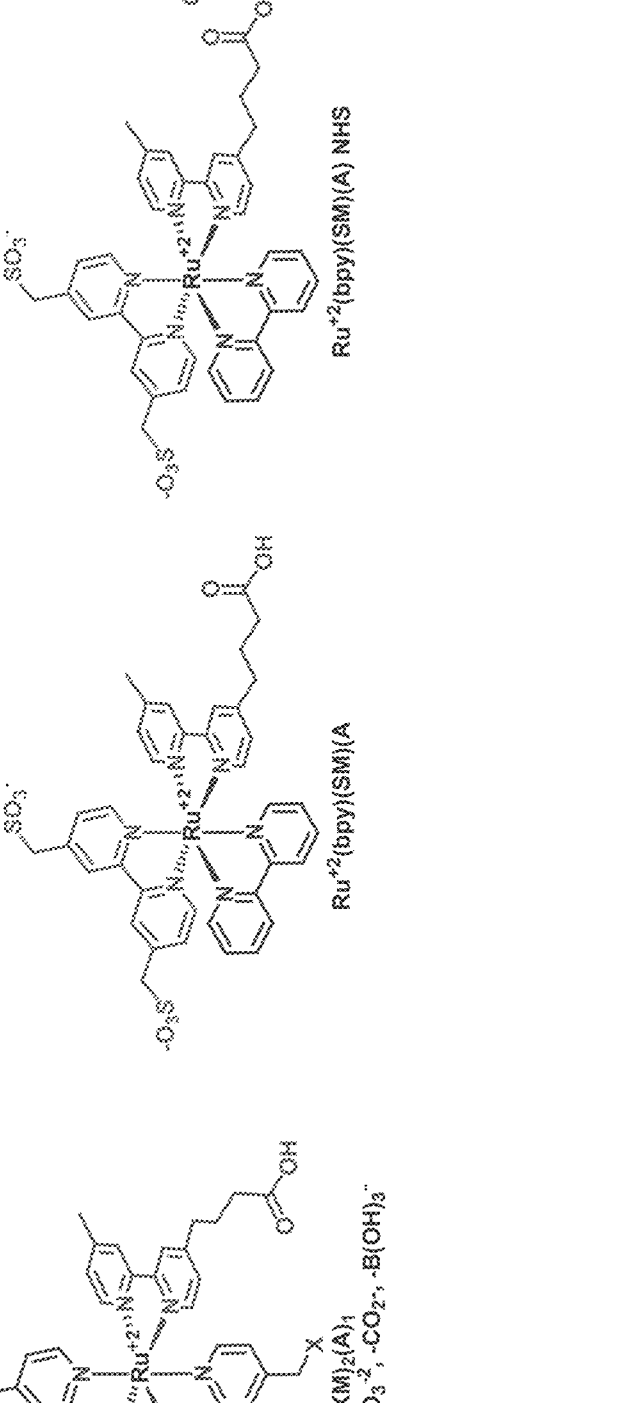

FIG. 21 shows exemplary organometallic $Ru^{2+}$ compounds that contain different charged functional groups as substituents on the bipyridine ligands.

Figures 22A, 22B, 22C, 22D:
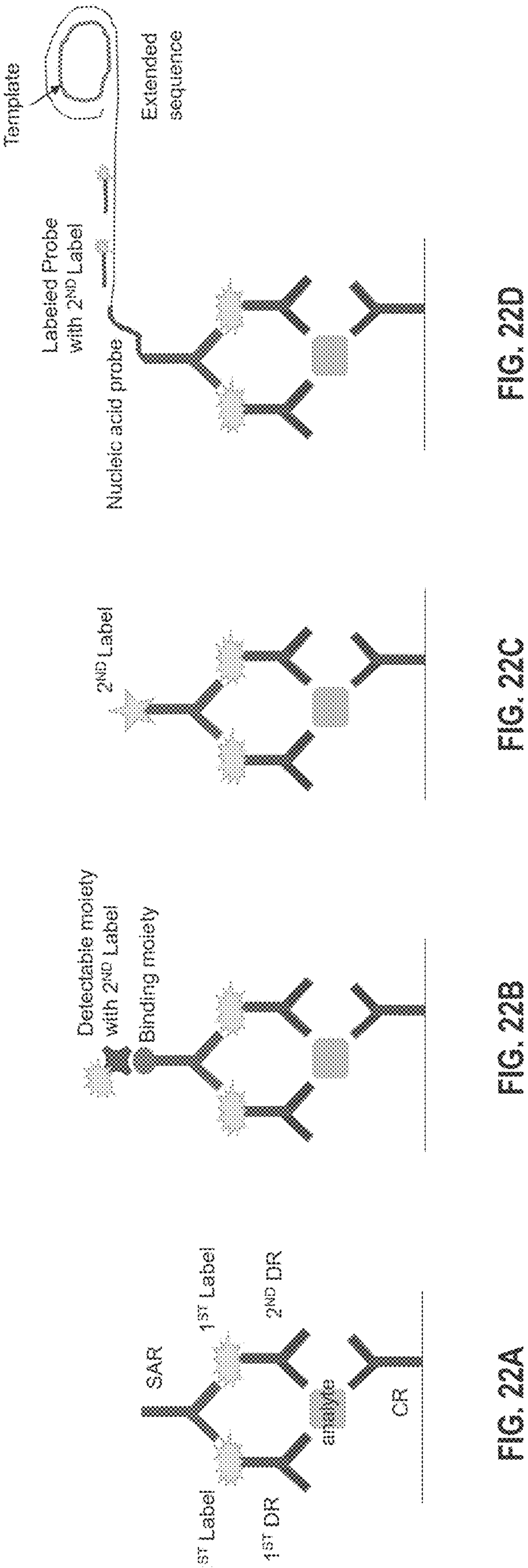

FIGS. 22A-22D show embodiments of the methods described herein. In each of FIGS. 22A-22D, a complex comprises a capture reagent ("CR"), an analyte, a first detection reagent ("$1^{ST}$ DR")) comprising a first detectable label ("$1^{ST}$ Label"), a second detection reagent ("$2^{ND}$ DR") comprising a first detectable label, a signal amplification reagent ("SAR") that binds simultaneously to the first detectable label on the first detection reagent and the first detectable label on the second detection reagent. In FIG. 22A, the signal amplification reagent is depicted without any other component. The components as labeled in FIG. 22A are the same as for FIGS. 22B-22D. In FIG. 22B, the signal amplification reagent comprises a binding moiety that binds to a detectable moiety comprising a binding partner of the binding moiety and a second detectable label as described herein. In FIG. 22C, the signal amplification reagent comprises a second detectable label as described herein. In FIG. 22D, the signal amplification reagent comprises a nucleic acid probe, which is extended via a template oligonucleotide to form an extended sequence that binds to one or more labeled probes comprising a second detectable label, as described herein.

DETAILED DESCRIPTION OF THE INVENTION

Unless otherwise defined herein, scientific and technical terms used in the present disclosure shall have the meanings that are commonly understood by one of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

The use of the term "or" in the claims is used to mean "and/or," unless explicitly indicated to refer only to alternatives or the alternatives are mutually exclusive, although the disclosure supports a definition that refers to only alternatives and "and/or."

As used herein, the terms "comprising" (and any variant or form of comprising, such as "comprise" and "comprises"), "having" (and any variant or form of having, such as "have" and "has"), "including" (and any variant or form of including, such as "includes" and "include") or "containing" (and any variant or form of containing, such as "contains" and "contain") are inclusive or open-ended and do not exclude additional, unrecited, elements or method steps.

The use of the term "for example" and its corresponding abbreviation "e.g." (whether italicized or not) means that the specific terms recited are representative examples and embodiments of the disclosure that are not intended to be limited to the specific examples referenced or cited unless explicitly stated otherwise.

As used herein, "between" is a range inclusive of the ends of the range. For example, a number between x and y explicitly includes the numbers x and y, and any numbers that fall within x and y.

The invention provides several advantages over assay methods described in the art. For example, the invention provides a simple and convenient method to increase the detectable signal in an assay, enabling the detectable label to be measured using lower cost and/or lower complexity instrumentation. This increase in signal may also, for example, provide a simple and convenient method to improve the sensitivity of an assay by amplifying a detectable signal. In embodiments, the methods herein improve the signal-to-noise ratio and enables more accurate detection, e.g., of low abundance species in a sample.

In embodiments, the methods herein utilize a signal amplification reagent that specifically binds to a detectable label, e.g., an ECL label, that may already be employed in commercially available immunoassays. Current commercially available immunoassays can require different detection reagents for the same analyte, depending on the concentration of the analyte in the sample. For example, a detection reagent that comprises a detectable label can be used when analyte concentration is relatively high (e.g., greater than or about 1 pg/mL), while a detection reagent that comprises a nucleic acid probe can be used when analyte concentration is relatively low (e.g., less than about 1 pg/mL). Current commercial immunoassays can also require different assay formats and/or require a sample to be diluted or concentrated when measuring multiple analytes that are present in a sample at different concentrations. In embodiments, the inventive methods use a signal amplification reagent to amplify assay signal when analyte concentration is low, thereby eliminating the requirement for using multiple types of detection reagents, performing assays in different formats for different analyte concentrations, and/or concentrating or diluting the sample for measuring different analytes in the sample. In embodiments, for each first detectable label bound by the signal amplification reagent, the signal amplification reagent provides and/or recruits multiple second detectable labels, thereby amplifying the assay signal. In embodiments, the signal amplification reagent is capable of detecting an analyte that is present at a low concentration in the sample (e.g., less than 1 pg/mL), thereby allowing the sample to be diluted when sample supply is limited (e.g., cerebral spinal fluid samples, biological samples from infants, and/or biological samples from small animals such as mice), thus preserving valuable sample.

In embodiments, the signal amplification reagent comprises one or more detectable labels, e.g., ECL label(s); or the signal amplification reagent comprises or forms a moiety, e.g., a binding moiety described herein, that recruits binding of one or more detectable labels, e.g., ECL label(s). Thus, in embodiments, the signal amplification reagents described herein (1) specifically recognize and bind a first detectable label (e.g., on a detection reagent as described herein) and (2) are capable of recruiting one or more second detectable labels to amplify the assay signal. It was unexpectedly discovered that the signal amplification reagent provides surprisingly high levels of signal amplification even in embodiments where the first and second detectable labels are the same label. Under such circumstances, the second detectable label would be expected to compete with the first detectable label for the signal amplification reagent, i.e., a signal amplification reagent that binds to the second detectable label would not bind the first detectable label, as the signal amplification reagent has the same affinity for both the first and second detectable labels. The binding of the signal amplification reagent to the second detectable label was expected to prevent the second detectable label from being detected, and also prevent the signal amplification reagent from being a part of the complex on the surface, thereby resulting in loss of signal. Thus, the high levels of signal amplification, particularly in embodiments where the first and second detectable labels were the same label, were unexpected.

Figure 1A:
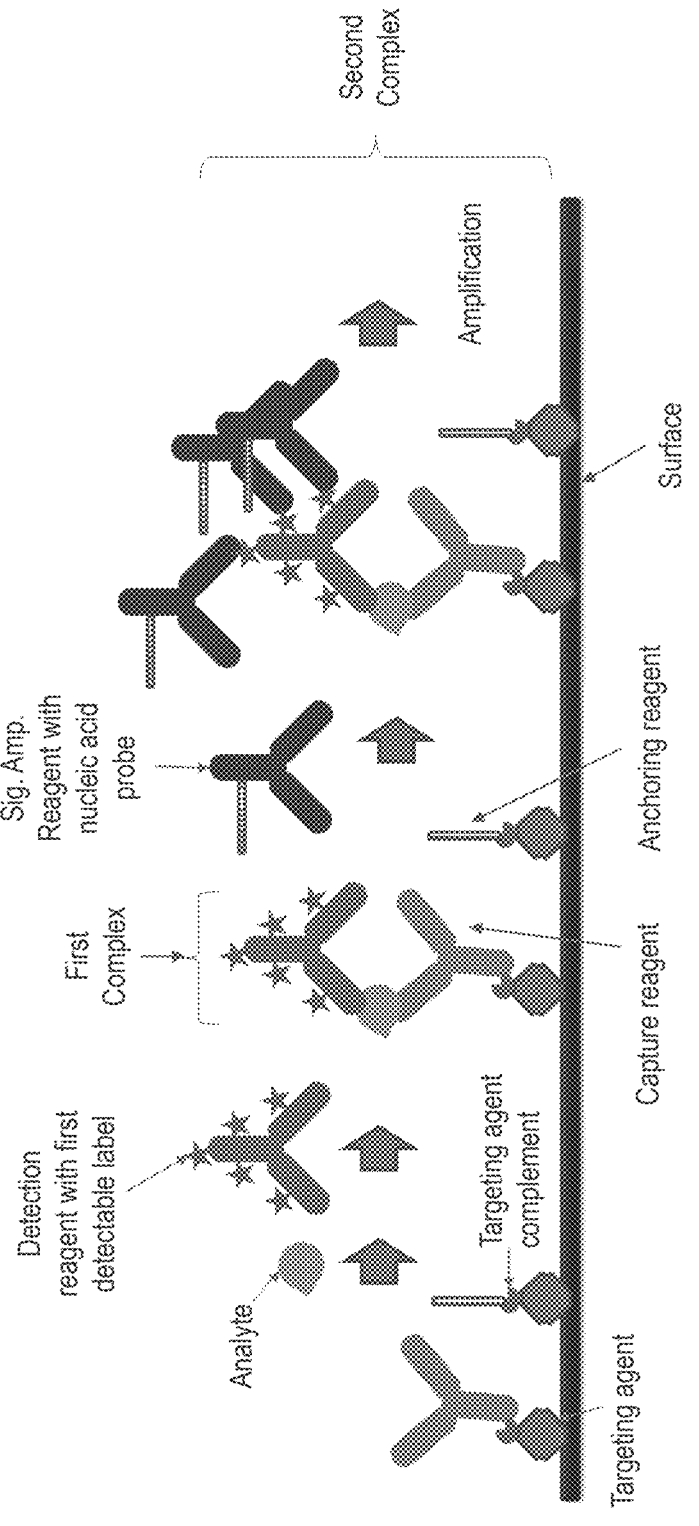
FIGS. 1A-1D illustrate embodiments of the methods described herein.
Figures 1B, 1C, 1D:
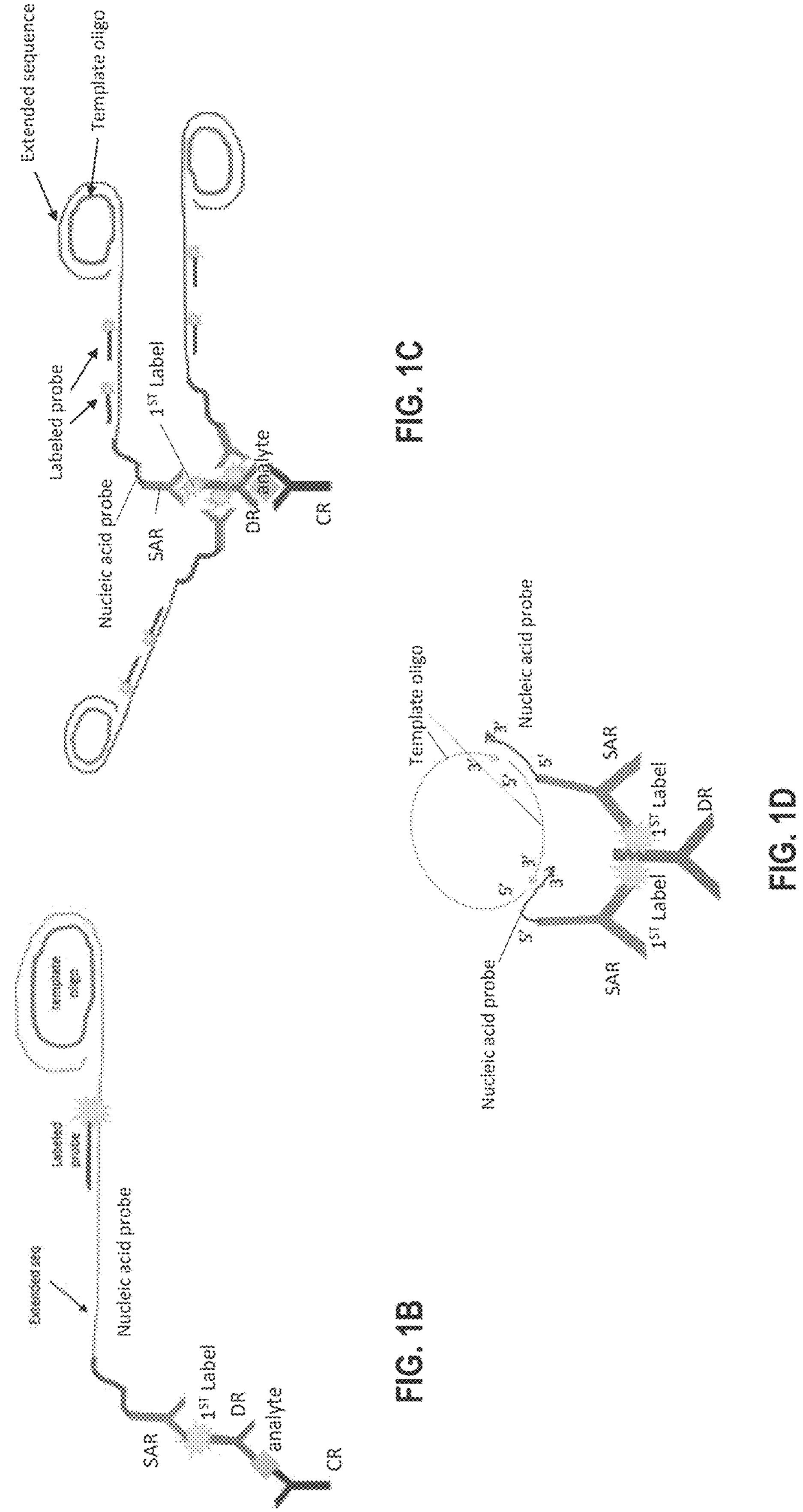

An embodiment of the method is illustrated in FIGS. 1A-1D. In FIG. 1A, a first complex comprising a capture reagent, an analyte, and a detection reagent with multiple first detectable labels is formed on a surface. The capture reagent is immobilized to the surface via the binding of the targeting agent complement on the capture reagent to the targeting agent on the surface. A signal amplification reagent comprising a nucleic acid probe is added to the first complex, thereby forming a second complex comprising the capture reagent, analyte, detection reagent, and signal amplification reagent as shown in FIG. 1B. In embodiments, the detection reagent comprises multiple first detectable labels, thereby allowing multiple signal amplification reagents to bind to the same detection reagent as shown in FIGS. 1A, 1C, and 1D. In embodiments, an extended sequence is formed from each signal amplification reagent bound to the detection reagent, as shown in FIGS. 1B and 1C. In embodiments, two signal amplification reagents, each comprising a nucleic acid probe, bind to two first detectable labels on the detection reagent. In embodiments, two template oligonucleotides are hybridized to the two nucleic acid probes, e.g., wherein each template oligonucleotide hybridizes to both nucleic acid probes as shown in FIG. 1D. In embodiments, the two template oligonucleotides form a circular template, e.g., through ligation, and one or both of the nucleic acid probes are extended to form an extended sequence. In embodiments, the extended sequence binds to the anchoring reagent on the surface. In embodiments, the anchoring reagent is immobilized to the surface, before, during, or after formation of the first complex. In embodiments, each extended sequence binds to multiple labeled probes (e.g., as shown in FIG. 1C), each of which includes multiple second detectable labels. Thus, in embodiments, each first detectable label corresponds to multiple second detectable labels, thereby amplifying the signal for measurement. In embodiments, the first detectable label is an ECL label. In embodiments, the second detectable label is an ECL label.

Figure 2:
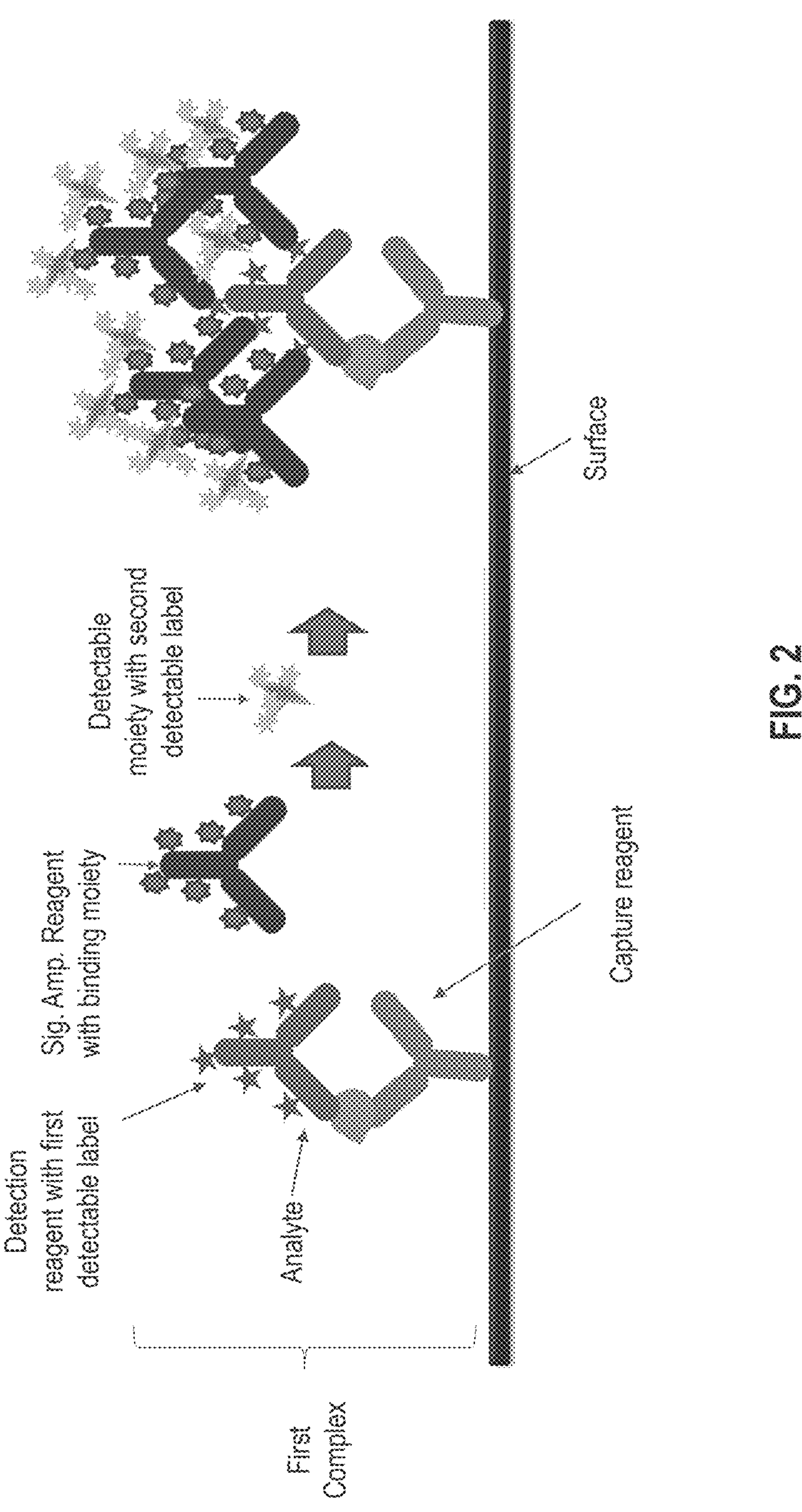
FIG. 2 illustrates an embodiment of the methods described herein. A first complex comprising a capture reagent, an analyte, and a detection reagent with multiple first detectable labels is formed on a surface. Both (1) a signal amplification reagent comprising a binding moiety and (2) a detectable moiety comprising multiple second detectable labels are added to the first complex in one or more steps. The detection reagent comprises multiple first detectable labels, allowing multiple signal amplification reagents to bind to each detection reagent. The detectable moiety comprising multiple second detectable labels binds to each signal amplification reagent via the binding moiety(s).

A further embodiment of the method is illustrated in FIG. 2. In FIG. 2, a first complex comprising a capture reagent, an analyte, and a detection reagent with multiple first detectable labels is formed on a surface. Both (1) a signal amplification reagent comprising a binding moiety and (2) a detectable moiety, comprising multiple second detectable labels, are added to the first complex. In embodiments, the signal amplification reagent and the detectable moiety are simultaneously contacted with the first complex. In embodiments, the signal amplification reagent and the detectable moiety are sequentially contacted with the first complex. In embodiments, the detection reagent comprises multiple first detectable labels, thereby allowing multiple signal amplification reagents to bind to the same detection reagent. Thus, as shown in FIG. 2, in embodiments, each first detectable label on the detection reagent corresponds to multiple second detectable labels on the detectable moiety, thereby amplifying the signal for measurement. Components of the method are further described herein. In embodiments, the first detectable label is an ECL label. In embodiments, the second detectable label is an ECL label.

Figure 3:
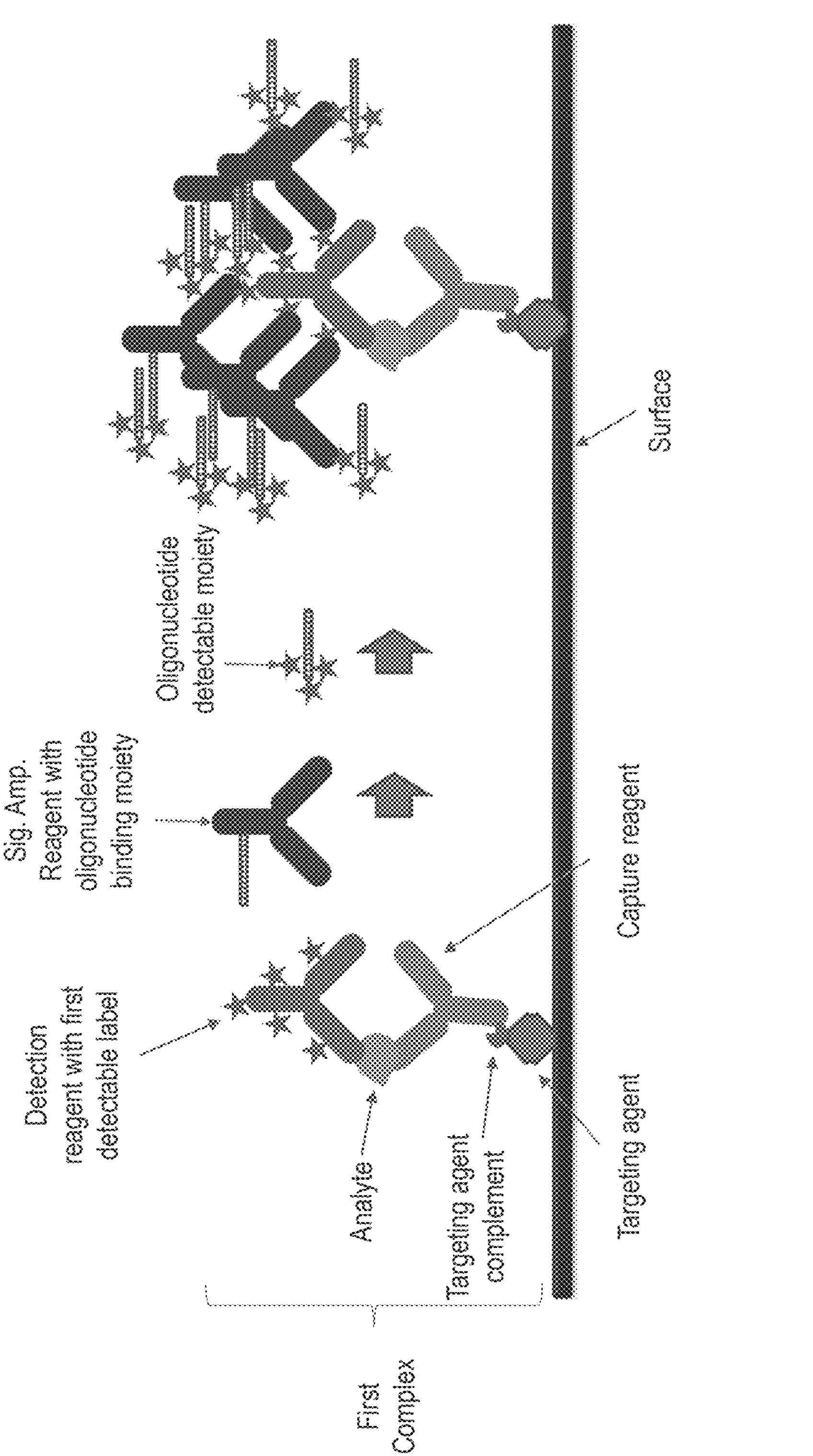
FIG. 3 illustrates an embodiment of the methods described herein. A first complex comprising a capture reagent, an analyte, and a detection reagent with multiple first detectable labels is formed on a surface. The capture reagent is immobilized to the surface via the binding of the targeting agent complement on the capture reagent to the targeting agent on the surface. Both (1) a signal amplification reagent comprising an oligonucleotide binding moiety and (2) an oligonucleotide detectable moiety comprising multiple second detectable labels are added to the first complex in one or more steps. The detection reagent comprises multiple first detectable labels, allowing multiple signal amplification reagents to bind to each detection reagent. The detectable moiety comprising multiple second detectable labels binds to each signal amplification reagent via the binding moiety(s).

A further embodiment of the method is illustrated in FIG. 3. In FIG. 3, a first complex comprising a capture reagent, an analyte, and a detection reagent with multiple first detectable labels is formed on a surface. The capture reagent is immobilized to the surface via the binding of a targeting agent complement on the capture reagent to a targeting agent on the surface. Both (1) a signal amplification reagent comprising an oligonucleotide binding moiety and (2) an oligonucleotide detectable moiety, comprising multiple second detectable labels, are added to the first complex. In embodiments, the signal amplification reagent and the detectable moiety are simultaneously contacted with the first complex. In embodiments, the signal amplification reagent and the detectable moiety are sequentially contacted with the first complex. In embodiments, the detection reagent comprises multiple first detectable labels, thereby allowing multiple signal amplification reagents to bind to the same detection reagent. In embodiments, the oligonucleotide detectable moiety binds to the oligonucleotide binding moiety. Thus, as shown in FIG. 3, in embodiments, each first detectable label on the detection reagent corresponds to multiple second detectable labels on the detectable moiety, thereby amplifying the signal for measurement. Components of the method are further described herein. In embodiments, the first detectable label is an ECL label. In embodiments, the second detectable label is an ECL label.

Figure 4:
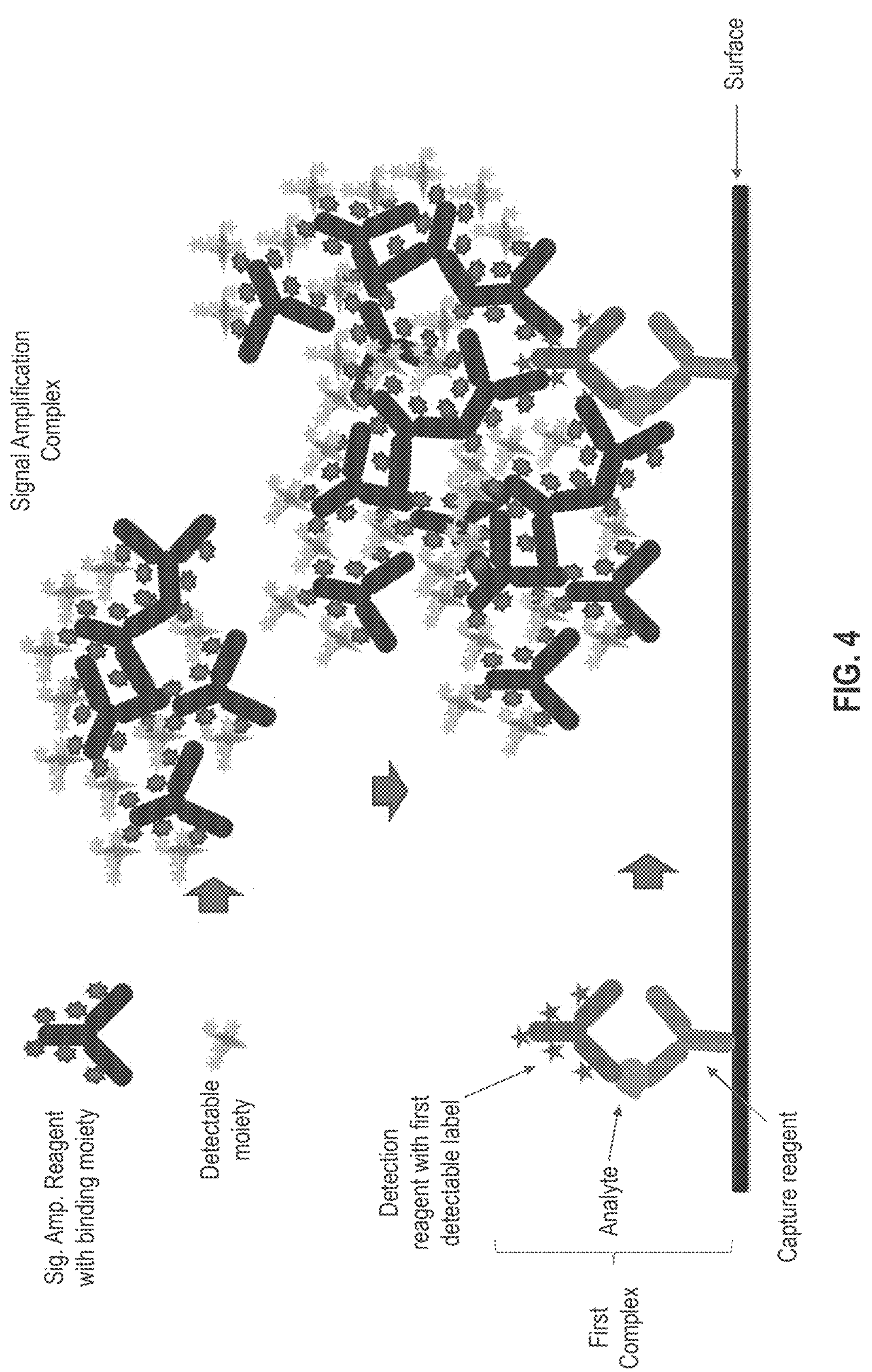
FIG. 4 illustrates an embodiment of the methods described herein. A first complex comprising a capture reagent, an analyte, and a detection reagent with multiple first detectable labels is formed on a surface. A plurality of signal amplification reagents and detectable moieties are mixed, wherein each detectable moiety comprises multiple second detectable labels, and wherein each detectable moiety is capable of binding to multiple binding moieties, thereby forming a signal amplification complex comprising a plurality of signal amplification reagents and detectable moieties. The signal amplification complex is then added to the first complex. The detection reagent comprises multiple first detectable labels, allowing multiple signal amplification reagents of the signal amplification complex to bind to each detection reagent. The detectable moiety comprising multiple second detectable labels binds to each signal amplification reagent via the binding moiety(s).

A further embodiment of the method is illustrated in FIG. 4. In FIG. 4, a first complex comprising a capture reagent, an analyte, and a detection reagent is formed on a surface. A plurality of signal amplification reagents and detectable moieties are mixed, wherein each detectable moiety comprising multiple second detectable labels, and wherein each detectable moiety is capable of binding to multiple binding moieties, thereby forming a signal amplification complex comprising a plurality of signal amplification reagents and detectable moieties. In embodiments, the first complex and the signal amplification complex are formed simultaneously or substantially simultaneously. In embodiments, the first complex and the signal amplification complex are formed sequentially. In embodiments, the first complex is formed on the surface, and the signal amplification complex is formed in a separate container or separate reaction vessel. The signal amplification complex is then added to the first complex. In embodiments, the detection reagent comprises multiple first detectable labels, thereby allowing multiple signal amplification reagents of the signal amplification complex to bind to each detection reagent. Thus, as shown in FIG. 4, each first detectable label on the detection reagent corresponds to multiple second detectable labels on the detectable moiety, thereby amplifying the signal for measurement. Components of the method are further described herein. In embodiments, the first detectable label is an ECL label. In embodiments, the second detectable label is an ECL label.

A further embodiment of the method comprises formation of a first complex on a surface, the first complex comprising a capture reagent, an analyte, and a detection reagent comprising a first nucleic acid probe. The first nucleic acid probe is extended to form a first extended sequence. In embodiments, the first nucleic acid probe is extended by rolling circle amplification. A plurality of first labeled probes, each comprising a first detectable label, binds to the first extended sequence. One or more of (1) a signal amplification reagent comprising a binding moiety and (2) a detectable moiety comprising multiple second detectable labels, are contacted with the first complex. In embodiments, the signal amplification reagent and the detectable moiety are simultaneously contacted with the first complex. In embodiments, the signal amplification reagent and the detectable moiety are sequentially contacted with the first complex. In embodiments, each first labeled probe bound to the first extended sequence binds to a signal amplification reagent. Thus, each first detectable label corresponds to multiple second detectable labels on the detectable moiety, thereby amplifying the signal for measurement. Components of the method are further described herein. In embodiments, the first detectable label is an ECL label. In embodiments, the second detectable label is an ECL label.

A further embodiment of the method is illustrated in FIG. 15. In FIG. 15, a first complex comprising a capture reagent, an analyte, and a detection reagent comprising a first nucleic acid probe is formed on a surface. The first nucleic acid probe is extended to form a first extended sequence. In embodiments, the first nucleic acid probe is extended by rolling circle amplification. A plurality of first labeled probes, each comprising a first detectable label, binds to the first extended sequence. Multiple signal amplification reagents, each comprising a second nucleic acid probe, bind to the first detectable label. Each of the second nucleic acid probes is extended to form a second extended sequence. In embodiments, the second nucleic acid probe is extended by rolling circle amplification. One or more second labeled probes, each comprising a second detectable label, binds to the second extended sequence. Thus, as shown in FIG. 15, each first detectable label corresponds to a second extended sequence that can bind to multiple second labeled probes comprising a second detectable label, thereby amplifying the signal for measurement. Components of the method are further described herein. In embodiments, the first detectable label is an ECL label. In embodiments, the second detectable label is an ECL label.

A further embodiment of the method is illustrated in FIG. 17. In FIG. 17, a first complex comprising a capture reagent, an analyte, and a detection reagent comprising a first detectable label is formed on a surface. Both (1) a signal amplification reagent comprising an enzyme and (2) a substrate of the enzyme are added to the first complex. In embodiments, the signal amplification reagent and the enzyme substrate are simultaneously contacted with the first complex. In embodiments, the signal amplification reagent and the enzyme substrate are sequentially contacted with the first complex. In embodiments, the enzyme acts upon the substrate to produce a detectable signal. In embodiments, the method comprises detecting the detectable signal. Components of the method are further described herein. In embodiments, the first detectable label is an ECL label. In embodiments, the second detectable label is an ECL label.

A further embodiment of the method is illustrated in FIGS. 22A-22D. In each of FIGS. 22A-22D, a complex comprises a capture reagent ("CR"), an analyte, a first detection reagent ("$1^{ST}$ DR")) comprising a first detectable label ("$1^{ST}$ Label"), and a second detection reagent ("$2^{ND}$ DR") comprising a first detectable label, a signal amplification reagent ("SAR") that binds simultaneously to the first detectable label on the first detection reagent and the first detectable label on the second detection reagent. In embodiments, binding of the signal amplification reagent to the two first detectable labels stabilizes the binding of the first and second detection reagents to the analyte. In embodiments, the signal amplification reagent acts as a tether between the two detection reagents and maintains binding of the two detection reagents to the analyte. For example, if one of the two detection reagents dissociates from the analyte but remains bound to the signal amplification reagent, the dissociated detection reagent is maintained in the vicinity of the analyte to facilitate rebinding. Thus, the signal amplification reagent amplifies the assay signal by stabilizing the complex for detection.

In FIG. 22A, the signal amplification reagent is depicted without any other component. The components as labeled in FIG. 22A are the same as for FIGS. 22B-22D. In FIG. 22B, the signal amplification reagent comprises a binding moiety that binds to a detectable moiety comprising a binding partner of the binding moiety and a second detectable label as described herein. In FIG. 22C, the signal amplification reagent comprises a second detectable label as described herein. In FIG. 22D, the signal amplification reagent comprises a nucleic acid probe, which is extended via a template oligonucleotide to form an extended sequence that binds to one or more labeled probes comprising a second detectable label, as described herein. Thus, in FIGS. 22B-22D, the signal amplification reagent amplifies assay signal in a two-fold manner, i.e., by stabilizing the complex as described herein and by providing a further detectable signal via the second detectable label, as described herein.

Assay Components and Methods

In embodiments, the invention provides a method comprising: (a) contacting an ECL label with a signal amplification reagent that specifically binds to the ECL label, wherein:

- the signal amplification reagent comprises a binding moiety, and the method further comprises contacting the ECL label with a detectable moiety; or
- the signal amplification reagent comprises an enzyme, and the method further comprises contacting the ECL label with a substrate of the enzyme; or
- the signal amplification reagent optionally comprises a second detectable label; or
- the signal amplification reagent comprises a nucleic acid probe, and the method further comprises extending the nucleic acid probe to form an extended sequence, and (b) detecting the detectable moiety, enzyme activity, second detectable label, or extended sequence, thereby detecting the ECL label. In embodiments, the ECL label is present on a surface. In embodiments, the ECL label is present on a surface in step (a). In embodiments, the ECL label is present on a surface in step (b). In embodiments, the ECL label is present on a surface comprising an anchoring reagent immobilized thereon.

In embodiments, the invention provides a method of detecting an analyte of interest in a sample, comprising:

(a) contacting a first complex that comprises (A) a first detectable label and (B) the analyte of interest, with: (I) a signal amplification reagent that specifically binds to the first detectable label and that comprises a binding moiety, and (II) a detectable moiety comprising (1) a binding partner of the binding moiety and (2) one or more of a second detectable label; and (b) measuring (I) the second detectable label or (II) the first and second detectable labels on the surface, thereby detecting the analyte of interest;

or (c) contacting a first complex that comprises (A) a first detectable label and (B) the analyte of interest, with: (I) a signal amplification reagent that specifically binds to the first detectable label and that comprises an enzyme, and (II) a substrate of the enzyme; and (d) measuring enzyme activity, thereby detecting the analyte of interest;

or (e) contacting a first complex that comprises (A) a first detectable label, wherein the first detectable label is an ECL label, and (B) the analyte of interest, with a signal amplification reagent that specifically binds to the first detectable label and that optionally comprises a second detectable label; and (f) measuring (I) the first detectable label; (II) the second detectable label; or (III) the first and second detectable labels, thereby detecting the analyte of interest;

or (g) contacting a first complex that comprises (A) a first detectable label, wherein the first detectable label is an electrochemiluminescent (ECL) label, and (B) the analyte of interest, with a signal amplification reagent that specifically binds to the first detectable label, wherein the signal amplification reagent comprises a nucleic acid probe, thereby forming a second complex comprising the first complex and the signal amplification reagent; (h) extending the nucleic acid probe to form an extended sequence; and (i) measuring the amount of extended sequence, thereby detecting the analyte of interest. In embodiments, the first detectable label is an ECL label. In embodiments, the first complex is on a surface. In embodiments, the first complex comprises the analyte of interest; a capture reagent that specifically binds to the analyte, wherein the capture reagent is immobilized on the surface or wherein the capture reagent is capable of being immobilized to the surface; and a detection reagent that specifically binds to the analyte and that comprises the first detectable label.

In embodiments, the signal amplification reagent comprises a nucleic acid probe, and the surface comprises an anchoring reagent immobilized thereon. In embodiments, the signal amplification reagent comprises a nucleic acid probe, and the method further comprises immobilizing an anchoring reagent on the surface. In embodiments, the anchoring reagent is immobilized on the surface prior to or during step (h) of the method. In embodiments, the anchoring reagent binds to an anchoring region of the extended sequence, and the measuring comprises measuring the amount of extended sequence on bound to the surface via the anchoring reagent. In embodiments, the first complex comprises the analyte of interest; a capture reagent that specifically binds to the analyte, wherein the capture reagent is immobilized on the surface or wherein the capture reagent is capable of being immobilized to the surface; and a detection reagent that specifically binds to the analyte and that comprises the first detectable label.

In embodiments, the invention provides a method of detecting an analyte of interest in a sample, comprising (a) forming a first complex on a surface comprising the analyte of interest; a capture reagent that specifically binds to the analyte, wherein the capture reagent is immobilized on the surface or wherein the capture reagent is capable of being immobilized to the surface; and a detection reagent that specifically binds to the analyte and that comprises a first nucleic acid probe; (b) extending the first nucleic acid probe to form a first extended sequence comprising a first anchoring region, wherein the first anchoring region binds a first anchoring reagent that is immobilized on the surface; (c) binding the first extended sequence to a first labeled probe comprising a first detectable label; and:

(d) contacting the first labeled probe bound to the first extended sequence with: (I) a signal amplification reagent that specifically binds to the first detectable label and that comprises a binding moiety, and (II) a detectable moiety comprising (1) a binding partner of the binding moiety and (2) one or more of a second detectable label; and (e) measuring (I) the second detectable label or (II) the first and second detectable labels, thereby detecting the analyte of interest, thereby detecting the analyte of interest;

or (f) contacting the first labeled probe bound to the first extended sequence with: (I) a signal amplification reagent that specifically binds to the first detectable label and that comprises an enzyme, and (II) a substrate of the enzyme; and (g) measuring enzyme activity, thereby detecting the analyte of interest;

or (h) contacting the first labeled probe bound to the first extended sequence with a signal amplification reagent that specifically binds to the first detectable label and that optionally comprises a second detectable label; and (i) measuring (I) the first detectable label; (II) the second detectable label; or (III) the first and second detectable labels, thereby detecting the analyte of interest;

or (j) contacting the first labeled probe bound to the first extended sequence with a signal amplification reagent that specifically binds to the first detectable label, wherein the signal amplification reagent comprises a second nucleic acid probe, thereby forming a second complex comprising the signal amplification reagent and the first labeled probe; (k) extending the second nucleic acid probe to form a second extended sequence comprising a second anchoring region, wherein the second anchoring region binds a second anchoring reagent that is immobilized on the surface; and; (l) measuring the amount of (I) the second extended sequence or (II) the first extended sequence and the second extended sequence bound to the surface, thereby detecting the analyte of interest. In embodiments, the first detectable label is an ECL label.

Capture Reagent

In embodiments, the capture reagent comprises an antibody or antigen-binding fragment thereof, antigen, ligand, receptor, oligonucleotide, hapten, epitope, mimotope, or aptamer. In embodiments, the capture reagent comprises an antibody or a variant thereof, including an antigen/epitope-binding portion thereof, an antibody fragment or derivative, an antibody analogue, an engineered antibody, or a substance that binds to antigens in a similar manner to antibodies. In embodiments, the capture reagent comprises at least one heavy or light chain complementarity determining region (CDR) of an antibody. In embodiments, the capture reagent comprises at least two CDRs from one or more antibodies. In embodiments, the capture reagent comprises an antibody or antigen-binding fragment thereof.

In embodiments, the capture reagent specifically binds to the analyte. As used herein, "specifically binds" means that a reagent (e.g., a capture reagent) preferentially binds to its binding partner (e.g., an epitope of the analyte) relative a random, unrelated substance. In embodiments, the capture reagent comprises an antibody or antigen-binding fragment thereof, comprising an antigen binding domain that specifically binds to an epitope of the analyte.

In embodiments, the capture reagent is immobilized on a surface. In embodiments, the capture reagent is capable of being immobilized to a surface. Methods of immobilizing a capture reagent to a surface are further described herein. In embodiments, the capture reagent is immobilized to the surface via a thioester, thioether, disulfide, or combination thereof. In embodiments, the capture reagent is immobilized to the surface via a targeting agent as described herein. In embodiments, the capture reagent is immobilized to the surface before, during, or after formation of the first complex described herein. In embodiments, the capture reagent is immobilized to the surface before step (a) of the method.

Detection Reagent

In embodiments, the detection reagent comprises an antibody or antigen-binding fragment thereof, antigen, ligand, receptor, oligonucleotide, hapten, epitope, mimotope, or aptamer. In embodiments, the detection reagent comprises an antibody or a variant thereof, including an antigen/epitope-binding portion thereof, an antibody fragment or derivative, an antibody analogue, an engineered antibody, or a substance that binds to antigens in a similar manner to antibodies. In embodiments, the detection reagent comprises at least one heavy or light chain complementarity determining region (CDR) of an antibody. In embodiments, the detection reagent comprises at least two CDRs from one or more antibodies. In embodiments, the detection reagent comprises an antibody or antigen-binding fragment thereof.

In embodiments, the detection reagent specifically binds to the analyte. In embodiments, the detection reagent comprises an antibody or antigen-binding fragment thereof, comprising an antigen-binding domain that specifically binds to an epitope of the analyte. In embodiments, the detection reagent binds to a different epitope of the analyte than the capture reagent.

In embodiments, the first complex comprises more than one detection reagent. In embodiments, the first complex comprises at least two detection reagents. In embodiments, the detection reagent of the first complex as described herein is a first detection reagent, and the first complex further comprises a second detection reagent. In embodiments, the first and second detection reagents each specifically binds to the analyte. In embodiments, the first and second detection reagents bind to a same epitope on the analyte. In embodiments, the analyte comprises multiple copies of the epitope for binding to the first and second detection reagents, such that the first and second detection reagents are capable of simultaneously binding to separate copies of the epitope on the analyte. In embodiments, the first and second detection reagents bind to different epitopes on the analyte. In embodiments, each of the capture reagent and the first and second detection reagents bind to different epitopes on the analyte. In embodiments, the capture reagent binds to a first epitope on the analyte, and each of the first and second detection reagents binds to a second epitope on the analyte. In embodiments, the analyte comprises multiple copies of the second epitope, such that the first and second detection reagents are capable of simultaneously binding to separate copies of the second epitope on the analyte. In embodiments, the first complex comprises the capture reagent, the analyte, the first detection reagent, and the second detection reagent, wherein the capture reagent, the first detection reagent, and the second detection reagent are bound to the analyte.

In embodiments, the first and second detection reagents each independently comprises an antibody or antigen-binding fragment thereof, antigen, ligand, receptor, oligonucleotide, hapten, epitope, mimotope, or aptamer. In embodiments, each of the first and second detection reagents comprises an antibody or a variant thereof, including an antigen/epitope-binding portion thereof, an antibody fragment or derivative, an antibody analogue, an engineered antibody, or a substance that binds to antigens in a similar manner to antibodies. In embodiments, each of the first and second detection reagents comprises at least one heavy or light chain complementarily determining region (CDR) of an antibody. In embodiments, each of the first and second detection reagents comprises at least two CDRs from one or more antibodies. In embodiments, each of the first and second detection reagents comprises an antibody or antigen-binding fragment thereof Detection Reagent Comprising First Detectable Label In embodiments, the detection reagent comprises a first detectable label. In embodiments, the detection reagent comprises multiple first detectable labels. In embodiments, the detection reagent comprises 1, 2, 3, 4, 5, 6, 7, 8, 9, 10, or more than 10 of the first detectable label. In embodiments where the first complex comprises first and second detection reagents, each of the first and second detection reagents comprises a first detectable label. In embodiments, each of the first and second detection reagents comprises 1, 2, 3, 4, 5, 6, 7, 8, 9, 10, or more than 10 of the first detectable label. In embodiments, the detection reagent of the first complex, or each of the first and second detection reagents of the first complex, comprises at least two of the first detectable label. In embodiments, the first detectable label is capable of being detected by light scattering, optical absorbance, fluorescence, chemiluminescence, electrochemiluminescence, bioluminescence, phosphorescence, radioactivity, magnetic field, or combination thereof. In embodiments, the first detectable label comprises an ECL label.

In embodiments, the ECL label comprises an electrochemiluminescent organometallic complex. In embodiments, the electrochemiluminescent organometallic complex comprises ruthenium, osmium, iridium, rhenium, and/or a lanthanide metal. In embodiments, the ECL label comprises ruthenium. In embodiments, the electrochemiluminescent organometallic complex comprises a substituted or unsubstituted bipyridine or a substituted or unsubstituted phenanthroline. In embodiments, the ECL label comprises a substituted bipyridine. In embodiments, the ECL label comprises an organometallic complex comprising at least one substituted bipyridine ligand, wherein the substituted bipyridine ligand comprises at least one sulfonate group. In embodiments, the ECL label comprises an organometallic complex comprising at least two substituted bipyridine ligands, wherein each substituted bipyridine ligand comprises at least one sulfonate group. In embodiments, the substituted bipyridine ligand comprising at least one sulfonate group is a compound of Formula I:

(I)

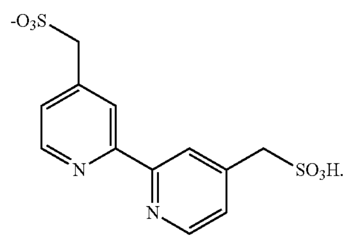

In embodiments, the ECL label comprises three ligands, wherein a first ligand is a compound of Formula I, and wherein a second ligand comprises a bipyridine having at least one substituent that is covalently linked to the detection reagent. In embodiments, the ECL label comprises an organometallic complex that comprises three ligands, wherein two of the ligands are each a compound of Formula I, and wherein the third ligand comprises a bipyridine having at least one substituent that is covalently linked to the detection reagent. In embodiments, the organometallic complex comprises ruthenium, osmium, or rhenium.

Exemplary ECL labels can be found in U.S. Pat. Nos. 5,714,089; 6,136,268; 6,316,607; 6,468,741; 6,479,233; 6,808,939; and 9,499,573.

In embodiments, the first detectable label is a compound of Formula II:

(II)

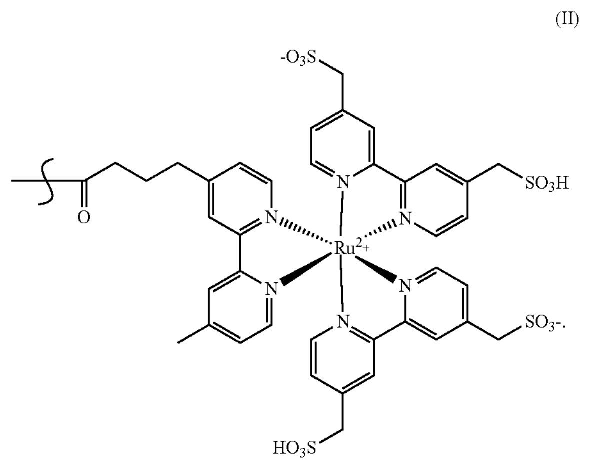

In embodiments, the first detectable label is a compound of Formula III:

(III)

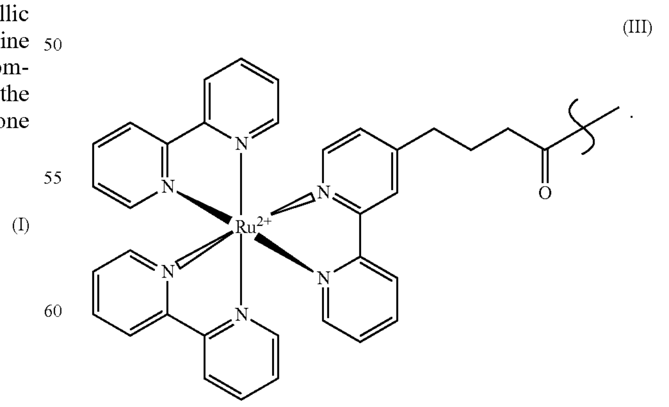

In embodiments, the first detectable label is a compound of Formula IV:

(IV)

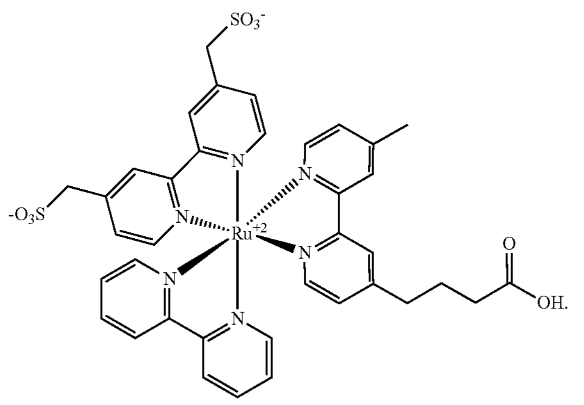

In embodiments, the first detectable label is a compound of Formula V:

(V)

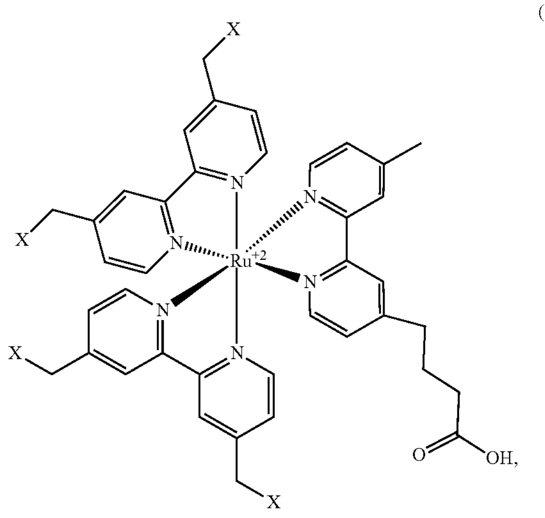

wherein each X comprises a phosphate, a carbonate, a borate, or combination thereof.

In embodiments, the first detectable label is a compound of Formula VI:

(VI)

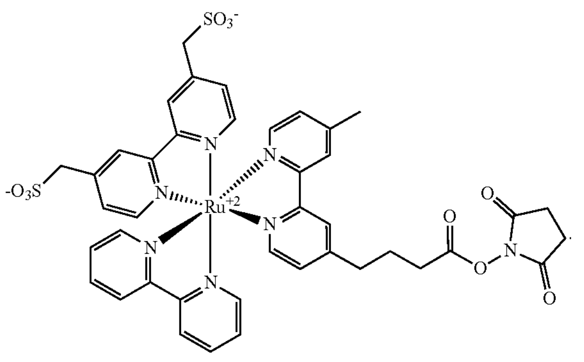

In embodiments, the detection reagent (e.g., a first and/or second detection reagent as described herein) is covalently linked to the first detectable label via a conjugation linker. In embodiments, the conjugation linker comprises an amide, a thioester, a thioether, a disulfide, an imine, a triazole, a dihydropyridazine, a peptide, an oligonucleotide, a hydrophilic polymer, or a combination thereof. In embodiments, the amide of the conjugation linker results from the reaction between an N-hydroxysuccinimide (NHS) ester and an amine. In embodiments, the thioester of the conjugation linker results from the reaction between an NHS ester and a thiol (also called a sulfhydryl). In embodiments, the thioether of the conjugation linker results from the reaction between a maleimide or alkene and a thiol. In embodiments, the disulfide of the conjugation linker results from the reaction between a disulfide and a thiol. In embodiments, the imine of the conjugation linker results from the reaction between an aldehyde or ketone and an amine. In embodiments, the triazole of the conjugation linker results from the reaction between an alkyne or a cycloalkyne and an azide. In embodiments, the dihydropyridazine of the conjugation linker results from the reaction between a trans-cyclooctene and a tetrazine.

In embodiments, the conjugation linker comprises a spacer, e.g., to increase the distance and/or movement flexibility between the detection reagent and the first detectable label. In embodiments, the conjugation linker comprises a peptide. In embodiments, the conjugation linker comprises an oligonucleotide. In embodiments, the conjugation linker comprises a hydrophilic polymer. In embodiments, the hydrophilic polymer comprises polyethylene glycol (PEG).

Detection Reagent Comprising First Nucleic Acid Probe

In embodiments, the detection reagent comprises a first nucleic acid probe. In embodiments, the first nucleic acid probe is capable of being extended to form a first extended sequence. In embodiments, the first nucleic acid probe is capable of being ligated to a further oligonucleotide to form a first extended sequence. In embodiments, the first nucleic acid probe is capable of being ligated to a further oligonucleotide, wherein at least a portion of the further oligonucleotide comprises a complementary sequence to the first nucleic acid probe, to form a first extended sequence. In embodiments, the first nucleic acid probe is capable of binding to a template oligonucleotide. In embodiments, the first nucleic acid probe is a primer for an extension reaction. In embodiments, the extension reaction comprises polymerase chain reaction (PCR), ligase chain reaction (LCR), strand displacement amplification (SDA), self-sustained synthetic reaction (3SR), isothermal amplification (such as, e.g., helicase-dependent amplification or rolling circle amplification), or combination thereof. In embodiments, the first nucleic acid probe binds to a template oligonucleotide and is extended by PCR, LCR, SDA, 3SR, isothermal amplification (such as, e.g., helicase-dependent amplification or rolling circle amplification), or combination thereof to form a first extended sequence. In embodiments, the first nucleic acid probe binds to a template oligonucleotide and is extended by PCR to form a first extended sequence. In embodiments, the first nucleic acid probe binds to a template oligonucleotide, forms a circular template oligonucleotide (e.g., by ligation of a linear template oligonucleotide), and is extended by rolling circle amplification to form a first extended sequence. In embodiments where the first complex comprises first and second detection reagents, each of the first and second detection reagents comprises a proximity nucleic acid probe, wherein one or both of the proximity nucleic acid probes is capable of being extended to form a first extended sequence only when the two proximity nucleic acid probes are in proximity.

In embodiments, the first extended sequence comprises a first anchoring region. In embodiments, the first anchoring region binds to a first anchoring reagent on a surface. In embodiments, the first anchoring reagent is immobilized on the surface before, during, or after forming the first complex described herein. In embodiments, the first anchoring reagent is immobilized to the surface before step (a) of the method described herein. In embodiments, the first anchoring reagent is immobilized to the surface prior to forming the first extended sequence. In embodiments, the first anchoring reagent is immobilized to the surface via a thioester, thioether, disulfide, or combination thereof. In embodiments, the first anchoring reagent is immobilized to the surface via a targeting agent as further described herein.

In embodiments, the first anchoring reagent comprises an oligonucleotide, aptamer, aptamer ligand, antibody, antigen, ligand, receptor, hapten, epitope, or mimotope. In embodiments, the first anchoring reagent comprises an aptamer ligand, and the first anchoring region comprises an aptamer. In embodiments, the first anchoring reagent comprises an oligonucleotide-binding protein, and the first anchoring region comprises an oligonucleotide sequence. In embodiments, the first anchoring reagent comprises a single stranded oligonucleotide. In embodiments, the first anchoring reagent comprises a double stranded oligonucleotide. In embodiments, the first anchoring reagent and the first anchoring region comprise complementary oligonucleotides. In embodiments, the first anchoring reagent comprises an anchoring oligonucleotide. In embodiments, the first anchoring region comprises an anchoring oligonucleotide complement that is complementary to the anchoring oligonucleotide.

In embodiments, binding the first extended sequence to the first anchoring reagent comprises forming a triple helix between the first anchoring reagent and the first anchoring region. In embodiments, binding the first extended sequence to the first anchoring reagent comprises denaturing the first anchoring region to expose a single stranded oligonucleotide region prior to the binding; exposing the first anchoring region to helicase activity prior to the binding; and/or exposing the first anchoring region to nuclease treatment prior to the binding, wherein the first anchoring region comprises one or more hapten-modified bases and the first anchoring reagent comprises one or more antibodies specific for the hapten; and/or the first anchoring region comprises one or more ligand-modified bases and the first anchoring reagent comprises one or more receptors specific for the ligand.

In embodiments, the first complex comprising the capture reagent, the analyte, and the detection reagent (or first and second detection reagents) is bound to the surface following extension of the first nucleic acid probe. In embodiments, the first extended sequence binds to the first anchoring reagent at a position within about 1 nm to about 500 nm, about 5 nm to about 250 nm, about 10 nm to about 200 nm, or about 15 nm to about 150 nm from the first complex on the surface. In embodiments, the first extended sequence binds to the first anchoring reagent at a position less than 1 μm from the first complex on the surface. In embodiments, the first extended sequence binds to the first anchoring reagent at a position less than 500 nm from the first complex on the surface. In embodiments, the first extended sequence binds to the first anchoring reagent at a position less than 200 nm from the first complex on the surface.

In embodiments, the method comprises, following the extending of the first nucleic acid probe and/or binding of the first extended sequence to the first anchoring reagent, binding the first extended sequence to a first labeled probe comprising a first detectable label. In embodiments, the first extended sequence and the first labeled probe comprise complementary oligonucleotides. In embodiments, the first labeled probe comprises more than one of the first detectable label. In embodiments, the first labeled probe comprises 1, 2, 3, 4, 5, 6, 7, 8, 9, 10, or more than 10 of the first detectable label. In embodiments, the first detectable label is covalently linked to the first labeled probe, e.g., via a conjugation linker as described herein.

First detectable labels are further described herein. In embodiments, the first detectable label is capable of being detected by light scattering, optical absorbance, fluorescence, chemiluminescence, electrochemiluminescence, bioluminescence, phosphorescence, radioactivity, magnetic field, or combination thereof. In embodiments, the first detectable label comprises an ECL label as described herein. In embodiments, the ECL label comprises an organometallic complex comprising at least one substituted bipyridine ligand, wherein the substituted bipyridine ligand comprises at least one sulfonate group. In embodiments, the ECL label comprises an organometallic complex comprising at least two substituted bipyridine ligands, wherein each substituted bipyridine ligand comprises at least one sulfonate group. In embodiments, the substituted bipyridine ligand is a compound of Formula I. In embodiments, the ECL label comprises three ligands, wherein a first ligand is a compound of Formula I, and wherein a second ligand comprises a bipyridine having at least one substituent that is covalently linked to the first labeled probe. In embodiments, the ECL label comprises an organometallic complex that comprises three ligands, wherein two of the ligands are each a compound of Formula I, and wherein the third ligand comprises a bipyridine having at least one substituent that is covalently linked to the first labeled probe. In embodiments, the organometallic complex comprises ruthenium, osmium, or rhenium.

In embodiments, the first detectable label comprises a compound of Formula II. In embodiments, the first detectable label comprises a compound of Formula III. In embodiments, the first detectable label comprises a compound of Formula IV. In embodiments, the first detectable label comprises a compound of Formula V. In embodiments, the first detectable label comprises a compound of Formula VI.

Signal Amplification Reagent

In embodiments, the signal amplification reagent comprises an antibody or antigen-binding fragment thereof, antigen, ligand, receptor, oligonucleotide, hapten, epitope, mimotope, or aptamer. In embodiments, the signal amplification reagent comprises an antibody or a variant thereof, including an antigen/epitope-binding portion thereof, an antibody fragment or derivative, an antibody analogue, an engineered antibody, or a substance that binds to antigens in a similar manner to antibodies. In embodiments, the signal amplification reagent comprises at least one heavy or light chain complementarity determining region (CDR) of an antibody. In embodiments, the signal amplification reagent comprises at least two CDRs from one or more antibodies. In embodiments, the signal amplification reagent comprises an antibody or antigen-binding fragment thereof. In embodiments, the antibody or antigen-binding fragment thereof comprises a constant region comprising an IgA, IgD, IgE, IgG, or IgM domain. In embodiments, the antibody or antigen-binding fragment thereof comprises an IgG domain. In embodiments, the antibody or antigen-binding fragment thereof comprises an IgG1, IgG2, IgG3, or IgG4 isotype antibody or antigen-binding fragment thereof. In embodiments, the antibody or antigen-binding fragment thereof comprises IgG2a, IgG2b, or IgG2c subclass antibody or antigen-binding fragment thereof. In embodiments, the antibody or antigen-binding fragment thereof is derived from a mouse, rat, goat, rabbit, chicken, guinea pig, hamster, horse, or sheep. In embodiments, the antibody or antigen-binding fragment thereof is derived from a mouse. Antibodies and antigen-binding fragments are further described herein.

In embodiments, the signal amplification reagent specifically binds to a first detectable label. In embodiments, the signal amplification reagent comprises an antibody or antigen-binding fragment thereof comprising an antigen binding domain that specifically binds to the first detectable label.

In embodiments, the signal amplification reagent is capable of specifically binding to at least two first detectable labels. In embodiments, the signal amplification reagent comprises at least two antigen binding domains, wherein each antigen binding domain specifically binds to a first detectable label. In embodiments, the signal amplification reagent is capable of binding to a first detectable label on a first detection reagent and a first detectable label on a second detection reagent, e.g., as depicted in FIG. 22A. As described herein, a signal amplification reagent that is capable of binding to at least two detectable labels on first and second detection reagents stabilizes the binding of the detection reagents to the analyte, thereby amplifying an assay signal for detecting the analyte. In embodiments, the at least two first detectable labels bound by the signal amplification reagent comprise the same structure. In embodiments, the at least two first detectable labels bound by the signal amplification reagent comprise different structures.

First detectable labels are described herein. In embodiments, the first detectable label is an ECL label as described herein. In embodiments, the signal amplification reagent binds two first detectable labels, wherein each first detectable label bound by the signal amplification reagent is an ECL label as described herein. In embodiments, the ECL label comprises an organometallic complex comprising at least one substituted bipyridine ligand, wherein the substituted bipyridine ligand comprises at least one sulfonate group. In embodiments, the ECL label comprises an organometallic complex comprising at least two substituted bipyridine ligands, wherein each substituted bipyridine ligand comprises at least one sulfonate group. In embodiments, the substituted bipyridine ligand is a compound of Formula I. In embodiments, the ECL label comprises three ligands, wherein at least one of the ligands is a compound of Formula I. In embodiments, the ECL label comprises three ligands, wherein one of the ligands is a compound of Formula I. In embodiments, the ECL label comprises an organometallic complex that comprises three ligands, wherein two of the ligands are each a compound of Formula I.

In embodiments, the signal amplification reagent specifically binds a compound of Formula II. In embodiments, the signal amplification reagent specifically binds a compound of Formula IV. In embodiments, the signal amplification reagent specifically binds a compound of Formula VI.

In embodiments, the signal amplification reagent specifically binds two first detectable labels, wherein the two first detectable labels comprise the same structure, e.g., each first detectable label comprises a compound of Formula II, III, IV, V, or VI. In embodiments, the signal amplification reagent specifically binds two first detectable labels, wherein the two first detectable labels comprise different structures, e.g., each of the two first detectable labels comprises a compound of Formula II, III, IV, V, or VI, provided that the two first detectable labels do not comprise the same compound. In embodiments, each first detectable label independently comprises a compound of Formula II, III, IV, V, or VI. In embodiments, each first detectable label independently comprises a compound of Formula II, IV, or VI.

In embodiments, the first detectable label is covalently linked, e.g., to a detection reagent (e.g., first and/or second detection reagent) or a first labeled probe as described herein. In embodiments, the signal amplification reagent specifically binds to a first detectable label and a conjugation linker. In embodiments, In embodiments, the signal amplification reagent comprises an antibody or antigen-binding fragment thereof comprising an antigen binding domain that specifically binds to the first detectable label and the conjugation linker. In such embodiments, the signal amplification reagent does not bind to unconjugated first detectable label (i.e., not attached to a detection reagent or a first labeled probe). Unconjugated first detectable label may be present in an assay mixture, for example, from a conjugation reaction to attach the first detectable label to a detection reagent or first labeled probe. In embodiments, a method utilizing the signal amplification reagent that specifically binds to a first detectable label and conjugation linker has improved specificity, relative to a method utilizing a signal amplification reagent that binds to a first detectable label alone.

In embodiments, the conjugation linker comprises an amide, a thioester, a thioether, a disulfide, an imine, a triazole, a dihydropyridazine, a peptide, an oligonucleotide, a hydrophilic polymer, or a combination thereof. In embodiments, the signal amplification reagent specifically binds to the ECL label and an amide. In embodiments, the signal amplification reagent specifically binds to the ECL label and a thioester. In embodiments, the signal amplification reagent specifically binds to the ECL label and a thioether. In embodiments, the signal amplification reagent specifically binds to the ECL label and a disulfide. In embodiments, the signal amplification reagent specifically binds to the ECL label and an imine. In embodiments, the signal amplification reagent specifically binds to the ECL label and a triazole. In embodiments, the signal amplification reagent specifically binds to the ECL label and a dihydropyridazine.

In embodiments, the conjugation linker comprises a spacer (e.g., a peptide, an oligonucleotide, or a hydrophilic polymer as described herein), and the signal amplification reagent specifically binds to the first detectable label and at least a portion of the peptide, oligonucleotide, or hydrophilic polymer of the conjugation linker. In embodiments, the signal amplification reagent specifically binds to the ECL label and at least a portion of a peptide of the conjugation linker. In embodiments, the signal amplification reagent specifically binds to the ECL label and at least a portion of an oligonucleotide of the conjugation linker. In embodiments, the signal amplification reagent specifically binds to the ECL label and at least a portion of a hydrophilic polymer of the conjugation linker.

It was further surprisingly discovered that the antibody signal amplification reagent has high specificity to the ECL labels described herein, including a sulfonated ECL label. Most antibodies require a hydrophobic patch for specificity, and thus the sulfonate groups were expected to be less immunogenic as compared to non-sulfonated labels.

I. Signal Amplification of a First Complex Comprising First Detectable Label

In embodiments, the invention provides a method of detecting an analyte of interest in a sample, comprising contacting a first complex that comprises (A) a first detectable label, wherein the first detectable label is an electrochemiluminescent (ECL) label, and (B) the analyte of interest, with a signal amplification reagent. In embodiments, the first complex comprises the analyte of interest, a capture reagent that specifically binds to the analyte, and a detection reagent that specifically binds to the analyte. In embodiments, the detection reagent comprises the first detectable label, as described herein. In embodiments, the detection reagent is a first detection reagent, and the first complex further comprises a second detection reagent that specifically binds to the analyte and that comprises a first detectable label as described herein.

In embodiments, the first complex is on a surface. In embodiments, the first complex comprises the analyte, a capture reagent that specifically binds to the analyte, and a detection reagent that specifically binds to the analyte. In embodiments, the method comprises, prior to the contacting, forming the first complex. In embodiments, forming the first complex comprises: contacting the analyte of interest with (i) the surface; (ii) the capture reagent; and (iii) the detection reagent. In embodiments, forming the first complex comprises: contacting the sample with (i) the surface; (ii) the capture reagent; and (iii) the detection reagent.

In embodiments, the first complex comprises the analyte of interest, a capture reagent that specifically binds to the analyte, a first detection reagent that specifically binds to the analyte, and a second detection reagent specifically binds to the analyte, wherein each of the first and second detection reagents comprises a first detectable label, as described herein. In embodiments, the method comprises, prior to the contacting, forming the first complex. In embodiments, forming the first complex comprises: contacting the analyte of interest with (i) the surface; (ii) the capture reagent; (iii) the first detection reagent; and (iv) the second detection reagent. In embodiments, forming the first complex comprises: contacting the sample with (i) the surface; (ii) the capture reagent; (iii) the first detection reagent; and (iv) the second detection reagent. In embodiments, the first complex is formed by contacting the analyte with the capture reagent and the first and second detection reagents in any order.

In embodiments, the capture reagent is immobilized on the surface, as described herein. In embodiments, the capture reagent is capable of being immobilized on the surface. In embodiments, the method comprises immobilizing the capture reagent to the surface before, during, or after formation of the first complex. In embodiments, the method comprises immobilizing the capture reagent to the surface prior to step (a) of the method.

In embodiments, the method further comprises, prior to contacting the first complex with the signal amplification reagent, detecting the first complex on the surface. In embodiments, the detecting comprises measuring the amount of the first detectable label, e.g., on the detection reagent. In embodiments where the first complex comprises first and second detection reagents, the detecting comprises measuring the amount of the first detectable label on the first and second detection reagents. In embodiments, the first detectable label is measured by light scattering, optical absorbance, fluorescence, chemiluminescence, electrochemiluminescence, bioluminescence, phosphorescence, radioactivity, magnetic field, or combination thereof. In embodiments, the first detectable label comprises an ECL label, and measuring the amount of the first detectable label comprises measuring an ECL signal.

In embodiments, the detection reagent comprises multiple first detectable labels, and multiple signal amplification reagents bind to the detection reagent, wherein each signal amplification reagent binds to a separate first detectable label on the detection reagent.

In embodiments, the first complex comprises first and second detection reagents, wherein each of the first and second detection reagent comprises a first detectable label as described herein, and the signal amplification reagent is capable of simultaneously binding to the first detectable label on the first detection reagent and to the first detectable label on the second detection reagent, e.g., as shown in FIGS. 22A-22D.

I.A. Signal Amplification Reagent Comprising Binding Moiety

In embodiments, the first complex comprising the capture reagent, the analyte, and the detection reagent comprising the first detectable label is contacted with: (1) a signal amplification reagent that specifically binds to the first detectable label and that comprises a binding moiety, and (2) a detectable moiety, wherein the detectable moiety comprises: (i) a binding partner of the binding moiety and (ii) one or more of a second detectable label. In embodiments, the first complex comprises first and second detection reagents that each comprises a first detectable label, and the signal amplification reagent specifically binds to the first detectable label on the first detection reagent and to the first detectable label on the second detection reagent, as described herein and as depicted in FIG. 22B.

In embodiments, the binding moiety comprises an oligonucleotide, and the detectable moiety comprises a complementary oligonucleotide. In embodiments, the binding moiety and the detectable moiety comprise a receptor-ligand pair, an antigen-antibody pair, a hapten-antibody pair, an epitope-antibody pair, a mimotope-antibody pair, an aptamer-target molecule pair, or an intercalator-target molecule pair. In embodiments, the binding moiety comprises multiple binding sites for the detectable moiety. In embodiments, the binding moiety comprises 2, 3, 4, 5, 6, 7, 8, 9, or 10 binding sites for the detectable moiety. In embodiments, the detectable moiety comprises multiple binding sites for the binding moiety. In embodiments, the detectable moiety comprises 2, 3, 4, 5, 6, 7, 8, 9, or 10 binding sites for the binding moiety. For example, one streptavidin is capable of binding four biotin molecules. In embodiments, the binding moiety comprises biotin, and the detectable moiety comprises avidin or streptavidin. In embodiments, the binding moiety comprises avidin or streptavidin, and the detectable moiety comprises biotin.

In embodiments, the detectable moiety comprises a second detectable label. In embodiments, the detectable moiety comprises more than one of the second detectable label. In embodiments, the detectable moiety comprises 1, 2, 3, 4, 5, 6, 7, 8, 9, 10, or more than 10 of the second detectable label.

In embodiments, the second detectable label is capable of being detected by light scattering, optical absorbance, fluorescence, chemiluminescence, electrochemiluminescence, bioluminescence, phosphorescence, radioactivity, magnetic field, or combination thereof. In embodiments, the second detectable label comprises an ECL label as described herein. In embodiments, the ECL label comprises an organometallic complex comprising at least one substituted bipyridine ligand, wherein the substituted bipyridine ligand comprises at least one sulfonate group. In embodiments, the ECL label comprises an organometallic complex comprising at least two substituted bipyridine ligands, wherein each substituted bipyridine ligand comprises at least one sulfonate group. In embodiments, the substituted bipyridine ligand is a compound of Formula I. In embodiments, the ECL label comprises three ligands, wherein a first ligand is a compound of Formula I, and wherein a second ligand comprises a bipyridine having at least one substituent that is covalently linked to the detectable moiety. In embodiments, the ECL label comprises an organometallic complex that comprises three ligands, wherein two of the ligands are each a compound of Formula I, and wherein the third ligand comprises a bipyridine having at least one substituent that is covalently linked to the detectable moiety. In embodiments, the organometallic complex comprises ruthenium, osmium, or rhenium.

In embodiments, the second detectable label comprises a compound of Formula II. In embodiments, the second detectable label comprises a compound of Formula III. In embodiments, the second detectable label comprises a compound of Formula IV. In embodiments, the second detectable label comprises a compound of Formula V. In embodiments, the second detectable label comprises a compound of Formula VI.

In embodiments, the first detectable label of the detection reagent (e.g., first and/or second detection reagents) and second detectable label of the detectable moiety are the same. In embodiments, the first and second detectable labels each comprises an ECL label as described herein. In embodiments, the first and second detectable labels each comprises a compound of Formula II. In embodiments, the first and second detectable labels each comprises a compound of Formula III. In embodiments, the first and second detectable labels each comprises a compound of Formula IV. In embodiments, the first and second detectable labels each comprises a compound of Formula V. In embodiments, the first and second detectable labels each comprises a compound of Formula VI.

In embodiments, the first and second detectable labels are different. In embodiments, the first detectable label is not detectable once it is bound by the signal amplification reagent. In embodiments, the signal amplification reagent specifically binds to the first detectable label, and not the second detectable label. In embodiments, the first detectable label comprises a compound of Formula II, and the second detectable label comprises a compound of any one of Formulas III, IV, V, or VI. In embodiments, the first detectable label comprises a compound of Formula III, and the second detectable label comprises a compound of any one of Formulas II, IV, V, or VI. In embodiments, the first detectable label comprises a compound of Formula IV, and the second detectable label comprises a compound of any one of Formulas II, III, V, or VI. In embodiments, the first detectable label comprises a compound of Formula V, and the second detectable label comprises a compound of any one of Formulas II, III, IV, or VI. In embodiments, the first detectable label comprises a compound of Formula VI, and the second detectable label comprises a compound of any one of Formulas II, III, IV, or V.

In embodiments, the first detectable label is detectably distinct from the second detectable label. As used herein, two species that are "detectably distinct" means that different detection methods or parameters are used to detect the two species. For example, a fluorescent species is detectably distinct from a chemiluminescent or electrochemiluminescent species. In a further example, an electrochemiluminescent species is detectably distinct from a chromogenic species. In another example, two fluorescent species that have different, non-overlapping excitation and/or emission wavelengths are detectably distinct. In embodiments, the presence of the first detectable label, e.g., on the detection reagent bound by the signal amplification reagent, does not interfere with detection of the second detectable label.

In embodiments, the first complex is first contacted with the signal amplification reagent, then contacted with the detectable moiety. In embodiments, the first complex is contacted with the signal amplification reagent and the detectable moiety simultaneously or substantially simultaneously. As used herein, the term "simultaneous" in reference to one or more events (e.g., contacting the first binding complex with the signal amplification reagent and the detectable moiety) means that the events occur at exactly the same time or at substantially the same time, e.g., simultaneous events described herein can occur less than or about 10 minutes apart, less than or about 5 minutes apart, less than or about 2 minutes apart, less than or about 1 minute apart, less than or about 30 seconds apart, less than or about 15 seconds apart, or less than or about 5 seconds apart.

In embodiments, the contacting comprises: (i) forming a signal amplification complex comprising the signal amplification reagent and the detectable moiety; and (ii) contacting the first complex with the signal amplification complex. In embodiments, the detectable moiety comprises multiple binding sites for the binding moiety and/or the binding moiety comprises multiple binding sites for the detectable moiety, and the signal amplification complex comprises a plurality of signal amplification reagents, and wherein each signal amplification reagent is bound to one or more detectable moieties. In embodiments, the first complex and the signal amplification complex are formed simultaneously or substantially simultaneously. In embodiments, the first complex and the signal amplification complex are formed sequentially. In embodiments, the first complex is formed on the surface, and the signal amplification complex is formed in a separate reaction vessel or container.

In embodiments where the binding moiety comprises an oligonucleotide binding moiety and the detectable moiety comprises a complementary oligonucleotide to the oligonucleotide binding moiety, the method further comprises increasing the length of the oligonucleotide binding moiety prior to binding to the detectable moiety. In embodiments, increasing the length of the oligonucleotide binding moiety comprises ligating the oligonucleotide binding moiety to a further oligonucleotide. In embodiments, increasing the length of the oligonucleotide binding moiety comprises hybridizing the oligonucleotide binding moiety to a further oligonucleotide, wherein at least a portion of the further oligonucleotide comprises a complementary sequence to the oligonucleotide binding moiety. In embodiments, the further oligonucleotide additionally comprises more than one complementary sequences to the labeled probe, thereby allowing more than one copy of the detectable moiety to bind to the second complex and further amplifying the assay signal, as described in embodiments herein.

An exemplary embodiment of the signal amplification complex, comprising a plurality of cross-linked signal amplification reagents and detectable moieties, wherein each detectable moiety comprises multiple second detectable labels, is illustrated in FIG. 4. In embodiments comprising forming a signal amplification complex and where the first and second detectable labels are the same, the signal amplification reagent specifically binds to the first detectable label and the conjugation linker of the detection reagent, thereby reducing binding of the signal amplification reagent to the second detectable label on the detectable moiety. In embodiments comprising forming a signal amplification complex, the first and second detectable labels are different, thereby reducing binding of the signal amplification reagent to the second detectable label on the detectable moiety.

In embodiments, the method comprises measuring the amount of the first and second detectable labels. In embodiments, the first and second detectable labels are detectably distinct, as described herein. In embodiments, the method comprises separately measuring the amounts of the first and second detectable labels. In embodiments, the first and second detectable labels are measured by light scattering, optical absorbance, fluorescence, chemiluminescence, electrochemiluminescence, bioluminescence, phosphorescence, radioactivity, magnetic field, or combination thereof. In embodiments, the first and second detectable labels each comprises an ECL label, and measuring the amount of the first and second detectable labels comprises measuring an ECL signal. In embodiments, the amount of measured ECL signal is used to detect the presence of the analyte in the sample. In embodiments, the amount of measured ECL signal is used to determine the amount of analyte in the sample.

In embodiments, the method comprises measuring the amount of the second detectable label. In embodiments, the second detectable label is measured by light scattering, optical absorbance, fluorescence, chemiluminescence, electrochemiluminescence, bioluminescence, phosphorescence, radioactivity, magnetic field, or combination thereof. In embodiments, the second detectable label comprises an ECL label, and measuring the amount of the second detectable label comprises measuring an ECL signal. In embodiments, the amount of measured ECL signal is used to detect the presence of the analyte in the sample. In embodiments, the amount of measured ECL signal is used to determine the amount of analyte in the sample.

I.B. Signal Amplification Reagent Comprising Enzyme

In embodiments, the first complex comprising the capture reagent, the analyte, and the detection reagent is contacted with: (1) a signal amplification reagent that specifically binds to the first detectable label and that comprises an enzyme, and (2) a substrate of the enzyme. In embodiments, the first complex comprises first and second detection reagents that each comprises a first detectable label, and the signal amplification reagent specifically binds to the first detectable label on the first detection reagent and to the first detectable label on the second detection reagent, as described herein.

In embodiments, the signal amplification reagent comprises an enzyme that acts upon a substrate. In embodiments, the enzyme is horseradish peroxidase (HRP), alkaline phosphatase (AP), β-galactosidase, glucose oxidase (GO), acetylcholinesterase, catalase, or β-lactamase.

In embodiments, the signal amplification reagent comprises an enzyme that acts upon a substrate, e.g., as illustrated in FIG. 17. In embodiments, the enzyme binds to and acts upon the substrate, e.g., via oxidation, reduction, hydrolysis, or combination thereof, to produce a detectable signal. In embodiments, the detectable signal comprises a chromogenic signal, chemiluminescence, fluorescence, or a combination thereof. In embodiments, the enzyme is HRP, AP, or β-galactosidase. In embodiments, the enzyme is HRP, and the substrate is 3,3',5,5'-tetramethylbenzidine (TMB), 2,2'-Azinobis [3-ethylbenzothiazoline-6-sulfonic acid]-diammonium salt (ABTS), or o-phenylenediamine dihydrochloride (OPD). In embodiments, TMB is converted from colorless to blue upon oxidation by HRP. In embodiments, ABTS is converted from colorless to green upon oxidation by HRP. In embodiments, OPD is converted from colorless to yellow-orange upon oxidation by HRP. In embodiments, the enzyme is AP, and the substrate is p-nitrophenyl phosphate (PNPP). In embodiments, PNPP is converted from colorless to yellow upon hydrolysis by AP. In embodiments, the enzyme is β-galactosidase, and the substrate is o-nitrophenyl-β-D-galactopyranoside (ONPG). In embodiments, ONPG is converted from colorless to yellow upon hydrolysis by β-galactosidase. Further non-limiting examples of substrates for HRP include chemiluminescent substrates such as SUPERSIGNAL™, and fluorescent substrates such as QUANTABLU™, QUANTARED™, and AMPLEX™ Red. Further non-limiting examples of substrates for AP include the chemiluminescent substrates CDP™ and DYNALIGHT™. Methods of detecting the substrates described herein are known in the art and described, e.g., by Crowther, J. R. "The ELISA Guidebook." Methods in Molecular Biology. Humana Press; Totowa, NJ (2001).

In embodiments, the method comprises measuring activity of the enzyme. In embodiments, the measuring comprises measuring the detectable signal produced upon the enzyme acting upon the substrate. In embodiments, the detectable signal is measured by light scattering, optical absorbance, fluorescence, chemiluminescence, electrochemiluminescence, bioluminescence, phosphorescence, radioactivity, magnetic field, or combination thereof. In embodiments, the substrate is TMBM, ABTS, OPD, PNPP, or ONPG and produces a chromogenic signal upon reacting with the enzyme. In embodiments, the substrate produces a fluorescent signal upon reacting with the enzyme. In embodiments, the substrate produces a chemiluminescent signal upon reacting with the enzyme. In embodiments, the amount of measured detectable signal is used to determine the presence of the analyte in the sample. In embodiments, the amount of measured detectable signal is used to determine the amount of analyte in the sample.

I.C. Signal Amplification Reagent Comprising Second Detectable Label

In embodiments, the first complex comprising the capture reagent, the analyte, and the detection reagent is contacted with a signal amplification reagent that specifically binds to the first detectable label and that comprises a second detectable label. In embodiments, the first complex comprises first and second detection reagents that each comprises a first detectable label, and the signal amplification reagent specifically binds to the first detectable label on the first detection reagent and to the first detectable label on the second detection reagent, as described herein and as depicted in FIG. 22C.

Second detectable labels are further described herein. In embodiments, the second detectable label is capable of being detected by light scattering, optical absorbance, fluorescence, chemiluminescence, electrochemiluminescence, bioluminescence, phosphorescence, radioactivity, magnetic field, or combination thereof. In embodiments, the second detectable label comprises an ECL label as described herein. In embodiments, the ECL label comprises an organometallic complex comprising at least one substituted bipyridine ligand, wherein the substituted bipyridine ligand comprises at least one sulfonate group. In embodiments, the ECL label comprises an organometallic complex comprising at least two substituted bipyridine ligands, wherein each substituted bipyridine ligand comprises at least one sulfonate group. In embodiments, the substituted bipyridine ligand is a compound of Formula I. In embodiments, the ECL label comprises three ligands, wherein a first ligand is a compound of Formula I, and wherein a second ligand comprises a bipyridine having at least one substituent that is covalently linked to the labeled probe. In embodiments, the ECL label comprises an organometallic complex that comprises three ligands, wherein two of the ligands are each a compound of Formula I, and wherein the third ligand comprises a bipyridine having at least one substituent that is covalently linked to the labeled probe. In embodiments, the organometallic complex comprises ruthenium, osmium, or rhenium.

In embodiments, the second detectable label comprises a compound of Formula II. In embodiments, the second detectable label comprises a compound of Formula III. In embodiments, the second detectable label comprises a compound of Formula IV. In embodiments, the second detectable label comprises a compound of Formula V. In embodiments, the second detectable label comprises a compound of Formula VI.

In embodiments, the first detectable label of the detection reagent (e.g., first and/or second detection reagents) and second detectable label of the signal amplification reagent are the same. In embodiments, the first and second detectable labels each comprises an ECL label as described herein. In embodiments, the first and second detectable labels each comprises a compound of Formula II. In embodiments, the first and second detectable labels each comprises a compound of Formula III. In embodiments, the first and second detectable labels each comprises a compound of Formula IV. In embodiments, the first and second detectable labels each comprises a compound of Formula V. In embodiments, the first and second detectable labels each comprises a compound of Formula VI.

In embodiments, the first and second detectable labels are different. In embodiments, the first detectable label is not detectable once it is bound by the signal amplification reagent. In embodiments, the signal amplification reagent specifically binds to the first detectable label, and not the second detectable label. In embodiments, the first detectable label comprises a compound of Formula II, and the second detectable label comprises a compound of any one of Formulas III, IV, V, or VI. In embodiments, the first detectable label comprises a compound of Formula III, and the second detectable label comprises a compound of any one of Formulas II, IV, V, or VI. In embodiments, the first detectable label comprises a compound of Formula IV, and the second detectable label comprises a compound of any one of Formulas II, III, V, or VI. In embodiments, the first detectable label comprises a compound of Formula V, and the second detectable label comprises a compound of any one of Formulas II, III, IV, or VI. In embodiments, the first detectable label comprises a compound of Formula VI, and the second detectable label comprises a compound of any one of Formulas II, III, IV, or V. In embodiments, the first detectable label is detectably distinct from the second detectable label as described herein.

In embodiments, the method comprises measuring the amount of the first and second detectable labels. In embodiments, the first and second detectable labels are detectably distinct, as described herein. In embodiments, the method comprises separately measuring the amounts of the first and second detectable labels. In embodiments, the first and second detectable labels are measured by light scattering, optical absorbance, fluorescence, chemiluminescence, electrochemiluminescence, bioluminescence, phosphorescence, radioactivity, magnetic field, or combination thereof. In embodiments, the first and second detectable labels each comprises an ECL label, and measuring the amount of the first and second detectable labels comprises measuring an ECL signal. In embodiments, the amount of measured ECL signal is used to detect the presence of the analyte in the sample. In embodiments, the amount of measured ECL signal is used to determine the amount of analyte in the sample.

In embodiments, the method comprises measuring the amount of the second detectable label. In embodiments, the second detectable label is measured by light scattering, optical absorbance, fluorescence, chemiluminescence, electrochemiluminescence, bioluminescence, phosphorescence, radioactivity, magnetic field, or combination thereof. In embodiments, the second detectable label comprises an ECL label, and measuring the amount of the second detectable label comprises measuring an ECL signal. In embodiments, the amount of measured ECL signal is used to detect the presence of the analyte in the sample. In embodiments, the amount of measured ECL signal is used to determine the amount of analyte in the sample.

I.D. Signal Amplification Reagent Comprising Nucleic Acid Probe

In embodiments, the first complex comprising the capture reagent, the analyte, and the detection reagent is contacted with a signal amplification reagent that specifically binds to the first detectable label and that comprises a nucleic acid probe. In embodiments, the first complex comprises first and second detection reagents that each comprises a first detectable label, and the signal amplification reagent specifically binds to the first detectable label on the first detection reagent and to the first detectable label on the second detection reagent, as described herein and as shown in FIG. 22D. In embodiments, the method comprises forming a second complex on the surface comprising the first complex and the signal amplification reagent.

In embodiments, the first complex comprises at least two first detectable labels, e.g., that are present on first and second detection reagents as described herein, or that are present on a single detection reagent as described herein. In embodiments, the method comprises contacting the first complex with at least two signal amplification reagents. In embodiments, the signal amplification reagent of the second complex as described herein is a first signal amplification reagent, and the second complex further comprises a second signal amplification reagent, wherein the first and second signal amplification reagents each binds to a distinct first detectable label present on one or more detection reagents. In embodiments, the second complex comprises at least two signal amplification reagents, wherein each signal amplification reagent comprises a nucleic acid probe, e.g., as shown in FIG. 1C (showing three signal amplification reagents bound to a detection reagent) and FIG. 1D (showing two signal amplification reagents bound to a detection reagent). Thus, in embodiments, the second complex comprises one or more nucleic acid probes. In embodiments, each nucleic acid probe of the second complex comprises a same sequence. In embodiments, each nucleic acid probe of the second complex consists of a same sequence. In embodiments, each nucleic acid probe of the second complex comprise different sequences. In embodiments, two or more of the nucleic acid probes of the second complex comprises a same sequence.

In embodiments, the method comprises extending the nucleic acid probe (e.g., each nucleic acid probe of the second complex) to form an extended sequence. In embodiments, the extending comprises ligating the nucleic acid probe (e.g., each nucleic acid probe of the second complex) to a further oligonucleotide to form an extended sequence. In embodiments, the extending comprises hybridizing the nucleic acid probe (e.g., each nucleic acid probe of the second complex) to a further oligonucleotide, wherein at least a portion of the further oligonucleotide comprises a complementary sequence to the nucleic acid probe, to form an extended sequence.

In embodiments, the extending comprises binding the nucleic acid probe (e.g., each nucleic acid probe of the second complex) to a template oligonucleotide for an extension reaction to form an extended sequence. In embodiments, the second complex comprises multiple, e.g., at least two, nucleic acid probes, and the extending comprises binding each nucleic acid probe to a distinct template oligonucleotide and extending each nucleic acid probe to form multiple, e.g., at least two, extended sequences. In embodiments, the second complex comprises multiple, e.g., at least two, nucleic acid probes, and the extending comprises binding two nucleic acid probes to a single template oligonucleotide and extending one or both nucleic acid probes to form an extended sequence. In embodiments, the second complex comprises multiple, e.g., at least two, nucleic acid probes, and the extending comprises binding two nucleic acid probes to two template oligonucleotides, wherein each template oligonucleotide binds to a portion of each of the two nucleic acid probes, and extending one or both nucleic acid probes to form an extended sequence.

In embodiments, the nucleic acid probe is a primer for the extension reaction. In embodiments, the extension reaction comprises PCR, LCR, SDA, 3SR, isothermal amplification (such as, e.g., helicase-dependent amplification or rolling circle amplification), or combination thereof. In embodiments, the extending comprises binding the nucleic acid probe to a template oligonucleotide and extending the nucleic acid probe by PCR, LCR, SDA, 3SR, isothermal amplification (such as, e.g., helicase-dependent amplification or rolling circle amplification), or combination thereof. In embodiments, the extending comprises binding the nucleic acid probe to a template oligonucleotide and extending the nucleic acid probe by PCR. In embodiments, the extending comprises binding the nucleic acid probe to a template oligonucleotide, forming a circular template oligonucleotide (e.g., by ligation of a linear template oligonucleotide), and extending the nucleic acid probe by rolling circle amplification.

In embodiments, the second complex comprises at least two nucleic acid probes, and the extending comprises: binding each nucleic acid probe to a distinct template oligonucleotide, forming a circular template from each template oligonucleotide, and extending each nucleic acid probe by RCA, e.g., as shown in FIG. 1C. In embodiments, the second complex comprises two nucleic acid probes, and the extending comprises: contacting the two nucleic acid probes with two template oligonucleotides, wherein each template oligonucleotide binds simultaneously to a portion of each of the two nucleic acid probes; ligating the two template oligonucleotides to form a circular template; and extending one or both of the nucleic acid probes by RCA, e.g., as shown in FIG. 1D.

In embodiments, the second complex comprises first and second signal amplification reagents, and the nucleic acid probes of the first and second signal amplification reagents comprise or consist of a same sequence. In embodiments, the nucleic acid probes of the first and second signal amplification reagents comprise different sequences. In embodiments where the nucleic acid probes of the first and second signal amplification reagents comprise different sequences, the template oligonucleotide is capable of being ligated when the two nucleic acid probes are in proximity, thereby increasing specificity of the method for detecting the analyte.

In embodiments, the second complex comprises at least two nucleic acid probes comprising different sequences. In embodiments, the two nucleic acid probes bind to adjacent regions of a template oligonucleotide. In embodiments, the template oligonucleotide comprises an interior sequence that is complementary to a first of the two nucleic acid probes; and 5' and 3' sequences complementary to non-overlapping regions of a second of the two nucleic acid probes. In embodiments, the two nucleic acid probes are contacted with: a first template oligonucleotide comprising a sequence complementary to a first region on a first of the two nucleic acid probes and a first region on a second of the two nucleic acid probes; and a second template oligonucleotide comprising a sequence complementary to a second region on the first of the two nucleic acid probes and a second region on the second of the two nucleic acid probes, wherein the first regions and the second regions on each nucleic acid probe are non-overlapping; ligating the first and second template oligonucleotides to form a circular template; and extending one or both nucleic acid probes by RCA to form an extended sequence.

In embodiments, the extended sequence comprises an anchoring region that is capable of binding to an anchoring reagent. In embodiments, the first complex is on a surface, and the method further comprises immobilizing an anchoring reagent on the surface. In embodiments, the first complex is on a surface, and the surface further comprises an immobilized anchoring reagent. In embodiments, the anchoring reagent is immobilized to the surface via a thioester, thioether, disulfide, or combination thereof. In embodiments, the anchoring reagent is immobilized to the surface via a targeting agent as further described herein. In embodiments, the anchoring reagent is immobilized to the surface before, during, or after formation of the first complex described herein. In embodiments, the anchoring reagent is immobilized to the surface before step (a) of the method. In embodiments, the anchoring reagent is immobilized to the surface prior to forming the extended sequence. In embodiments, the anchoring reagent is immobilized to the surface prior to measuring the amount of extended sequence. In embodiments, the method comprises binding the anchoring region of the extended sequence to the anchoring reagent. In embodiments, the measuring comprises measuring the amount of extended sequence bound to the surface via the anchoring reagent.

In embodiments, the anchoring reagent comprises an oligonucleotide, aptamer, aptamer ligand, antibody, antigen, ligand, receptor, hapten, epitope, or mimotope. In embodiments, the anchoring reagent comprises an aptamer ligand, and the anchoring region of the extended sequence comprises an aptamer. In embodiments, the anchoring reagent comprises an oligonucleotide-binding protein, and the anchoring region of the extended sequence comprises an oligonucleotide sequence. In embodiments, the anchoring reagent comprises a single stranded oligonucleotide. In embodiments, the anchoring reagent comprises a double stranded oligonucleotide. In embodiments, the anchoring reagent and the anchoring region comprise complementary oligonucleotides. In embodiments, the anchoring reagent comprises an anchoring oligonucleotide. In embodiments, the anchoring region of the extended sequence comprises an anchoring oligonucleotide complement that is complementary to the anchoring oligonucleotide.

In embodiments, binding the extended sequence to the anchoring reagent comprises forming a triple helix between the anchoring reagent and the anchoring region of the extended sequence. In embodiments, binding the extended sequence to the anchoring reagent comprises denaturing the anchoring region to expose a single stranded oligonucleotide region prior to the binding; exposing the anchoring region to helicase activity prior to the binding; and/or exposing the anchoring region to nuclease treatment prior to the binding, wherein the anchoring region comprises one or more hapten-modified bases and the anchoring reagent comprises one or more antibodies specific for the hapten; and/or the anchoring region comprises one or more ligand-modified bases and the anchoring reagent comprises one or more receptors specific for the ligand.

In embodiments, the first complex comprises the analyte, a capture reagent, and a detection reagent, as described herein. In embodiments, the first complex comprises the analyte, a capture reagent, a first detection reagent, and a second detection reagent, as described herein. In embodiments, the second complex comprises the capture reagent, the analyte, the detection reagent, and the signal amplification reagent. In embodiments, the second complex comprises the capture reagent, the analyte, the first detection reagent, the second detection reagent, and the signal amplification reagent. In embodiments, the second complex is bound to the surface following the extending of the labeled probe. In embodiments, the second complex is bound to the surface prior to being contacted with the labeled probe. In embodiments, the extended sequence binds to the anchoring reagent at a position within about 1 nm to about 500 nm, about 5 nm to about 250 nm, about 10 nm to about 200 nm, or about 15 nm to about 150 nm from the second complex on the surface. In embodiments, the extended sequence binds to the anchoring reagent at a position less than 1 μm from the second complex on the surface. In embodiments, the extended sequence binds to the anchoring reagent at a position less than 500 nm from the second complex on the surface. In embodiments, the extended sequence binds to the anchoring reagent at a position less than 200 nm from the second complex on the surface.

In embodiments, measuring the amount of extended sequence comprises contacting the extended sequence with a labeled probe comprising a second detectable label. In embodiments, the labeled probe comprises more than one of the second detectable label. In embodiments, the labeled probe comprises 1, 2, 3, 4, 5, 6, 7, 8, 9, 10, or more than 10 of the second detectable label. In embodiments, the labeled probe comprising the second detectable label binds to the extended sequence. In embodiments, the extended sequence and the labeled probe comprise complementary oligonucleotides. In embodiments, the extended sequence comprises a modified base, and measuring the amount of extended sequence comprises contacting the extended sequence with a detectable moiety that binds to the modified base. In embodiments, the modified base comprises an aptamer, aptamer ligand, antibody, antigen, ligand, receptor, hapten, epitope, or mimotope, and the detectable moiety comprises a binding partner of the modified base and a second detectable label. In embodiments, the modified base comprises streptavidin or avidin, and the detectable moiety comprises biotin and a second detectable label. In embodiments, the modified base comprises biotin, and the detectable moiety comprises avidin and a second detectable label.

Second detectable labels are further described herein. In embodiments, the second detectable label is capable of being detected by light scattering, optical absorbance, fluorescence, chemiluminescence, electrochemiluminescence, bioluminescence, phosphorescence, radioactivity, magnetic field, or combination thereof. In embodiments, the second detectable label comprises an ECL label as described herein. In embodiments, the ECL label comprises an organometallic complex comprising at least one substituted bipyridine ligand, wherein the substituted bipyridine ligand comprises at least one sulfonate group. In embodiments, the ECL label comprises an organometallic complex comprising at least two substituted bipyridine ligands, wherein each substituted bipyridine ligand comprises at least one sulfonate group. In embodiments, the substituted bipyridine ligand is a compound of Formula I. In embodiments, the ECL label comprises three ligands, wherein a first ligand is a compound of Formula I, and wherein a second ligand comprises a bipyridine having at least one substituent that is covalently linked to the labeled probe. In embodiments, the ECL label comprises an organometallic complex that comprises three ligands, wherein two of the ligands are each a compound of Formula I, and wherein the third ligand comprises a bipyridine having at least one substituent that is covalently linked to the labeled probe. In embodiments, the organometallic complex comprises ruthenium, osmium, or rhenium.

In embodiments, the second detectable label comprises a compound of Formula II. In embodiments, the second detectable label comprises a compound of Formula III. In embodiments, the second detectable label comprises a compound of Formula IV. In embodiments, the second detectable label comprises a compound of Formula V. In embodiments, the second detectable label comprises a compound of Formula VI.

In embodiments, the first detectable label of the detection reagent (e.g., first and/or second detection reagents) and the second detectable label of the labeled probe are the same. In embodiments, the first and second detectable labels each comprises an ECL label as described herein. In embodiments, the first and second detectable labels each comprises a compound of Formula II. In embodiments, the first and second detectable labels each comprises a compound of Formula III. In embodiments, the first and second detectable labels each comprises a compound of Formula IV. In embodiments, the first and second detectable labels each comprises a compound of Formula V. In embodiments, the first and second detectable labels each comprises a compound of Formula VI.

In embodiments, the first and second detectable labels are different. In embodiments, the first detectable label is not detectable once it is bound by the signal amplification reagent. In embodiments, the signal amplification reagent specifically binds to the first detectable label, and not the second detectable label. In embodiments, the first detectable label comprises a compound of Formula II, and the second detectable label comprises a compound of any one of Formulas III, IV, V, or VI. In embodiments, the first detectable label comprises a compound of Formula III, and the second detectable label comprises a compound of any one of Formulas II, IV, V, or VI. In embodiments, the first detectable label comprises a compound of Formula IV, and the second detectable label comprises a compound of any one of Formulas II, III, V, or VI. In embodiments, the first detectable label comprises a compound of Formula V, and the second detectable label comprises a compound of any one of Formulas II, III, IV, or VI. In embodiments, the first detectable label comprises a compound of Formula VI, and the second detectable label comprises a compound of any one of Formulas II, III, IV, or V. In embodiments, the first detectable label is detectably distinct from the second detectable label as described herein.

In embodiments, the method comprises measuring the amount of extended sequence by measuring the amount of the second detectable label on the surface. In embodiments, the second detectable label is measured by light scattering, optical absorbance, fluorescence, chemiluminescence, electrochemiluminescence, bioluminescence, phosphorescence, radioactivity, magnetic field, or combination thereof. In embodiments, the second detectable label comprises an ECL label, and measuring the amount of the second detectable label comprises measuring an ECL signal. In embodiments, the amount of measured ECL signal is used to detect the presence of the analyte in the sample. In embodiments, the amount of measured ECL signal is used to determine the amount of analyte in the sample.

In embodiments, the method further comprises measuring the amount of the first and second detectable labels on the surface. In embodiments, the first and second detectable labels are detectably distinct, as described herein. In embodiments, the method comprises separately measuring the amounts of the first and second detectable labels. In embodiments, the first and second detectable labels are measured by light scattering, optical absorbance, fluorescence, chemiluminescence, electrochemiluminescence, bioluminescence, phosphorescence, radioactivity, magnetic field, or combination thereof. In embodiments, the first and second detectable labels each comprises an ECL label, and measuring the amount of the first and second detectable labels comprises measuring an ECL signal. In embodiments, the amount of measured ECL signal is used to detect the presence of the analyte in the sample. In embodiments, the amount of measured ECL signal is used to determine the amount of analyte in the sample.

II. Signal Amplification of a Detection Reagent Comprising First Nucleic Acid Probe In embodiments, the invention provides a method of detecting an analyte of interest in a sample, comprising forming a first complex on a surface, wherein the first complex comprises the analyte of interest, a capture reagent that specifically binds the analyte, and a detection reagent that specifically binds the analyte, wherein the detection reagent comprises a first nucleic acid probe;

extending the first nucleic acid probe to form a first extended sequence comprising a first anchoring region, wherein the first anchoring region binds a first anchoring reagent that is immobilized on the surface;

binding the first extended sequence to a first labeled probe comprising a first detectable label; and contacting the first labeled probe with a signal amplification reagent. In embodiments, the first detectable label is an ECL label. Detection reagents comprising first nucleic acid probes; extension of the first nucleic acid probe to form a first extended sequence; and binding of first labeled probes to a first extended sequence are further described herein.

In embodiments, the first complex is formed by: contacting the analyte of interest with (i) the surface; (ii) the capture reagent; and (iii) the detection reagent. In embodiments, the first complex is formed by: contacting the sample with (i) the surface; (ii) the capture reagent; and (iii) the detection reagent.

In embodiments, the detection reagent of the first complex is a first detection reagent, and the first complex further comprises a second detection reagent, wherein each of the first and second detection reagents comprises a proximity nucleic acid probe as described herein. In embodiments, one or both of the proximity nucleic acid probes is extended to form the first extended sequence comprising the first anchoring region as described herein. In embodiments, the first complex is formed by: contacting the analyte of interest and/or the sample with (i) the surface; (ii) the capture reagent; (iii) the first detection reagent; and (iv) the second detection reagent. As described herein, the capture reagent and the first and second detection reagents may be contacted with the sample and/or the analyte in any order.

In embodiments, the capture reagent is immobilized on the surface, as described herein. In embodiments, the capture reagent is capable of being immobilized on the surface. In embodiments, the method comprises immobilizing the capture reagent to the surface before, during, or after formation of the first complex. In embodiments, the method comprises immobilizing the capture reagent to the surface prior to step (a) of the method. Methods of immobilizing capture reagents to surfaces are provided herein.

In embodiments, the method further comprises, prior to contacting the first labeled probe with the signal amplification reagent, detecting the first complex on the surface. In embodiments, the detecting comprises measuring the amount of the first extended sequence bound to the surface. In embodiments, the detecting comprises measuring the amount of the first labeled probe bound to the first extended sequence. In embodiments, the detecting comprises measuring the amount of the first detectable label of the first labeled probe. In embodiments, the first detectable label is measured by light scattering, optical absorbance, fluorescence, chemiluminescence, electrochemiluminescence, bioluminescence, phosphorescence, radioactivity, magnetic field, or combination thereof. In embodiments, the first detectable label comprises an ECL label, and measuring the amount of the first detectable label comprises measuring an ECL signal.

In embodiments, the first labeled probe comprises multiple first detectable labels, and multiple signal amplification reagents bind to the first labeled probe, wherein each signal amplification reagent binds to a separate first detectable label on the detection reagent. In embodiments, the first extended sequence binds multiple first labeled probes, and a separate signal amplification reagent binds to each of the multiple first labeled probes.

II.A. Signal Amplification Reagent Comprising Binding Moiety

In embodiments, the first labeled probe is contacted with: (1) a signal amplification reagent comprising a binding moiety, and (2) a detectable moiety, wherein the detectable moiety comprises: (i) a binding partner of the binding moiety and (ii) one or more of a second detectable label.

In embodiments, the binding moiety comprises an oligonucleotide, and the detectable moiety comprises a complementary oligonucleotide. In embodiments, the binding moiety and the detectable moiety comprise a receptor-ligand pair, an antigen-antibody pair, a hapten-antibody pair, an epitope-antibody pair, a mimotope-antibody pair, an aptamer-target molecule pair, an intercalator-target molecule pair, or an enzyme-substrate pair. In embodiments, the binding moiety comprises multiple binding sites for the detectable moiety. In embodiments, the binding moiety comprises 2, 3, 4, 5, 6, 7, 8, 9, or 10 binding sites for the detectable moiety. In embodiments, the detectable moiety comprises multiple binding sites for the binding moiety. In embodiments, the detectable moiety comprises 2, 3, 4, 5, 6, 7, 8, 9, or 10 binding sites for the binding moiety. For example, one streptavidin is capable of binding four biotin molecules. In embodiments, the binding moiety comprises biotin, and the detectable moiety comprises avidin or streptavidin. In embodiments, the binding moiety comprises avidin or streptavidin, and the detectable moiety comprises biotin.

In embodiments, the detectable moiety comprises a second detectable label. In embodiments, the detectable moiety comprises more than one of the second detectable label. In embodiments, the detectable moiety comprises 1, 2, 3, 4, 5, 6, 7, 8, 9, 10, or more than 10 of the second detectable label.

In embodiments, the second detectable label is capable of being detected by light scattering, optical absorbance, fluorescence, chemiluminescence, electrochemiluminescence, bioluminescence, phosphorescence, radioactivity, magnetic field, or combination thereof. In embodiments, the second detectable label comprises an ECL label as described herein. In embodiments, the ECL label comprises an organometallic complex comprising at least one substituted bipyridine ligand, wherein the substituted bipyridine ligand comprises at least one sulfonate group. In embodiments, the ECL label comprises an organometallic complex comprising at least two substituted bipyridine ligands, wherein each substituted bipyridine ligand comprises at least one sulfonate group. In embodiments, the substituted bipyridine ligand is a compound of Formula I. In embodiments, the ECL label comprises three ligands, wherein a first ligand is a compound of Formula I, and wherein a second ligand comprises a bipyridine having at least one substituent that is covalently linked to the detectable moiety. In embodiments, the ECL label comprises an organometallic complex that comprises three ligands, wherein two of the ligands are each a compound of Formula I, and wherein the third ligand comprises a bipyridine having at least one substituent that is covalently linked to the detectable moiety. In embodiments, the organometallic complex comprises ruthenium, osmium, or rhenium.

In embodiments, the second detectable label comprises a compound of Formula II. In embodiments, the second detectable label comprises a compound of Formula III. In embodiments, the second detectable label comprises a compound of Formula IV. In embodiments, the second detectable label comprises a compound of Formula V. In embodiments, the second detectable label comprises a compound of Formula VI.

In embodiments, the first detectable label of the first labeled probe and second detectable label of the detectable moiety are the same. In embodiments, the first and second detectable labels each comprises an ECL label as described herein. In embodiments, the first and second detectable labels each comprises a compound of Formula II. In embodiments, the first and second detectable labels each comprises a compound of Formula III. In embodiments, the first and second detectable labels each comprises a compound of Formula IV. In embodiments, the first and second detectable labels each comprises a compound of Formula V. In embodiments, the first and second detectable labels each comprises a compound of Formula VI.

In embodiments, the first and second detectable labels are different. In embodiments, the first detectable label is not detectable once it is bound by the signal amplification reagent. In embodiments, the signal amplification reagent specifically binds to the first detectable label, and not the second detectable label. In embodiments, the first detectable label comprises a compound of Formula II, and the second detectable label comprises a compound of any one of Formulas III, IV, V, or VI. In embodiments, the first detectable label comprises a compound of Formula III, and the second detectable label comprises a compound of any one of Formulas II, IV, V, or VI. In embodiments, the first detectable label comprises a compound of Formula IV, and the second detectable label comprises a compound of any one of Formulas II, III, V, or VI. In embodiments, the first detectable label comprises a compound of Formula V, and the second detectable label comprises a compound of any one of Formulas II, III, IV, or VI. In embodiments, the first detectable label comprises a compound of Formula VI, and the second detectable label comprises a compound of any one of Formulas II, III, IV, or V. In embodiments, the first detectable label is detectably distinct from the second detectable label as described herein.

In embodiments, the first labeled probe is first contacted with the signal amplification reagent, then contacted with the detectable moiety. In embodiments, the first labeled probe is contacted with the signal amplification reagent and the detectable moiety simultaneously or substantially simultaneously.

In embodiments, the contacting comprises: (i) forming a signal amplification complex comprising the signal amplification reagent and the detectable moiety; and (ii) contacting the first labeled probe with the signal amplification complex. In embodiments, the detectable moiety comprises multiple binding sites for the binding moiety and/or the binding moiety comprises multiple binding sites for the detectable moiety, and the signal amplification complex comprises a plurality of signal amplification reagents, and wherein each signal amplification reagent is bound to one or more detectable moieties. In embodiments, the first complex and the signal amplification complex are formed simultaneously or substantially simultaneously. In embodiments, the first complex and the signal amplification complex are formed sequentially. In embodiments, the first complex is formed on the surface, and the signal amplification complex is formed in a separate reaction vessel or container.

In embodiments where the binding moiety comprises an oligonucleotide binding moiety and the detectable moiety comprises a complementary oligonucleotide to the oligonucleotide binding moiety, the method further comprises increasing the length of the oligonucleotide binding moiety prior to binding to the detectable moiety. In embodiments, increasing the length of the oligonucleotide binding moiety comprises ligating the oligonucleotide binding moiety to a further oligonucleotide. In embodiments, increasing the length of the oligonucleotide binding moiety comprises hybridizing the oligonucleotide binding moiety to a further oligonucleotide, wherein at least a portion of the further oligonucleotide comprises a complementary sequence to the oligonucleotide binding moiety. In embodiments, the further oligonucleotide comprises more than one complementary sequences to the detectable moiety, thereby allowing more than one copy of the detectable moiety to bind to the second complex and further amplifying the assay signal, as described in embodiments herein.

In embodiments, the method comprises measuring the amount of the first and second detectable labels on the surface. In embodiments, the first and second detectable labels are detectably distinct, as described herein. In embodiments, the method comprises separately measuring the amounts of the first and second detectable labels. In embodiments, the first and second detectable labels are measured by light scattering, optical absorbance, fluorescence, chemiluminescence, electrochemiluminescence, bioluminescence, phosphorescence, radioactivity, magnetic field, or combination thereof. In embodiments, the first and second detectable labels each comprises an ECL label, and measuring the amount of the first and second detectable labels comprises measuring an ECL signal. In embodiments, the amount of measured ECL signal is used to detect the presence of the analyte in the sample. In embodiments, the amount of measured ECL signal is used to determine the amount of analyte in the sample.

In embodiments, the method comprises measuring the amount of the second detectable label on the surface. In embodiments, the second detectable label is measured by light scattering, optical absorbance, fluorescence, chemiluminescence, electrochemiluminescence, bioluminescence, phosphorescence, radioactivity, magnetic field, or combination thereof. In embodiments, the second detectable label comprises an ECL label, and measuring the amount of the second detectable label comprises measuring an ECL signal. In embodiments, the amount of measured ECL signal is used to detect the presence of the analyte in the sample. In embodiments, the amount of measured ECL signal is used to determine the amount of analyte in the sample.

II.B. Signal Amplification Reagent Comprising Enzyme

In embodiments, the first labeled probe is contacted with: (1) a signal amplification reagent that specifically binds to the first detectable label and that comprises an enzyme, and (2) a substrate of the enzyme.

In embodiments, the signal amplification reagent comprises an enzyme that acts upon a substrate. In embodiments, the enzyme is horseradish peroxidase (HRP), alkaline phosphatase (AP), β-galactosidase, glucose oxidase (GO), acetylcholinesterase, catalase, or β-lactamase.

In embodiments, the signal amplification reagent comprises an enzyme that acts upon a substrate for the enzyme. In embodiments, the enzyme binds to and acts upon the substrate, e.g., via oxidation, reduction, hydrolysis, or combination thereof, to produce a detectable signal. In embodiments, the detectable signal comprises a chromogenic signal, chemiluminescence, fluorescence, or a combination thereof. In embodiments, the enzyme is HRP, AP, or β-galactosidase. In embodiments, the enzyme is HRP, and the detectable moiety is TMB, ABTS, or OPD. In embodiments, the binding moiety is AP, and the detectable moiety is PNPP. In embodiments, the binding moiety is β-galactosidase, and the detectable moiety is ONPG. Further non-limiting examples of substrates for HRP include chemiluminescent substrates such as SUPERSIGNAL™, and fluorescent substrates such as QUANTABLU™, QUANTARED™, and AMPLEX™ Red. Further non-limiting examples of substrates for AP include the chemiluminescent substrates CDP™ and DYNALIGHT™. Detection methods for various enzyme substrates, including TMB, ABTS, OPD, PNPP, and ONPG, are further described herein.

In embodiments, the method comprises measuring activity of the enzyme. In embodiments, the measuring comprises measuring the detectable signal produced upon the enzyme acting upon the substrate. In embodiments, the detectable signal is measured by light scattering, optical absorbance, fluorescence, chemiluminescence, electrochemiluminescence, bioluminescence, phosphorescence, radioactivity, magnetic field, or combination thereof. In embodiments, the substrate is TMBM, ABTS, OPD, PNPP, or ONPG and produces a chromogenic signal upon reacting with the enzyme. In embodiments, the substrate produces a fluorescent signal upon reacting with the enzyme. In embodiments, the substrate produces a chemiluminescent signal upon reacting with the enzyme. In embodiments, the amount of measured detectable signal is used to determine the presence of the analyte in the sample. In embodiments, the amount of measured detectable signal is used to determine the amount of analyte in the sample.

II.C. Signal Amplification Reagent Comprising Second Detectable Label

In embodiments, the first labeled probe is contacted with a signal amplification reagent that specifically binds to the first detectable label and that comprises a second detectable label.

Second detectable labels are further described herein. In embodiments, the second detectable label is capable of being detected by light scattering, optical absorbance, fluorescence, chemiluminescence, electrochemiluminescence, bioluminescence, phosphorescence, radioactivity, magnetic field, or combination thereof. In embodiments, the second detectable label comprises an ECL label as described herein. In embodiments, the ECL label comprises an organometallic complex comprising at least one substituted bipyridine ligand, wherein the substituted bipyridine ligand comprises at least one sulfonate group. In embodiments, the ECL label comprises an organometallic complex comprising at least two substituted bipyridine ligands, wherein each substituted bipyridine ligand comprises at least one sulfonate group. In embodiments, the substituted bipyridine ligand is a compound of Formula I. In embodiments, the ECL label comprises three ligands, wherein a first ligand is a compound of Formula I, and wherein a second ligand comprises a bipyridine having at least one substituent that is covalently linked to the labeled probe. In embodiments, the ECL label comprises an organometallic complex that comprises three ligands, wherein two of the ligands are each a compound of Formula I, and wherein the third ligand comprises a bipyridine having at least one substituent that is covalently linked to the labeled probe. In embodiments, the organometallic complex comprises ruthenium, osmium, or rhenium.

In embodiments, the second detectable label comprises a compound of Formula II. In embodiments, the second detectable label comprises a compound of Formula III. In embodiments, the second detectable label comprises a compound of Formula IV. In embodiments, the second detectable label comprises a compound of Formula V. In embodiments, the second detectable label comprises a compound of Formula VI.

In embodiments, the first detectable label of the labeled probe and second detectable label of the signal amplification reagent are the same. In embodiments, the first and second detectable labels each comprises an ECL label as described herein. In embodiments, the first and second detectable labels each comprises a compound of Formula II. In embodiments, the first and second detectable labels each comprises a compound of Formula III. In embodiments, the first and second detectable labels each comprises a compound of Formula IV. In embodiments, the first and second detectable labels each comprises a compound of Formula V. In embodiments, the first and second detectable labels each comprises a compound of Formula VI.

In embodiments, the first and second detectable labels are different. In embodiments, the first detectable label is not detectable once it is bound by the signal amplification reagent. In embodiments, the signal amplification reagent specifically binds to the first detectable label, and not the second detectable label. In embodiments, the first detectable label comprises a compound of Formula II, and the second detectable label comprises a compound of any one of Formulas III, IV, V, or VI. In embodiments, the first detectable label comprises a compound of Formula III, and the second detectable label comprises a compound of any one of Formulas II, IV, V, or VI. In embodiments, the first detectable label comprises a compound of Formula IV, and the second detectable label comprises a compound of any one of Formulas II, III, V, or VI. In embodiments, the first detectable label comprises a compound of Formula V, and the second detectable label comprises a compound of any one of Formulas II, III, IV, or VI. In embodiments, the first detectable label comprises a compound of Formula VI, and the second detectable label comprises a compound of any one of Formulas II, III, IV, or V. In embodiments, the first detectable label is detectably distinct from the second detectable label as described herein.

In embodiments, the method comprises measuring the amount of the first and second detectable labels. In embodiments, the first and second detectable labels are detectably distinct, as described herein. In embodiments, the method comprises separately measuring the amounts of the first and second detectable labels. In embodiments, the first and second detectable labels are measured by light scattering, optical absorbance, fluorescence, chemiluminescence, electrochemiluminescence, bioluminescence, phosphorescence, radioactivity, magnetic field, or combination thereof. In embodiments, the first and second detectable labels each comprises an ECL label, and measuring the amount of the first and second detectable labels comprises measuring an ECL signal. In embodiments, the amount of measured ECL signal is used to detect the presence of the analyte in the sample. In embodiments, the amount of measured ECL signal is used to determine the amount of analyte in the sample.

In embodiments, the method comprises measuring the amount of the second detectable label. In embodiments, the second detectable label is measured by light scattering, optical absorbance, fluorescence, chemiluminescence, electrochemiluminescence, bioluminescence, phosphorescence, radioactivity, magnetic field, or combination thereof. In embodiments, the second detectable label comprises an ECL label, and measuring the amount of the second detectable label comprises measuring an ECL signal. In embodiments, the amount of measured ECL signal is used to detect the presence of the analyte in the sample. In embodiments, the amount of measured ECL signal is used to determine the amount of analyte in the sample.

II.D. Signal Amplification Reagent Comprising Second Nucleic Acid Probe

In embodiments, the first labeled probe is contacted with a signal amplification reagent that specifically binds to the first detectable label and that comprises a second nucleic acid probe. In embodiments, the method comprises forming a second complex on the surface comprising the first labeled probe and the signal amplification reagent.

In embodiments, the method comprises extending the second nucleic acid probe to form a second extended sequence. In embodiments, the extending comprises ligating the second nucleic acid probe to a further oligonucleotide to form a second extended sequence. In embodiments, the extending comprises hybridizing the second nucleic acid probe to a further oligonucleotide, wherein at least a portion of the further oligonucleotide comprises a complementary sequence to the second nucleic acid probe, to form a second extended sequence. In embodiments, the extending comprises binding the second nucleic acid probe to a template oligonucleotide for an extension reaction to form a second extended sequence. In embodiments, the second nucleic acid probe is a primer for the extension reaction. In embodiments, the extension reaction comprises PCR, LCR, SDA, 3SR, isothermal amplification (such as, e.g., helicase-dependent amplification or rolling circle amplification), or combination thereof. In embodiments, the extending comprises binding the second nucleic acid probe to a template oligonucleotide and extending the second nucleic acid probe by PCR, LCR, SDA, 3SR, isothermal amplification (such as, e.g., helicase-dependent amplification or rolling circle amplification), or combination thereof. In embodiments, the extending comprises binding the second nucleic acid probe to a template oligonucleotide and extending the second nucleic acid probe by PCR. In embodiments, the extending comprises binding the second nucleic acid probe to a template oligonucleotide, forming a circular template oligonucleotide (e.g., by ligation of a linear template oligonucleotide), and extending the second nucleic acid probe by rolling circle amplification.

In embodiments, the second extended sequence comprises a second anchoring region. In embodiments, the second anchoring region binds to a second anchoring reagent on the surface. In embodiments, the second anchoring reagent is immobilized on the surface before, during, or after formation of the first complex described herein. In embodiments, the second anchoring reagent is immobilized on the surface before, during, or after formation of the second complex described herein. In embodiments, the second anchoring reagent is immobilized to the surface before step (a) of the method. In embodiments, the second anchoring reagent is immobilized to the surface prior to forming the second extended sequence. In embodiments, the second anchoring reagent is immobilized to the surface prior to measuring the amount of the second extended sequence. In embodiments, the second anchoring reagent is immobilized to the surface via a thioester, thioether, disulfide, or combination thereof. In embodiments, the second anchoring reagent is immobilized to the surface via a targeting agent as further described herein.

In embodiments, the second anchoring reagent comprises an oligonucleotide, aptamer, aptamer ligand, antibody, antigen, ligand, receptor, hapten, epitope, or mimotope. In embodiments, the second anchoring reagent comprises an aptamer ligand, and the second anchoring region comprises an aptamer. In embodiments, the second anchoring reagent comprises an oligonucleotide-binding protein, and the second anchoring region comprises an oligonucleotide sequence. In embodiments, the second anchoring reagent comprises a single stranded oligonucleotide. In embodiments, the second anchoring reagent comprises a double stranded oligonucleotide. In embodiments, the second anchoring reagent and the second anchoring region comprise complementary oligonucleotides. In embodiments, the second anchoring reagent comprises a second anchoring oligonucleotide. In embodiments, the second anchoring region comprises a second anchoring oligonucleotide complement that is complementary to the second anchoring oligonucleotide.

In embodiments, binding the second extended sequence to the second anchoring reagent comprises forming a triple helix between the anchoring reagent and the second anchoring region. In embodiments, binding the second extended sequence to the second anchoring reagent comprises denaturing the second anchoring region to expose a single stranded oligonucleotide region prior to the binding; exposing the second anchoring region to helicase activity prior to the binding; and/or exposing the second anchoring region to nuclease treatment prior to the binding, wherein the second anchoring region comprises one or more hapten-modified bases and the second anchoring reagent comprises one or more antibodies specific for the hapten; and/or the second anchoring region comprises one or more ligand-modified bases and the second anchoring reagent comprises one or more receptors specific for the ligand.

In embodiments, the second extended sequence is bound to the second anchoring reagent prior to being contacted with the second labeled probe. In embodiments, the second complex is bound to the surface following extension of the second nucleic acid probe. In embodiments, the second extended sequence binds to the second anchoring reagent at a position within about 1 nm to about 500 nm, about 5 nm to about 250 nm, about 10 nm to about 200 nm, or about 15 nm to about 150 nm from the second complex on the surface. In embodiments, the second extended sequence binds to the second anchoring reagent at a position less than 1 μm from the second complex on the surface. In embodiments, the second extended sequence binds to the second anchoring reagent at a position less than 500 nm from the second complex on the surface. In embodiments, the second extended sequence binds to the second anchoring reagent at a position less than 200 nm from the second complex on the surface.

In embodiments, the first anchoring region and the second anchoring region comprise a same oligonucleotide sequence. In embodiments, the first anchoring region and the second anchoring region comprise different oligonucleotide sequences. In embodiments, the first anchoring reagent and the second anchoring reagent comprise a same oligonucleotide sequence. In embodiments, the first anchoring reagent and the second anchoring reagent comprise different oligonucleotide sequences. In embodiments, the first anchoring region and the second anchoring region bind to separate portions of a first and/or second anchoring reagent.

In embodiments, the method comprises measuring the amount of the first extended sequence, the second extended sequence, or both, on the surface. In embodiments, the second extended sequence is contacted with a second labeled probe comprising a second detectable label. In embodiments, the first labeled probe and the second labeled probe comprise a same oligonucleotide sequence. In embodiments, the first labeled probe and the second labeled probe comprise different oligonucleotide sequences.

In embodiments, the second labeled probe comprises more than one of the second detectable label. In embodiments, the second labeled probe comprises 1, 2, 3, 4, 5, 6, 7, 8, 9, 10, or more than 10 of the second detectable label. In embodiments, the second labeled probe comprising the second detectable label binds to the second extended sequence. In embodiments, the second extended sequence and the second labeled probe comprise complementary oligonucleotides. In embodiments, the second extended sequence comprises a modified base, and measuring the amount of extended sequence comprises contacting the extended sequence with a detectable moiety that binds to the modified base. In embodiments, the modified base comprises an aptamer, aptamer ligand, antibody, antigen, ligand, receptor, hapten, epitope, or mimotope, and the detectable moiety comprises a binding partner of the modified base and a second detectable label. In embodiments, the modified base comprises streptavidin or avidin, and the detectable moiety comprises biotin and a second detectable label. In embodiments, the modified base comprises biotin, and the detectable moiety comprises avidin and a second detectable label.

Second detectable labels are further described herein. In embodiments, the second detectable label is capable of being detected by light scattering, optical absorbance, fluorescence, chemiluminescence, electrochemiluminescence, bioluminescence, phosphorescence, radioactivity, magnetic field, or combination thereof. In embodiments, the second detectable label comprises an ECL label as described herein. In embodiments, the ECL label comprises an organometallic complex comprising at least one substituted bipyridine ligand, wherein the substituted bipyridine ligand comprises at least one sulfonate group. In embodiments, the ECL label comprises an organometallic complex comprising at least two substituted bipyridine ligands, wherein each substituted bipyridine ligand comprises at least one sulfonate group. In embodiments, the substituted bipyridine ligand is a compound of Formula I. In embodiments, the ECL label comprises three ligands, wherein a first ligand is a compound of Formula I, and wherein a second ligand comprises a bipyridine having at least one substituent that is covalently linked to the second labeled probe. In embodiments, the ECL label comprises an organometallic complex that comprises three ligands, wherein two of the ligands are each a compound of Formula I, and wherein the third ligand comprises a bipyridine having at least one substituent that is covalently linked to the second labeled probe. In embodiments, the organometallic complex comprises ruthenium, osmium, or rhenium.

In embodiments, the second detectable label comprises a compound of Formula II. In embodiments, the second detectable label comprises a compound of Formula III. In embodiments, the second detectable label comprises a compound of Formula IV. In embodiments, the second detectable label comprises a compound of Formula V. In embodiments, the second detectable label comprises a compound of Formula VI.

In embodiments, the first detectable label of the detection reagent and the second detectable label of the second labeled probe are the same. In embodiments, the first and second detectable labels each comprises an ECL label as described herein. In embodiments, the first and second detectable labels each comprises a compound of Formula II. In embodiments, the first and second detectable labels each comprises a compound of Formula III. In embodiments, the first and second detectable labels each comprises a compound of Formula IV. In embodiments, the first and second detectable labels each comprises a compound of Formula V. In embodiments, the first and second detectable labels each comprises a compound of Formula VI.

In embodiments, the first and second detectable labels are different. In embodiments, the first detectable label is not detectable once it is bound by the signal amplification reagent. In embodiments, the signal amplification reagent specifically binds to the first detectable label, and not the second detectable label. In embodiments, the first detectable label comprises a compound of Formula II, and the second detectable label comprises a compound of any one of Formulas III, IV, V, or VI. In embodiments, the first detectable label comprises a compound of Formula III, and the second detectable label comprises a compound of any one of Formulas II, IV, V, or VI. In embodiments, the first detectable label comprises a compound of Formula IV, and the second detectable label comprises a compound of any one of Formulas II, III, V, or VI. In embodiments, the first detectable label comprises a compound of Formula V, and the second detectable label comprises a compound of any one of Formulas II, III, IV, or VI. In embodiments, the first detectable label comprises a compound of Formula VI, and the second detectable label comprises a compound of any one of Formulas II, III, IV, or V. In embodiments, the first detectable label is detectably distinct from the second detectable label as described herein.

In embodiments, the method comprises measuring the amount of the first extended sequence and the second extended sequence by measuring the amount of the first and second detectable labels on the surface. In embodiments, the first and second detectable labels are detectably distinct, as described herein. In embodiments, the method comprises separately measuring the amounts of the first and second detectable labels. In embodiments, the first and second detectable labels are measured by light scattering, optical absorbance, fluorescence, chemiluminescence, electrochemiluminescence, bioluminescence, phosphorescence, radioactivity, magnetic field, or combination thereof. In embodiments, the first and second detectable labels each comprises an ECL label, and measuring the amount of the first and second detectable labels comprises measuring an ECL signal. In embodiments, the amount of measured ECL signal is used to detect the presence of the analyte in the sample. In embodiments, the amount of measured ECL signal is used to determine the amount of analyte in the sample.

In embodiments, the method comprises measuring the amount of the second extended sequence by measuring the amount of the second detectable label on the surface. In embodiments, the second detectable label is measured by light scattering, optical absorbance, fluorescence, chemiluminescence, electrochemiluminescence, bioluminescence, phosphorescence, radioactivity, magnetic field, or combination thereof. In embodiments, the second detectable label comprises an ECL label, and measuring the amount of the second detectable label comprises measuring an ECL signal. In embodiments, the amount of measured ECL signal is used to detect the presence of the analyte in the sample. In embodiments, the amount of measured ECL signal is used to determine the amount of analyte in the sample.

Surface

In embodiments, the first complex comprises a capture reagent, and the capture reagent is immobilized to the surface. In embodiments, the first complex comprises a capture reagent, and the capture reagent is directly immobilized on the surface. In embodiments, the capture reagent is indirectly immobilized on the surface via secondary binding reagents, e.g., a targeting agent. In embodiments, the capture reagent is linked to a targeting agent complement that binds to a targeting agent immobilized on the surface. In embodiments, the targeting agent complement directly binds to the targeting agent. In embodiments, the targeting agent and targeting agent complement comprise complementary oligonucleotides, a receptor-ligand pair, an antigen-antibody pair, a hapten-antibody pair, an epitope-antibody pair, a mimotope-antibody pair, an aptamer-target molecule pair, hybridization partners, or an intercalator-target molecule pair. In embodiments, the targeting agent and targeting agent complement are cross-reactive moieties, e.g., thiol and maleimide or iodoacetamide; aldehyde and hydrazide; or azide and alkyne or cycloalkyne. In embodiments, the targeting agent is biotin, and the targeting agent complement is avidin or streptavidin.

In embodiments, the targeting agent complement binds to the targeting agent via a targeting bridge agent, which is a binding partner of both the targeting agent and the targeting agent complement. In embodiments, the targeting bridge agent comprises multiple binding sites. In embodiments, the targeting bridge agent is streptavidin or avidin, and the targeting agent and targeting agent complement are each biotin.

In embodiments, the first complex, which comprises the capture reagent, the analyte, and the detection reagent, is formed in a single step. In embodiments, the first complex, which comprises the capture reagent, the analyte, and the first and second detection reagents, is formed in a single step. In embodiments, the first complex is formed in one or more steps. In embodiments, the first complex is formed on the surface. In embodiments, the first complex is formed in solution, then immobilized to the surface. In embodiments, the first complex is formed by binding the analyte to the capture reagent immobilized on the surface, then binding the detection reagent to the analyte to form the first complex on the surface. In embodiments, the first complex is formed by binding the analyte to the capture reagent immobilized on the surface, then binding the first and second detection reagents to the analyte to form the first complex on the surface. In embodiments, the first complex is formed by binding the analyte to the capture reagent immobilized on the surface and to the detection reagent simultaneously. In embodiments, the first complex is formed by binding the analyte to the capture reagent immobilized on the surface and to one or both of the first and second detection reagents simultaneously. In embodiments, the first complex is formed by binding the analyte to the detection reagent in solution to form an analyte-detection reagent complex, then binding the analyte-detection reagent complex to the capture reagent on the surface. In embodiments, the first complex is formed by binding the analyte to the first and second detection reagents in solution to form an analyte-detection reagent complex, then binding the analyte-detection reagent complex to the capture reagent on the surface. In embodiments, the first complex is formed by binding the analyte to the capture reagent and the detection reagent in solution, then immobilizing the capture reagent to the surface as described herein. In embodiments, the first complex is formed by binding the analyte to the capture reagent and the first and second detection reagents in solution, then immobilizing the capture reagent to the surface as described herein. In embodiments where the first complex comprises first and second detection reagents, the first and second detection reagents may be bound to the analyte simultaneously or sequentially.

In embodiments comprising an anchoring reagent (e.g., an anchoring reagent for binding to an extended sequence, a first anchoring reagent for binding to a first extended sequence, and/or a second anchoring reagent for binding to a second extended sequence, as described herein), the anchoring reagent is immobilized to the surface. In embodiments, the anchoring reagent is directly immobilized on the surface. In embodiments, the anchoring reagent is indirectly immobilized on the surface via secondary binding reagents, e.g., a targeting reagent as described herein. In embodiments, the targeting agent and targeting agent complement for the anchoring reagent is selected such that the targeting agent and targeting agent complement associated with the anchoring reagent are substantially non-cross-reactive with the targeting agent and targeting agent complement associated with the capture reagent. In embodiments, the same targeting agent and targeting complement pair is associated with the capture reagent and the anchoring reagent. In embodiments, the targeting agent complement binds to the targeting agent via a targeting bridge agent as described herein. In embodiments, the anchoring reagent is immobilized to the surface simultaneously or substantially simultaneously as the capture reagent is immobilized to the surface. In embodiments, the anchoring reagent is immobilized to the surface before the capture reagent is immobilized to the surface. In embodiments, the anchoring reagent is immobilized to the surface after the capture reagent is immobilized to the surface. In embodiments, the anchoring reagent is immobilized to the surface before, during, or after formation of the first complex described herein. In embodiments, the anchoring reagent is immobilized to the surface prior to forming the extended sequence described herein. In embodiments, the anchoring reagent is immobilized to the surface prior to measuring the measuring the amount of extended sequence.

In embodiments, the surface comprises a particle. In embodiments, the surface comprises a well of multi-well plate. In embodiments, the surface comprises a plurality of distinct binding domains, and the capture reagent and anchoring reagent are located on two distinct binding domains on the surface. In embodiments where the surface comprises a well, the well comprises a plurality of distinct binding domains, and the capture reagent and anchoring reagent are located on two distinct binding domains within the well. In embodiments, the surface comprises a plurality of distinct binding domains, and the capture reagent and anchoring reagent are located on the same binding domain on the surface. In embodiments where the surface comprises a well, the well comprises a plurality of distinct binding domains, and the capture reagent and anchoring reagent are located on the same binding domain within the well. In embodiments, the capture reagent is within about 1 nm to about 500 nm, about 5 nm to about 250 nm, about 10 nm to about 200 nm, or about 15 nm to about 150 nm of the anchoring reagent on the surface. In embodiments, the capture reagent is less than 1 μm from the anchoring reagent on the surface. In embodiments, the capture reagent is less than 500 nm from the anchoring reagent on the surface. In embodiments, the capture reagent is less than 200 nm from the anchoring reagent on the surface.

In embodiments where the detection reagent comprises a first nucleic acid probe that forms a first extended sequence and the signal amplification reagent comprises a second nucleic acid probe that forms a second extended sequence, the surface comprises a first anchoring reagent capable of binding to the first extended sequence and a second anchoring reagent capable of binding to the second extended sequence. In embodiments, the first anchoring reagent and the second anchoring reagent are located on distinct binding domains on the surface. In embodiments, the first anchoring reagent and the second anchoring reagent are in the same binding domain on the surface. In embodiments, the capture reagent is in a further distinct binding domain from each of the first and second anchoring reagents. In embodiments, the capture reagent is in the same binding domain as the first and second anchoring reagents.

In embodiments, the surface comprises an electrode. In embodiments, the electrode is a carbon ink electrode. In embodiments, measuring the amount of second detectable label comprises applying a voltage waveform (e.g., a potential) to the electrode to general an ECL signal. In embodiments, the surface comprises a particle, and the method comprises collecting the particle on an electrode and applying a voltage waveform (e.g., a potential) to the electrode to generate an ECL signal.

Multiplexed Methods

In embodiments, the method is a multiplexed method capable of detecting multiple analytes. In embodiments, the multiplexed method detects multiple analytes simultaneously. In embodiments, the multiplexed method comprises repeating one or more method steps to measure the multiple analytes. In embodiments, each of the method steps is performed for each analyte in parallel. In embodiments, each analyte binds to different capture and/or detection reagents. In embodiments, the binding of each analyte to its corresponding capture reagent is performed in parallel by contacting the surface(s) with a sample comprising multiple analytes. In embodiments, the multiple analytes are present in the sample in different amounts (e.g., concentrations). For example, one analyte is present at a concentration that is 10, 100, 1000, 10000, 100000, $10^6$, $10^7$, $10^8$, $10^9$, or $10^{10}$ fold lower or higher than another analyte. Thus, in embodiments, an advantage of the multiplexed methods disclosed herein is that they are capable of detecting concentrations of analytes that range from about 0.0001 pg/mL to about 100000 pg/mL, about 0.0005 pg/mL to about 50000 pg/mL, about 0.001 pg/mL to about 10000 pg/mL, about 0.005 pg/mL to about 5000 pg/mL, about 0.01 pg/mL to about 1000 pg/mL, about 0.05 pg/mL to about 500 pg/mL, about 0.1 pg/mL to about 100 pg/mL, about 0.5 pg/mL to about 50 pg/mL, or about 1 pg/mL to about 10 pg/mL. In embodiments, a highest abundance analyte is present in the sample at a concentration of greater than or about 10 pg/mL, and a lowest abundance analyte is present in the sample at a concentration of less than about 10 pg/mL. In embodiments, a highest abundance analyte is present in the sample at a concentration of greater than or about 1 pg/mL, and a lowest abundance analyte is present in the sample at a concentration of less than 1 pg/mL. In embodiments, a highest abundance analyte is present in the sample at a concentration of greater than or about 0.5 pg/mL, and a lowest abundance analyte is present in the sample at a concentration of less than 0.5 pg/mL. In embodiments, a highest abundance analyte is present in the sample at a concentration of greater than or about 0.3 pg/mL, and a lowest abundance analyte is present in the sample at a concentration of less than 0.3 pg/mL. In embodiments, a highest abundance analyte is present in the sample at a concentration of greater than or about 0.1 pg/mL, and a lowest abundance analyte is present in the sample at a concentration of less than 0.1 pg/mL. In embodiments, a highest abundance analyte is present in the sample at a concentration of about 1 pg/mL to about 100000 pg/mL, and a lowest abundance analyte is present in the sample at a concentration of about 0.0001 pg/mL to about 1 pg/mL. In embodiments, a highest abundance analyte is present in the sample at a concentration of about 0.1 pg/mL to about 100000 pg/mL, and a lowest abundance analyte is present in the sample at a concentration of about 0.0001 pg/mL to about 0.1 pg/mL. In embodiments, the amount of the highest abundance analyte present in the sample is about 1.5-fold, about 2-fold, about 3-fold, about 4-fold, about 5-fold, about 10-fold, about 15-fold, about 20-fold, about 30-fold, about 40-fold, about 50-fold, about 60-fold, about 70-fold, about 80-fold, about 90-fold, about 100-fold, about 250-fold, about 500-fold, about 750-fold, about 1000-fold, about 10000-fold, about 100000-fold, about $10^6$-fold, about $10^7$-fold, about $10^8$-fold, about $10^9$-fold, about $10^{10}$-fold, or greater than $10^{10}$-fold higher than the amount of the lowest abundance analyte present in the sample.

In embodiments, the invention provides a method of detecting multiple analytes of interest in a sample, wherein the analytes are present at concentrations that range from about 0.0001 pg/mL to about 100000 pg/mL, comprising: forming a plurality of first complexes as described herein, wherein each first complex comprises a unique analyte and a capture reagent and detection reagent or first and second detection reagents for the unique analyte; measuring the amounts of the first complexes (e.g., by measuring the amount of a first detectable label as described herein), thereby detecting a higher abundance analyte in the sample; contacting the plurality of first complexes with a signal amplification reagent as described herein, wherein the signal amplification reagent comprises a binding moiety that binds a detectable moiety comprising a second detectable label, or wherein the signal amplification reagent comprises an enzyme that acts upon a substrate of the enzyme, or wherein the signal amplification reagent comprises a nucleic acid probe that forms an extended sequence; and measuring the amount of the second detectable label, the enzyme activity, or the amount of the extended sequence (e.g., by measuring a second detectable label that binds to the extended sequence) as described herein, thereby detecting a lower abundance analyte in the sample; wherein the amount of the higher abundance analyte present in the sample is about 1.5-fold, about 2-fold, about 5-fold, about 10-fold, about 25-fold, about 50-fold, about 75-fold, about 100-fold, about 500-fold, about 1000-fold, about $10^6$-fold, about $10^7$-fold, about $10^8$-fold, about $10^9$-fold, or about $10^{10}$-fold higher than the amount of the lower abundance analyte, and/or wherein the higher abundance analyte is present in the sample at a concentration of about 1 pg/mL to about 100000 pg/mL, and a lowest abundance analyte is present in the sample at a concentration of about 0.0001 pg/mL to about 1 pg/mL. In embodiments, the amounts of the first and second detectable labels being measured are substantially the same. In embodiments, the amounts of the first and second detectable labels being measured are within about 30%, about 25%, about 20%, about 15%, about 10%, about 5%, or about 1%. In embodiments, the signal amplification reagent amplifies an assay signal from the lower abundance analyte (e.g., corresponding to the amount of the second detectable label), such that the higher abundance analyte and the lower abundance analyte provide assay signals within the detection limit of an assay device. The signal amplification reagent therefore enables detection of multiple analytes at a wide range of concentrations (e.g., from about 0.0001 pg/mL to about 100000 pg/mL) using the same assay device and in a same dilution of the sample, i.e., without requiring the sample be diluted or concentrated for the measurement of an individual analyte.

In embodiments, the surface comprises a plurality of binding domains, and each analyte forms a complex (e.g., a first complex as described herein) in a different binding domain. In embodiments, the plurality of binding domains is on a single surface. In embodiments, the surface comprises a multi-well plate, and each binding domain is in a different well. In embodiments, the surface comprises a well of a multi-well plate, and each binding domain is in a separate portion of the well. In embodiments, the plurality of binding domains is on one or more surfaces. In embodiments, the surface comprises a particle, and each binding domain is on a different particle. In embodiments, the particles are arranged in a particle array. In embodiments, the particles are coded to allow for identification of specific particles and distinguish between each binding domain.

In embodiments, the binding domains are separable from one another. In embodiments, the surface is a multi-well plate comprising detachable wells, and each binding domain is in a different well. In embodiments, the surface comprises one or more particles, and each particle is separable from the remaining particles. Methods of separating particles are known in the field and include, e.g., flow cytometry, magnetic separation, affinity separation, and the like. In embodiments, the first complexes comprising the higher abundance analytes are removed from the reaction mixture after being detected. In embodiments, the first complexes comprising the higher abundance analytes are separated and/or removed from the surface after being detected. In embodiments, the separating and/or removing comprises removing first complexes comprising the higher abundance analytes from their binding domains, e.g., by selective washing of their binding domains. In embodiments, the separating and/or removing comprises separating the binding domains containing the first complexes comprising the higher abundance analytes from the remaining binding domains, e.g., the detachable wells and/or separable particles as described herein.

In embodiments, each binding domain comprises a targeting agent capable of binding to a targeting agent complement, and each capture reagent and/or anchoring reagent (e.g., an anchoring for binding to an extended sequence, a first anchoring reagent for binding to a first extended sequence, and/or a second anchoring reagent for binding to a second extended sequence, as described herein) comprises a supplemental linking agent capable of binding to a linking agent. In embodiments, the capture reagent and anchoring reagent are immobilized in the binding domain by: (1) binding the capture and anchoring reagent, via the supplemental linking agent, to a targeting reagent complement connected to the linking agent; and (2) binding the product of (1) to the binding domain comprising the targeting agent, wherein (i) each binding domain comprises a different targeting agent, and (ii) each targeting reagent complement selectively binds to one of the targeting reagents, thereby immobilizing each capture reagent and anchoring reagent to its associated binding domain.

In embodiments, an optional bridging agent, which is a binding partner of both the linking agent and the supplemental linking agent, bridges the linking agent and supplemental linking agent, such that the capture and/or anchoring reagents, each bound to its respective targeting agent complement, are contacted with the binding domains and bind to their respective targeting agents via the bridging agent, the targeting agent complement on each of the capture and/or anchoring reagents, and the targeting agent on each of the binding domains.

In embodiments, the targeting agent and targeting agent complement are two members of a binding partner pair selected from avidin-biotin, streptavidin-biotin, antibody-hapten, antibody-antigen, antibody-epitope tag, nucleic acid-complementary nucleic acid, aptamer-aptamer target, and receptor-ligand. In embodiments, the targeting agent and targeting agent complement are cross-reactive moieties, e.g., thiol and maleimide or iodoacetamide; aldehyde and hydrazide; azide and alkyne or cycloalkyne; alkene and maleimide; thiol and disulfide; aldehyde or ketone and amine; or trans-cyclooctene and tetrazine. In embodiments, the targeting agent is biotin, and the targeting agent complement is avidin or streptavidin.

In embodiments, the linking agent and supplemental linking agent are two members of a binding partner pair selected from avidin-biotin, streptavidin-biotin, antibody-hapten, antibody-antigen, antibody-epitope tag, nucleic acid-complementary nucleic acid, aptamer-aptamer target, and receptor-ligand. In embodiments, the linking agent and supplemental linking agent are cross-reactive moieties, e.g., thiol and maleimide or iodoacetamide; aldehyde and hydrazide; azide and alkyne or cycloalkyne; alkene and maleimide; thiol and disulfide; aldehyde or ketone and amine; or trans-cyclooctene and tetrazine. In embodiments, the linking agent is avidin or streptavidin, and the supplemental linking agent is biotin. In embodiments, the targeting agent and targeting agent complement are complementary oligonucleotides. In embodiments, the targeting agent complement is streptavidin, the targeting agent is biotin, and the linking agent and the supplemental linking agent are complementary oligonucleotides.

In embodiments comprising a bridging agent, the bridging agent is streptavidin or avidin, and the linking agents and the supplemental linking agents are each biotin. Methods of conducting multiplexed assays are further described in, e.g., U.S. Pat. Nos. 10,189,023 and 10,201,812.

Analytes and Samples

In embodiments, the sample is a biological sample. In embodiments, the sample is an environmental sample. In embodiments, the sample is obtained from a human subject. In embodiments, the sample is obtained from an animal subject. In embodiments, the sample comprises a mammalian fluid, secretion, or excretion. In embodiments, the sample is a purified mammalian fluid, secretion, or excretion. In embodiments, the mammalian fluid, secretion, or excretion is whole blood, plasma, serum, sputum, lachrymal fluid, lymphatic fluid, synovial fluid, pleural effusion, urine, sweat, cerebrospinal fluid, ascites, milk, stool, bronchial lavage, saliva, amniotic fluid, nasal secretions, vaginal secretions, a surface biopsy, sperm, semen/seminal fluid, wound secretions and excretions, or an extraction, purification therefrom, or dilution thereof. Further exemplary samples include but are not limited to physiological samples, samples containing suspensions of cells such as mucosal swabs, tissue aspirates, tissue homogenates, cell cultures, and cell culture supernatants. In embodiments, the sample is whole blood, serum, plasma, cerebrospinal fluid, urine, saliva, or an extraction or purification therefrom, or dilution thereof. In embodiments, the sample is serum or plasma. In embodiments, the plasma is in EDTA, heparin, or citrate.

Samples may be obtained from a single source described herein, or may contain a mixture from two or more sources.

Analytes that may be measured using the methods of the invention include, but are not limited to, proteins, toxins, nucleic acids, microorganisms, viruses, cells, fungi, spores, carbohydrates, lipids, glycoproteins, lipoproteins, polysaccharides, drugs, hormones, steroids, nutrients, metabolites, and any modified derivative of the above molecules, or any complex comprising one or more of the above molecules or combinations thereof. The level of an analyte of interest in a sample may be indicative of a disease or disease condition or it may simply indicate whether a subject was exposed to that analyte.

In embodiments, the sample comprises multiple analytes of interest. In embodiments, the multiple analytes are present in the sample in different amounts (e.g., concentrations). For example, one analyte is present at a concentration that is 10, 100, 1000, 10000, 100000, $10^6$, $10^7$, $10^8$, $10^9$, or $10^{10}$ fold lower or higher than another analyte. Thus, in embodiments, an advantage of the methods disclosed herein is that they are capable of detecting concentrations of analytes that range from about 0.0001 pg/mL to about 100000 pg/mL, about 0.0005 pg/mL to about 50000 pg/mL, about 0.001 pg/mL to about 10000 pg/mL, about 0.005 pg/mL to about 5000 pg/mL, about 0.01 pg/mL to about 1000 pg/mL, about 0.05 pg/mL to about 500 pg/mL, about 0.1 pg/mL to about 100 pg/mL, about 0.5 pg/mL to about 50 pg/mL, or about 1 pg/mL to about 10 pg/mL. In embodiments, a further advantage of the methods disclosed herein is that they are capable of detecting multiple analytes at different concentrations (e.g., from about 0.0001 pg/mL to about 100000 pg/mL) in a same dilution of the sample, i.e., without requiring the sample be diluted or concentrated for the measurement of an individual analyte. In embodiments, a further advantage of the methods disclosed herein is that they are capable of using a same detection reagent (or same first and second detection reagents) that comprises a first detectable label for any particular analyte to be detected at any concentration between about 0.0001 pg/mL to about 100000 pg/mL.

In embodiments, a highest abundance analyte is present in the sample at a concentration of greater than or about 10 pg/mL, and a lowest abundance analyte is present in the sample at a concentration of less than about 10 pg/mL. In embodiments, a highest abundance analyte is present in the sample at a concentration of greater than or about 1 pg/mL, and a lowest abundance analyte is present in the sample at a concentration of less than 1 pg/mL. In embodiments, a highest abundance analyte is present in the sample at a concentration of greater than or about 0.5 pg/mL, and a lowest abundance analyte is present in the sample at a concentration of less than 0.5 pg/mL. In embodiments, a highest abundance analyte is present in the sample at a concentration of greater than or about 0.3 pg/mL, and a lowest abundance analyte is present in the sample at a concentration of less than 0.3 pg/mL. In embodiments, a highest abundance analyte is present in the sample at a concentration of greater than or about 0.1 pg/mL, and a lowest abundance analyte is present in the sample at a concentration of less than 0.1 pg/mL. In embodiments, a highest abundance analyte is present in the sample at a concentration of about 1 pg/mL to about 100000 pg/mL, and a lowest abundance analyte is present in the sample at a concentration of about 0.0001 pg/mL to about 1 pg/mL. In embodiments, a highest abundance analyte is present in the sample at a concentration of about 0.1 pg/mL to about 100000 pg/mL, and a lowest abundance analyte is present in the sample at a concentration of about 0.0001 pg/mL to about 0.1 pg/mL. In embodiments, the amount of the highest abundance analyte present in the sample is about 1.5-fold, about 2-fold, about 3-fold, about 4-fold, about 5-fold, about 10-fold, about 15-fold, about 20-fold, about 30-fold, about 40-fold, about 50-fold, about 60-fold, about 70-fold, about 80-fold, about 90-fold, about 100-fold, about 250-fold, about 500-fold, about 750-fold, about 1000-fold, about 10000-fold, about 100000-fold, about $10^6$-fold, about $10^7$-fold, about $10^8$-fold, about $10^9$-fold, about $10^{10}$-fold, or greater than $10^{10}$-fold higher than the amount of the lowest abundance analyte present in the sample.

In embodiments, the analyte is an exosome. In embodiments, the sample comprises purified exosomes. Exosomes, also known as extracellular vesicles or EVs, are small membrane vesicles released by most cell types. The release and subsequent uptake of exosomes is a method of cell-to-cell communication and has a role in the regulation of many physiological and pathological processes. Exosomes have been shown to contain a wide variety of signaling molecules including but not limited to surface-bound and cytosolic proteins, lipids, mRNA, and miRNA, and it has been suggested that the identity and concentration of these species in each exosome can be used to deduce its cellular origin and function. Thus, genomic or proteomic profiling of a patient's total exosome population could provide valuable prognostic information for various pathological conditions, including cancers, infectious disease, kidney and liver disease, and traumatic brain injury, among others.

In embodiments, the capture reagent and detection reagent, or the capture reagent and first and second detection reagents, bind to surface markers on the surface of the exosome. For example, common proteins that are expressed by most exosomes include, but are not limited to, CD9, CD63, CD81, Hsp70, PDCD6IP, and Tsg101. In embodiments, the capture reagent and detection reagent, or the capture reagent and first and second detection reagents, bind to a marker that is specifically expressed by exosomes released by a specific cell type. For example, the method can be used to detect a particular exosome subpopulation, e.g., associated with a disease or at risk of developing a disease. In embodiments, the capture reagent and detection reagent, or the capture reagent and first and second detection reagents, bind to a disease-associated exosome surface marker.

In embodiments, the analyte is an internal analyte of an exosome, e.g., a cargo protein, a lipid, or a nucleic acid. In embodiments, the exosome is permeabilized before or after binding to the capture reagent, but before adding the detection reagent or the first and second detection reagents.

Additional Embodiments

In embodiments, the methods provided herein are in a competitive assay format. In general terms, a competitive assay, e.g., a competitive immunoassay or a competitive inhibition assay, an analyte and a competitor compete for binding to a capture and/or detection reagent (or first and second detection reagents). In such assays, the analyte is typically indirectly measured by directly measuring the competitor. As used herein, "competitor" refers to a compound capable of binding to the same capture and/or detection reagent (or first and second detection reagents) as an analyte, such that the capture and/or detection reagent (or first and second detection reagents) can only bind either the analyte or the competitor, but not both. In embodiments, competitive assays are used to detect and measure analytes that are not capable of binding more than one capture and/or detection reagents (or first and second detection reagents), e.g., small molecule analytes or analytes that do not have more than one distinct binding sites. In embodiments, competitive assays are used to detect and measure antibody biomarkers. Examples of competitive immunoassays include those described in U.S. Pat. Nos. 4,235,601; 4,442,204; and 5,028,535.

The methods herein can be conducted in a single assay chamber, such as a single well of an assay plate. The methods herein can also be conducted in an assay chamber of an assay cartridge. The assay modules, e.g., assay plates or assay cartridges, methods and apparatuses for conducting assay measurements suitable for the present invention, are described, e.g., in U.S. Pat. Nos. 8,343,526; 9,731,297; 9,921,166; 10,184,884; 10,281,678; 10,272,436; US 2004/0022677; US 2004/0189311; US 2005/0052646; US 2005/0142033; US 2018/0074082; and US 2019/0391170.

Systems

In embodiments, the invention provides an assay system for performing the methods of detecting an analyte of interest in a sample as described herein. In embodiments, the sample comprises multiple analytes, wherein the analytes are present at concentrations that range from about 0.0001 pg/mL to about 100000 pg/mL. In embodiments, the sample comprises one or more analytes with a concentration that is 10, 100, 1000, 10000, 100000, $10^6$, $10^7$, $10^8$, $10^9$, or $10^{10}$ fold higher than the lowest abundance analytes. In embodiments, the assay system is capable of detecting an analyte over the entire concentration range of about 0.0001 pg/mL to about 100000 pg/mL utilizing a capture reagent, a detection reagent or first and second detection reagents, and a signal amplification reagent as described herein. In embodiments, the assay system is capable of detecting the analyte at a concentration greater than or about 1 pg/mL utilizing the capture reagent and the detection reagent or the first and second detection reagents, and the assay system is further capable of detecting the analyte at a concentration of less than 1 pg/mL utilizing the capture reagent, the detection reagent or the first and second detection reagents, and the signal amplification reagent. In embodiments, the assay system employs the same detection reagent comprising a first detectable label, or the same first and second detection reagents each comprising a first detectable label, to detect the analyte at any concentration between about 0.0001 pg/ml and about 100000 pg/mL. In embodiments, the first detectable label is an ECL label.

In embodiments, the assay system comprises at least one memory unit, at least one processing unit programmed according to instructions on the at least one memory unit; and at least one assay system component configured to be controlled by the at least one processing unit. In embodiments, the at least one processing unit is configured to control the at least one assay system component to perform a measurement of an analyte in a sample. In embodiments, the at least one assay system component is a reader instrument. In embodiments, the assay system comprises more than one reader instruments. In embodiments, the measurement comprises measuring a detectable label. In embodiments, the detectable label is present on a detection reagent, first and second detection reagents, a labeled probe, or a detectable moiety as described herein. In embodiments, the at least one processing unit is configured to control the at least one assay system component to perform one or both of: a first measurement of a higher abundance analyte as described herein; and a second measurement of a lower abundance analyte as described herein. In embodiments, the amount of the higher abundance analyte present in the sample is about 1.5-fold, about 2-fold, about 5-fold, about 10-fold, about 25-fold, about 50-fold, about 75-fold, about 100-fold, about 500-fold, about 1000-fold, about 10000-fold, about 100000-fold, about $10^6$-fold, about $10^7$-fold, about $10^8$-fold, about $10^9$-fold, about $10^{10}$-fold, or greater than $10^{10}$-fold higher than the amount of the lower abundance analyte present in the sample. In embodiments, the higher abundance analyte is present in the sample at a concentration of about 1 pg/mL to about 100000 pg/mL and the lower abundance analyte is present in the sample at a concentration of about 0.0001 pg/mL to about 1 pg/mL. In embodiments, the higher abundance analyte and lower abundance analyte are capable of being detected in a same dilution of a sample. In embodiments, the higher abundance analyte is detected using a detection reagent comprising an ECL label. In embodiments, the higher abundance analyte is detected using first and second detection reagents each comprising an ECL label. In embodiments, the lower abundance analyte is detected using (i) a detection reagent comprising an ECL label and (ii) a signal amplification reagent that specifically binds to the ECL label. In embodiments, the lower abundance analyte is detected using (i) first and second detection reagents each comprising an ECL label and (ii) a signal amplification reagent that specifically binds to the ECL label.

In embodiments, the invention provides one or more non-transitory computer-readable media. In embodiments, the one or more non-transitory computer-readable media have instructions stored thereon that, when executed by at least one processing unit, cause the at least one processing unit to: perform, via control of an assay system, a measurement of an analyte in a sample. In embodiments, the measurement comprises measuring a detectable label. In embodiments, the detectable label is present on a detection reagent, first and second detection reagents, a labeled probe, or a detectable moiety as described herein. In embodiments, at least one processing unit performs one or both of: a first measurement of a higher abundance analyte as described herein; and a second measurement of a lower abundance analyte as described herein. In embodiments, the amount of the higher abundance analyte present in the sample is about 1.5-fold, about 2-fold, about 5-fold, about 10-fold, about 25-fold, about 50-fold, about 75-fold, about 100-fold, about 500-fold, about 1000-fold, about 10000-fold, about 100000-fold, about $10^6$-fold, about $10^7$-fold, about $10^8$-fold, about $10^9$-fold, about $10^{10}$-fold, or greater than $10^{10}$-fold higher than the amount of the lower abundance analyte present in the sample. In embodiments, the amount of the higher abundance analyte is present in the sample at a concentration of about 1 pg/mL to about 100000 pg/mL and the lower abundance analyte is present in the sample at a concentration of about 0.0001 pg/mL to about 1 pg/mL. In embodiments, the higher abundance analyte is detected using a detection reagent comprising an ECL label. In embodiments, the higher abundance analyte is detected using first and second detection reagents each comprising an ECL label. In embodiments, the lower abundance analyte is detected using (i) a detection reagent comprising an ECL label and (ii) a signal amplification reagent that specifically binds to the ECL label. In embodiments, the lower abundance analyte is detected using (i) first and second detection reagents each comprising an ECL label and (ii) a signal amplification reagent that specifically binds to the ECL label.

In embodiments, the first measurement is a measurement of a first detectable label as described herein. In embodiments, the first detectable label is present on a detection reagent. In embodiments, the first detectable label is present on each of a first detection reagent and a second detection reagent. In embodiments, the first detectable label is comprised by a labeled probe that binds to an extended sequence formed by extending a nucleic acid probe of a detection reagent. In embodiments, the second measurement is a measurement of a detectable moiety as described herein. In embodiments, the second measurement is a measurement of an enzyme activity as described herein. In embodiments, the second measurement is a measurement of a second detectable label as described herein. In embodiments, the second detectable label is present on a detectable moiety that binds to a signal amplification reagent. In embodiments, the second detectable label is comprised by a labeled probe that binds to an extended sequence formed by extending a nucleic acid probe of a signal amplification reagent. Detectable moieties, enzyme activity, labeled probes, and first and second detectable labels are described herein.

In embodiments, the first and/or second measurement is a measurement of a detectable signal. In embodiments, the first and/or second measurement is a measurement of light scattering, optical absorbance, fluorescence, chemiluminescence, electrochemiluminescence (ECL), bioluminescence, phosphorescence, radioactivity, magnetic field, or combination thereof. In embodiments, each of the first and second detectable labels is an ECL label. In embodiments, each of the first and the second measurements is an ECL measurement. In embodiments, the first measurement is an ECL measurement, and the second measurement is a measurement of an enzyme activity as described herein. In embodiments, the first measurement is an ECL measurement, and the second measurement is a measurement of a chromogenic signal, fluorescence, or chemiluminescence.

In embodiments, the measured absolute value of the first measurement is within about 30%, about 25%, about 20%, about 15%, about 10%, about 5%, or about 1% of the measured absolute value of the second measurement, or is substantially the same as the measured absolute value of the second measurement. In embodiments, the upper and lower detection limits of the system are not adjusted between the first measurement and the second measurement. In embodiments, the assay system is configured to adjust upper and lower detection limits of the system between the first measurement and the second measurement.

In embodiments, the sample comprising the multiple analytes is contacted with a surface comprising one or more binding domains, wherein each binding domain comprises a capture reagent for a unique analyte. In embodiments, the surface comprises (i) one or more binding domains comprising a higher abundance analyte and (ii) one or more binding domains comprising a lower abundance analyte. In embodiments, the amount of the higher abundance analyte present in the sample is about 1.5-fold, about 2-fold, about 5-fold, about 10-fold, about 25-fold, about 50-fold, about 75-fold, about 100-fold, about 500-fold, about 1000-fold, about 10000-fold, about 100000-fold, about $10^6$-fold, about $10^7$-fold, about $10^8$-fold, about $10^9$-fold, about $10^{10}$-fold, or greater than $10^{10}$-fold higher than the amount of the lower abundance analyte present in the sample. In embodiments, the amount of the higher abundance analyte is present in the sample at a concentration of about 1 pg/mL to about 100000 pg/mL and the lower abundance analyte is present in the sample at a concentration of about 0.0001 pg/mL to about 1 pg/mL. In embodiments, the assay system is configured to selectively perform the first measurement for the binding domains containing the higher abundance analyte, and selectively perform the second measurement for the binding domains containing the lower abundance analyte. In embodiments, the assay system is configured to selectively perform a second measurement for the binding domains that had a value lower than a predefined threshold from the first measurement. In embodiments, the first measurement and the second measurement are performed sequentially. In embodiments, the assay system is configured to perform: first, the first measurement of the binding domain(s) containing the higher abundance analyte; second, the second measurement of the binding domain(s) containing the lower abundance analyte. In embodiments, the assay system is configured to perform the first measurement and the second measurement simultaneously or substantially simultaneously. In embodiments, the assay system is configured to perform a first measurement and allow a user to determine whether a second measurement is to be performed. In embodiments, the assay system is configured to perform a first measurement and automatically determine whether a second measurement is to be performed, e.g., based on a value of one or more higher and/or lower abundance analytes measured in the first measurement. For example, if the first measurement is sufficient for measuring both the higher and lower abundance analytes in the sample, then a second measurement may not be performed.

The methods herein can be performed manually, using automated technology, or both. Automated technology may be partially automated, e.g., one or more modular instruments, or a fully integrated, automated instrument. Exemplary automated systems and apparatuses are described in WO 2018/017156, WO 2017/015636, and WO 2016/164477.

In embodiments, automated systems, e.g., modular and fully integrated systems, for performing the methods herein comprises one or more of the following automated subsystems: a computer subsystem comprising hardware (e.g., personal computer, laptop, hardware processor, disc, keyboard, display, printer), software (e.g., processes such as drivers, driver controllers, and data analyzers), and/or a database; a liquid handling subsystem for sample and/or reagent handling, e.g., comprising a robotic pipetting hand, syringe, stirring apparatus, ultrasonic mixing apparatus, and/or magnetic mixing apparatus; a sample, reagent, and/or consumable storing and handling subsystem, e.g., comprising a robotic manipulator, tube or lid or foil piercing apparatus, lid removing apparatus, conveying apparatus such as linear or circular conveyor, tube rack, plate carrier, trough carrier, pipet tip carrier, plate shaker, and/or centrifuge; an assay reaction subsystem, e.g., that is fluid-based and/or consumable-based (such as tube and multi-well plate); a container and consumable washing subsystem, e.g., comprising a plate washing apparatus; a magnetic separator or magnetic particle concentrator subsystem, e.g., that is flow cell type, tube type, and/or plate type; a cell and particle detection, classification, and/or separation subsystem, e.g., comprising a flow cytometer and/or a Coulter counter; a detection subsystem, e.g., comprising a colorimetric detector, a nephelometric detector, a fluorescence detector, and/or an ECL detector; a temperature control subsystem, e.g., comprising an air handling system, air cooling system, air warming system, fan, blower, and/or water bath; a waste subsystem, e.g., comprising liquid and/or solid waste containers; a global unique identifier (GUI) detecting subsystem, e.g., comprising 1D and/or 2D barcode scanners such as flat bed and wand type scanners. In embodiments, the automated system further comprises a modular or fully integrated analytical subsystem, e.g., a chromatography system such as high-performance liquid chromatography (HPLC) or fast-protein liquid chromatography (FPLC), or a mass spectrometer.

In embodiments, systems or modules that perform sample identification and preparation are combined with, adjoined to, adjacent to, and/or robotically linked or coupled to the systems or modules that perform and/or detect the assays herein. Multiple modular systems of the same type can be combined to increase throughput. In embodiments, a modular system is combined with a module that performs other types of analysis, such as chemical, biochemical, and/or nucleic acid analysis.

In embodiments, the automated system allows batch, continuous, random-access, and/or point-of-care workflows, and single, medium, and high sample throughput.

In embodiments, the automated system comprises one or more of the following devices: a plate sealer (e.g., ZYMARK®), a plate washer (e.g., BIOTEK®, TECAN®), a reagent dispenser, automated pipetting station, and/or liquid handling station (e.g., TECAN®, ZYMARK®, LABSYSTEMS™, BECKMAN COULTER®, HAMILTON®), an incubator (e.g., ZYMARK®), a plate shaker (e.g., Q INSTRUMENTS®, INHECO®, THERMOFISHER SCIENTIFIC®), a plate reader (e.g., MESO® SECTOR S 600, MESO® QUICKPLEX SQ 120, and plate readers described in U.S. Pat. No. 6,977,722), a compound library module, a sample storage module, and/or a compound and/or sample retrieval module. In embodiments, one or more of these devices is coupled to the automated system via a robotic assembly such that the entire assay process can be performed automatically. In embodiments, a container (e.g., a plate) is manually moved between the apparatus and various devices described herein (e.g., a stack of plates).

In embodiments, the automated system is configured to perform one or more of the following functions: moving consumables such as plates into, within, and out of the detection subsystem; moving consumables between other subsystems; storing the consumables; sample and reagent handling (e.g., adapted to mix reagents and/or introduce reagents into consumables); consumable shaking (e.g., for mixing reagents and/or for increasing reaction rates); consumable washing (e.g., washing plates and/or performing assay wash steps (e.g., well aspirating)); measuring a detectable signal, e.g., ECL signal, in a flow cell or a consumable such as a tube or a plate. The automated system may be configured to handle individual tubes placed in racks and/or multi-well plates such as 96 or 384 well plates.

Methods for integrating components and modules in automated systems as described herein are discussed, e.g., by Sargeant et al., "Platform Perfection," Medical Product Outsourcing, May 17, 2010.

In embodiments, the automated system is fully automated, modular, computerized, performs in vitro quantitative and qualitative tests on a wide range of analytes, and/or performs photometric assays, ion-selective electrode measurements, and/or electrochemiluminescence (ECL) assays. In embodiments, the system comprises one or more of the following hardware units: a control unit, a core unit and at least one analytical module.

In embodiments, the control unit utilizes a graphical user interface to control all instrument functions and comprises a readout device, such as a monitor; an input device, such as keyboard and mouse; and a personal computer, e.g., using a Windows operating system. In embodiments, the core unit comprises one or more components that manage conveyance of samples to each assigned analytical module. The actual composition of the core unit depends on the configuration of the analytical modules, which can be configured by one of skill in the art using methods known in the art. In embodiments, the core unit comprises at least the sampling unit and one rack rotor as main components. In embodiments, the control unit further comprises an extension unit, e.g., a conveyor line and/or a second rack rotor. In embodiments, the core unit further comprises a sample rack loader/unloader, a port, a barcode reader (for racks and samples), a water supply, and a system interface port. In embodiments, the automated system conducts ECL assays and comprises a reagent area, a measurement area, a consumables area, and a pre-clean area.

Assay devices consistent with embodiments herein may be employed for, e.g., conducting assays in a multi-well plate format that have one or more of the following desirable attributes: (i) high sensitivity, (ii) large dynamic range, (iii) small size and weight, (iv) array-based multiplexing capability, (v) automated operation; and (vi) ability to handle multiple plates. The apparatus and methods may be used with a variety of assay detection techniques including, but not limited to, techniques measuring one or more detectable signals. Some aspects are suitable for electrochemiluminescence measurements and, in particular, embodiments that are suitable for use with multi-well plates with integrated electrodes (and assay methods using these plates) such as those described in U.S. Pat. Nos. 7,842,246; 7,807,448; and 10,281,678.

In embodiments, an assay device is provided for conducting luminescence assays in multi-well plates. For instance, an embodiment of the assay device includes a light detection subsystem and a plate handling subsystem, wherein the plate handling subsystem includes a light-tight enclosure that provides a light-free environment in which luminescence measurements can be carried out. The light-tight enclosure includes a housing and a removable drawer that is placed within the housing. The housing also includes a housing top having one or more plate introduction apertures through which plates can be lowered onto or removed from a plate translation stage (manually or mechanically) within the drawer. A sliding light-tight door in the housing is used to seal the plate introduction apertures from environmental light prior to carrying out luminescence measurements. The housing further includes a detection aperture that is coupled to a light detector mounted on the housing top and one or more plate stackers mounted on the housing top above the plate introduction apertures, wherein the plate stackers are configured to receive or deliver plates to plate elevators within the removable drawer. The removable drawer includes a plate translation stage for translating a plate horizontally in the drawer to zones within the apparatus where specific assay processing and/or detection steps are carried out. The removable drawer also includes one or more plate elevators with a plate lifting platform that can be raised and lowered within the drawer, wherein the plate elevators are positioned below the one or more plate introduction apertures. The plate translation stage is configured to position plates below the detection aperture and to position plates above the plate elevators on the plate lifting platforms.

The assay device may also include a light detector which is mounted to the detection aperture on the housing top (e.g., via a light-tight connector or baffle). In certain embodiments, the light detector is an imaging light detector such as a CCD camera and may also include a lens. The light detector may be a conventional light detector such as a photodiode, avalanche photodiode, photomultiplier tube, or the like. Suitable light detectors also include arrays of such light detectors. Light detectors that may be used also include imaging systems such as CCD and CMOS cameras. The light detectors may also include lens, light guides, etc. for directing, focusing, and/or imaging light on the detectors. In certain specific embodiments, an imaging system is used to image luminescence from arrays of binding domains in one or more wells of an assay plate, and the assay apparatus reports luminescence values for luminescence emitted from individual elements of the arrays. The light detector is mounted on the housing top with a light-tight seal. Additional components of the apparatus include plate contacts for making electrical contact to the plates and providing electrical energy to electrodes in wells positioned under the light detector (e.g., for inducing ECL).

In embodiments, the assay device includes features, such as an identifier controller, for the automated identification of sample plates. In an embodiment, an identifier controller is a bar code reader mounted via a light-tight seal over an aperture in the housing top, where the bar code reader is configured to read bar codes on plates placed on the plate translation stage within the housing. In a preferred embodiment, the bar code on a plate is read when the plate has been lowered into the drawer. In an alternative or additional embodiment, the plates comprise an identifier such as an EEPROM or an RFID, and the housing top and/or drawer includes an identifier controller suitable for communicating with each of these identifiers. In further embodiments, an identifier controller can be provided separately from the apparatus. In this embodiment, information stored to an identifier attached to a plate or associated with a plate or a set of plates is transferred to the apparatus via a computer and/or network attached thereto and/or manually input via a user interface of the computer and/or network. In this regard, reference is made to U.S. Patent Publication No. 2011/0022331 and U.S. Pat. No. 8,770,471.

In some cases, the plate handling subsystem further includes one or more plate stackers mounted on the housing top above the plate introduction apertures, wherein the plate stackers are configured to receive or deliver plates to the plate elevators. The plate handling subsystem optionally includes a heating and/or cooling mechanism (e.g., a resistance heater, a fan, heat sinks, or a thermoelectric heater/cooler) to maintain temperature of the subsystem under desired conditions. It may also include a humidity control mechanism (e.g., a humidifier and/or dehumidifier, or a desiccant chamber to maintain the humidity of the subsystem under desired conditions.

Assay devices, as described herein, are configured to perform both calibration assays and sample assays. As described herein, calibration assays include assays performed on calibration samples that have defined quantities of an analyte. As described herein, sample assays on one or more test samples each having an unknown quantity of an analyte. Performing a sample assay on a test sample generates a sample assay signal value. The sample assay signal value is indicative of the unknown quantity of the analyte associated therewith.

In embodiments, a computer system is provided herein. The computing system may include one or more processors (also interchangeably referred to herein as processing units), one or more storage device(s), and/or other components. In other embodiments, the functionality of the processor may be performed by hardware (e.g., through the use of an application specific integrated circuit ("ASIC"), a programmable gate array ("PGA"), a field programmable gate array ("FPGA"), etc.), or any combination of hardware and software. The storage device includes any type of non-transitory computer readable storage medium (or media) and/or non-transitory computer readable storage device. Such computer readable storage media or devices may store computer readable program instructions for causing a processor to carry out one or more methodologies described here. Examples of the computer readable storage medium or device may include, but is not limited to an electronic storage device, a magnetic storage device, an optical storage device, an electromagnetic storage device, a semiconductor storage device, or any suitable combination thereof, for example, such as a computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, but not limited to only those examples.

The processor is programmed by one or more computer program instructions stored on the storage device and executable by the processor. For example, the processor is programmed by a protocol manager, a network manager, a data manager, a calibration fit manager, an analysis manager, and a user interface manager. It will be understood that the functionality of the various managers as discussed herein is representative and not limiting. Additionally, the storage device may act as a data storage device to provide data storage for the assay system environment. As used herein, for convenience, the various "managers" will be described as performing operations, when, in fact, the managers program the processor (and therefore the computing system) to perform the operation.

The protocol manager is a software protocol (e.g., software module or library) that may operate on the computing system. The protocol manager is configured to provide one or more control signals to one or more assay devices. The control signals provided by the protocol manager are configured to provide instructions necessary to operate the one or more assay devices. The control signals may specify one or more assay protocols to be carried out by the one or more assay devices. Control signals provided by the protocol manager may be used to initiate and/or control any process that an assay device described herein is capable of.

In embodiments, the protocol manager may further operate to receive data collected during operation of the one or more assay devices. Such data may include, for example, calibration assay data and sample assay data. Received data may then be processed or stored via the data manager.

The protocol manager is configured to operate to control one or more assay devices to perform calibration assays. Assay devices may be controlled by the protocol manager to obtain calibration assay measurements on a plurality of calibration samples (e.g., calibration samples stored as calibrators in a multi-well plate) having defined quantities of an analyte. The plurality of calibration samples may include different quantities of the analyte. The protocol manager operates to determine calibration assay signal values corresponding to the plurality of calibration samples. The protocol manager is configured to perform the calibration assays to determine one or more calibration data sets. The calibration data sets include information relating the plurality of quantity values to a corresponding plurality of calibration assay signal values.

The protocol manager is further configured to operate to control one or more assay devices to perform sample assays. Assay devices may be controlled by the protocol manager to obtain sample assay measurements on a plurality of test samples (e.g., test samples disposed in a multi-well plate) having unknown quantities of an analyte. The protocol manager operates to determine sample assay signal values corresponding to the plurality of test samples. The protocol manager is configured to perform the sample assays to determine one or more sample assay data sets. The sample assay data sets may include information relating the sample assay signal values to sample identification data. Sample identification data may include any suitable data for identifying a test sample, such as plate location.

The network manager is a software protocol (e.g., software module or library) that may operate on the computing system. The network manager is configured to establish network communications between networks, assay devices, data storage devices, and/or any other devices in the assay system environment. The established communications pathway may utilize any appropriate network transfer protocol and provide for one way or two way data transfer. The network manager may establish as many network communications as required to communicate with various elements of the assay system environment.

The network manager facilitates the sending and receiving of sample assay data, calibration assay data (also referred to as calibration assay information), sample assay and calibration assay protocols, calibration models, and any other information and/or consistent with the operation of the assay system environment.

The data manager is a software protocol or software module that may operate on the computing system. The data manager is configured to access assay data, such as sample assay data and calibration assay data of one or more assay devices of the assay system environment. Assay data may include, for example, sample assay data sets and calibration data sets, which may be obtained in near real time, may be archived data, and/or may be data extracts, as well as process information and process parameter information and any other information or data generated by or stored on an assay device. The data manager is further configured to access one or more data storage devices, local assay computer systems, and/or networked computer system, and to store and/or receive assay data stored in any or all of these. In further embodiments, the data manager is configured to access various removable physical storage media that may store assay data.

The data manager may provide data to a user via the user interface manager. In embodiments, the data manager is further configured to provide access tools to the user to manage and manipulate assay data (also referred to as assay system data). For example, the data manager 616 may be configured to generate reports, collate assay system data, cross-reference assay system data, populate databases with assay system data, etc. In embodiments, the data manager may provide data retention capabilities. The data manager is further configured to receive and store any and all data collected and/or used within the assay system environment.

Antibody and Composition

In embodiments, the invention provides an antibody or antigen-binding fragment thereof that binds to an electrochemiluminescent (ECL) label.

In general, an antibody (used interchangeably with the term "immunoglobulin") comprises at least the variable domain of a heavy chain; typically, an antibody comprises the variable domains of a heavy chain and a light chain. Both the heavy and light chains are divided into regions of structural and functional homology. Generally, the variable domain of a heavy chain ($V_H$) or light chain ($V_L$) determines antigen recognition and specificity, and the constant domain of a heavy chain ($C_{H1}$, $C_{H2}$, or $C_{H3}$) or light chain ($C_L$) confers biological properties such as secretion, receptor binding, complement binding, and the like. Generally, the N-terminal portion of an antibody chain is a variable portion, and the C-terminal portion is a constant region; the $C_{H3}$ and $C_L$ domains typically comprise the C-terminus of the heavy chain and light chain, respectively.

In general, antibodies are encoded by immunoglobulin genes or fragments of immunoglobulin genes. The recognized immunoglobulin genes include the kappa, lambda, alpha, gamma, delta, epsilon, and mu constant region genes, as well as immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

In general, the variable region allows the antibody to selectively recognize and specifically bind epitopes on antigens. Thus, the $V_L$ domain and $V_H$ domain, or a subset of the complementarity determining regions (CDR) within these variable domains, of an antibody combine to form the variable region that forms an antigen binding domain. The antigen binding domain is typically defined by three CDRs on each of the $V_L$ and $V_H$ domains. The six "complementarity determining regions" or "CDRs" typically present in each antigen binding domain are short, non-contiguous sequences of amino acids that are specifically positioned to form the antigen binding domain. The antigen binding domain formed by the positioned CDRs defines a surface complementary to the epitope on the antigen. This complementary surface promotes the non-covalent binding of the antibody to its cognate epitope.

In embodiments, the invention provides an antibody or antigen-binding fragment thereof comprising an antigen binding domain specific to an electrochemiluminescent (ECL) label.

In embodiments, the antibody or antigen-binding fragment thereof comprises a constant region comprising an IgA, IgD, IgE, IgG, or IgM domain. In embodiments, the antibody or antigen-binding fragment thereof comprises an IgG domain. In embodiments, the antibody or antigen-binding fragment thereof is an IgG1, IgG2, IgG3, or IgG4 isotype antibody or antigen-binding fragment thereof. In embodiments, the antibody or antigen-binding fragment thereof is IgG2a, IgG2b, or IgG2c subclass antibody or antigen-binding fragment thereof.

In embodiments, the antibody or antigen-binding fragment thereof is derived from a mouse, rat, goat, rabbit, chicken, guinea pig, hamster, horse, or sheep. In embodiments, the antibody or antigen-binding fragment thereof is derived from a mouse.

ECL labels are described herein. In embodiments, the ECL label comprises an electrochemiluminescent organometallic complex. In embodiments, the electrochemiluminescent organometallic complex comprises ruthenium, osmium, iridium, rhenium, and/or a lanthanide metal. In embodiments, the ECL label comprises ruthenium. In embodiments, the electrochemiluminescent organometallic complex comprises a substituted or unsubstituted bipyridine or a substituted or unsubstituted phenanthroline. In embodiments, the ECL label comprises a substituted bipyridine. In embodiments, the ECL label comprises an organometallic complex comprising at least one substituted bipyridine ligand wherein the substituted bipyridine ligand comprises at least one sulfonate group. In embodiments, the ECL label comprises an organometallic complex comprising at least two substituted bipyridine ligands wherein each substituted bipyridine ligand comprises at least one sulfonate group. In embodiments, the substituted bipyridine ligand is a compound of Formula I. In embodiments, the ECL label comprises three ligands, wherein a first ligand is a compound of Formula I, and wherein a second ligand comprises a bipyridine having at least one substituent that is capable of forming a covalent linkage. In embodiments, the ECL label comprises an organometallic complex comprises three ligands, wherein two of the ligands are each a compound of Formula I, and wherein the third ligand comprises a bipyridine having at least one substituent that is capable of forming a covalent linkage. In embodiments, the third ligand comprises a bipyridine having at least one substituent that comprises a conjugation linker. Conjugation linkers are further described herein.

In embodiments, the antibody or antigen-binding fragment thereof comprises an antigen binding domain that specifically binds to a compound of Formula II, Formula IV, or Formula VI. In embodiments, the antibody or antigen-binding fragment comprises an antigen binding domain that specifically binds to:

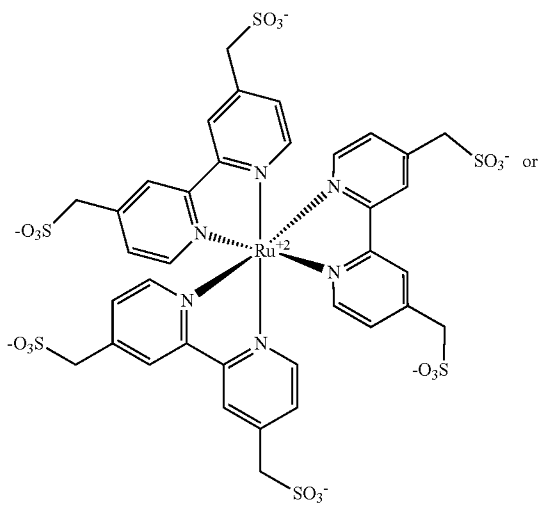

or

-continued

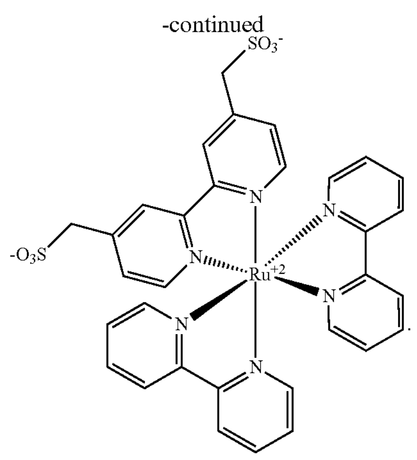

In embodiments, the invention provides an antibody or antigen-binding fragment thereof comprising an antigen binding domain specific to an ECL label and a conjugation linker. Conjugation linkers are described herein. In embodiments, the conjugation linker comprises an amide, a thioester, a thioether, a disulfide, an imine, a triazole, a dihydropyridazine, a peptide, an oligonucleotide, a hydrophilic polymer, or a combination thereof.

In embodiments, the antibody or antigen-binding fragment thereof comprises an antigen binding domain that specifically binds to the ECL label and an amide. In embodiments, the antibody or antigen-binding fragment thereof comprises an antigen binding domain that specifically binds to the ECL label and a thioester. In embodiments, the antibody or antigen-binding fragment thereof comprises an antigen binding domain that specifically binds to the ECL label and a thioether. In embodiments, the antibody or antigen-binding fragment thereof comprises an antigen binding domain that specifically binds to the ECL label and a disulfide. In embodiments, the antibody or antigen-binding fragment thereof comprises an antigen binding domain that specifically binds to the ECL label and an imine. In embodiments, the antibody or antigen-binding fragment thereof comprises an antigen binding domain that specifically binds to the ECL label and a triazole. In embodiments, the signal amplification reagent specifically binds to the ECL label and a dihydropyridazine.

In embodiments, the conjugation linker comprises a spacer (e.g., a peptide, an oligonucleotide, or a hydrophilic polymer as described herein), and the antibody or antigen-binding fragment thereof comprises an antigen binding domain that specifically binds to the ECL label and at least a portion of the peptide, oligonucleotide, or hydrophilic polymer of the conjugation linker. In embodiments, the antibody or antigen-binding fragment thereof comprises an antigen binding domain that specifically binds to the ECL label and at least a portion of a peptide of the conjugation linker. In embodiments, the antibody or antigen-binding fragment thereof comprises an antigen binding domain that specifically binds to the ECL label and at least a portion of an oligonucleotide of the conjugation linker. In embodiments, the antibody or antigen-binding fragment thereof comprises an antigen binding domain that specifically binds to the ECL label and at least a portion of a hydrophilic polymer of the conjugation linker.

In embodiments, the antibody or antigen-binding fragment thereof further comprises a nucleic acid probe. Nucleic acid probes are described herein. In embodiments, the nucleic acid probe is capable of binding to a template oligonucleotide. In embodiments, the nucleic acid probe is a primer for an extension reaction, e.g., polymerase chain reaction (PCR), ligase chain reaction (LCR), strand displacement amplification (SDA), self-sustained synthetic reaction (3SR), and/or isothermal amplification (such as, e.g., helicase-dependent amplification or rolling circle amplification), as described herein.

In embodiments, the invention provides a composition comprising: (a) an antibody or antigen-binding fragment thereof provided herein, wherein the antibody or antigen-binding fragment thereof comprises a nucleic acid probe; and (b) a template oligonucleotide that is capable of binding to the nucleic acid probe. Template oligonucleotides are further described herein.

In embodiments, the antibody or antigen-binding fragment thereof further comprises a binding moiety. Binding moieties are described herein. In embodiments, the binding moiety is capable of binding to a detectable moiety described herein. In embodiments, the binding moiety comprises an oligonucleotide. In embodiments, the binding moiety comprises biotin. In embodiments, the binding moiety comprises avidin or streptavidin. In embodiments, the binding moiety comprises multiple binding sites for the detectable moiety.

In embodiments, the invention provides a composition comprising: (a) an antibody or antigen-binding fragment thereof provided herein, wherein the antibody or antigen-binding fragment thereof comprises a binding moiety; and (b) a detectable moiety comprising (i) a binding partner of the binding moiety and (ii) one or more detectable labels. Detectable moieties are described herein. In embodiments, the detectable moiety comprises a detectable label. In embodiments, the detectable moiety comprises more than one of the detectable label. In embodiments, the labeled probe comprises 1, 2, 3, 4, 5, 6, 7, 8, 9, 10, or more than 10 of the detectable label. In embodiments, the binding moiety of the antibody or antigen-binding fragment thereof binds to the detectable moiety. In embodiments where the binding moiety comprises an oligonucleotide, the detectable moiety comprises a complementary oligonucleotide. In embodiments where the binding moiety comprises biotin, the detectable moiety comprises avidin or streptavidin. In embodiments where the binding moiety comprises avidin or streptavidin, the detectable moiety comprises biotin. In embodiments, the detectable moiety comprises multiple binding sites for the binding moiety.

Detectable labels are described herein. In embodiments, the detectable label is capable of being detected by light scattering, optical absorbance, fluorescence, chemiluminescence, electrochemiluminescence, bioluminescence, phosphorescence, radioactivity, magnetic field, or combination thereof. In embodiments, the detectable label comprises an ECL label as described herein.

In embodiments, the ECL label comprises an organometallic complex comprising three ligands, wherein a first ligand is a compound of Formula I, and wherein a second ligand comprises a bipyridine having at least one substituent that is covalently linked to the detectable moiety. In embodiments, the ECL label comprises an organometallic complex comprising three ligands, wherein two of the ligands are each a compound of Formula I, and wherein the third ligand comprises a bipyridine having at least one substituent that is covalently linked to the detectable moiety.

In embodiments, the detectable label comprises a compound of Formula II. In embodiments, the detectable label comprises a compound of Formula III. In embodiments, the detectable label comprises a compound of Formula IV. In embodiments, the detectable label comprises a compound of Formula V. In embodiments, the detectable label comprises a compound of Formula VI.

In embodiments, the antibody or antigen-binding fragment thereof further comprises an enzyme. Enzymes are further described herein. In embodiments, the enzyme is HRP, AP, or (3-galactosidase.

In embodiments, the invention provides a composition comprising: an antibody or antigen-binding fragment thereof provided herein, wherein the antibody or antigen-binding fragment thereof comprises an enzyme. In embodiments, the composition further comprises a substrate of the enzyme. In embodiments, the enzyme is HRP and the substrate is TMB, ABTS, or OPD. In embodiments, the enzyme is AP and the substrate is PNPP. In embodiments, the enzyme is β-galactosidase and the substrate is ONPG. Enzymes such as HRP, AP, and β-galactosidase, and their substrates, including TMB, ABTS, OPD, PNPP, and ONPG, are further described herein.

Kits

In embodiments, the invention provides a kit for detecting an analyte of interest comprising, in one or more vials, containers, or compartments: (a) a capture reagent that specifically binds to the analyte; (b) a detection reagent that specifically binds to the analyte, wherein the detection reagent comprises a first detectable label; and (c) a signal amplification reagent that specifically binds to the first detectable label. In embodiments, the first detectable label is an ECL label. In embodiments, the kit further comprises a surface. In embodiments, the detection reagent is a first detection reagent, and the kit further comprises a second detection reagent that specifically binds to the analyte, wherein the second detection reagent comprises a first detectable label.

In embodiments, the invention provides a kit for detecting an analyte of interest comprising, in one or more vials, containers, or compartments: (a) a capture reagent that specifically binds to the analyte; (b) a detection reagent that specifically binds to the analyte, wherein the detection reagent comprises a first nucleic acid probe; (c) a first labeled probe comprising a first detectable label; and (d) a signal amplification reagent that specifically binds to the first detectable label. In embodiments, the first detectable label is an ECL label. In embodiments, the kit further comprises a surface.

In embodiments, the invention provides a kit for detecting an analyte of interest comprising, in one or more vials, containers, or compartments: (a) a capture reagent that specifically binds to the analyte; (b) a detection reagent that specifically binds to the analyte, wherein the detection reagent comprises an ECL label; and (c) a signal amplification reagent that specifically binds to the ECL label. In embodiments, the kit further comprises a surface. In embodiments, the detection reagent is a first detection reagent, and the kit further comprises a second detection reagent that specifically binds to the analyte, wherein the second detection reagent comprises an ECL label.

In embodiments, the invention provides a kit for detecting an analyte of interest comprising, in one or more vials, containers, or compartments: (a) a capture reagent that specifically binds to the analyte; (b) a detection reagent that specifically binds to the analyte, wherein the detection reagent comprises a first nucleic acid probe; (c) a first labeled probe comprising a first ECL label; and (d) a signal amplification reagent that specifically binds to the first ECL label. In embodiments, the kit further comprises a surface.

In embodiments, the invention provides a kit comprising an antibody or antigen-binding fragment that comprises an antigen binding domain specific to an ECL label and that comprises a binding moiety, as described herein. In embodiments, the invention provides a kit comprising an antibody or antigen-binding fragment that comprises an antigen binding domain specific to an ECL label and that comprises an enzyme, as described herein. In embodiments, the kit further comprises one or both of a capture reagent and a detection reagent, wherein the detection reagent comprises an ECL label. In embodiments, the kit further comprises one or more of a capture reagent, a first detection reagent, and a second detection reagent, wherein the first and second detection reagents each comprises an ECL label. In embodiments, the kit further comprises a surface.

In embodiments, the invention provides a kit comprising an antibody or antigen-binding fragment that comprises an antigen binding domain specific to an ECL label and that comprises a nucleic acid probe as described herein. In embodiments, the kit further comprises an anchoring reagent, a template oligonucleotide, a labeled probe, a polymerase, a ligase, a buffer, a blocking agent, a coreactant, a diluent, a stabilizing agent, a calibration agent, an assay consumable, or a combination thereof. In embodiments, the kit further comprises one or both of a capture reagent and a detection reagent, wherein the detection reagent comprises an ECL label. In embodiments, the kit further comprises one or more of a capture reagent, a first detection reagent, and a second detection reagent, wherein the first and second detection reagents each comprises an ECL label. In embodiments, the kit further comprises a surface.

Capture reagents, detection reagents, e.g., first and second detection reagents, first detectable labels, and signal amplification reagents are described herein. In embodiments, the capture reagent, the detection reagent or first and second detection reagents, and the signal amplification reagent each comprises an antibody or antigen-binding fragment thereof, antigen, ligand, receptor, oligonucleotide, hapten, epitope, mimotope, or an aptamer. In embodiments, the capture reagent, the detection reagent or first and second detection reagents, and the signal amplification reagent each comprises an antibody or antigen-binding fragment thereof. In embodiments, the signal amplification reagent is an IgG antibody.

In embodiments, the first detectable label is an electrochemiluminescent (ECL) label. In embodiments, the signal amplification reagent is an antibody or antigen-binding fragment thereof comprising an antigen binding domain specific to an ECL label. ECL labels are described herein.

In embodiments, the ECL label is a compound of Formula II. In embodiments, the ECL label is a compound of Formula III. In embodiments, the ECL label is a compound of Formula IV. In embodiments, the ECL label is a compound of Formula V. In embodiments, the ECL label is a compound of Formula VI.

In embodiments, the signal amplification reagent comprises a binding moiety. In embodiments, the kit further comprises a reagent for conjugating a binding moiety to the signal amplification reagent. Binding moieties are described herein. In embodiments, the binding moiety comprises an oligonucleotide. In embodiments, the binding moiety comprises biotin. In embodiments, the binding moiety comprises avidin or streptavidin. In embodiments, the kit further comprises a detectable moiety comprising: (i) a binding partner of the binding moiety and (ii) one or more of a second detectable label. Detectable moieties are described herein. In embodiments, the binding moiety comprises an oligonucleotide, and the detectable moiety comprises a complementary oligonucleotide. In embodiments, the binding moiety comprises biotin, and the detectable moiety comprises avidin or streptavidin. In embodiments where the binding moiety comprises avidin or streptavidin, the detectable moiety comprises biotin.

In embodiments, the detectable moiety comprises a second detectable label. Second detectable labels are further described herein. In embodiments, the detectable moiety comprises more than one of the second detectable label. In embodiments, the detectable moiety comprises 1, 2, 3, 4, 5, 6, 7, 8, 9, 10, or more than 10 of the second detectable label. In embodiments, the second detectable label is an ECL label. In embodiments, the first detectable label is detectably distinct from the second detectable label as described herein.

In embodiments, the signal amplification reagent comprises an enzyme. In embodiments, the kit further comprises a substrate of the enzyme. Enzymes and their substrates are further described herein. In embodiments, the enzyme is HRP and the substrate is TMB, ABTS, or OPD. In embodiments, the enzyme is AP and the substrate is PNPP. In embodiments, the enzyme is (3-galactosidase and the substrate is ONPG. In embodiments, the substrate is a chromogenic substrate, a fluorogenic substrate, or a chemiluminescent substrate as described herein.

In embodiments, the signal amplification reagent comprises a second detectable label. Second detectable labels are further described herein. In embodiments, the signal amplification reagent comprises more than one of the second detectable label. In embodiments, the signal amplification reagent comprises 1, 2, 3, 4, 5, 6, 7, 8, 9, 10, or more than 10 of the second detectable label. In embodiments, the first detectable label is detectably distinct from the second detectable label as described herein. In embodiments, the second detectable label is an ECL label as described herein.

In embodiments, the detection reagent comprises a first detectable label, and the signal amplification reagent comprises a nucleic acid probe. In embodiments, the first and second detection reagents each comprises a first detectable label, and the signal amplification reagent comprises a nucleic acid probe. In embodiments, the kit further comprises a reagent for conjugating a nucleic acid probe to the signal amplification reagent. Nucleic acid probes are described herein. In embodiments, nucleic acid probe is a primer for an extension reaction, e.g., polymerase chain reaction (PCR), ligase chain reaction (LCR), strand displacement amplification (SDA), self-sustained synthetic reaction (3SR), and/or isothermal amplification (such as, e.g., helicase-dependent amplification or rolling circle amplification), to form an extended sequence as described herein. In embodiments, the kit further comprises a template oligonucleotide, e.g., for performing the extension reaction. In embodiments, the kit further comprises an anchoring reagent, e.g., for binding to the extended sequence produced from the extension reaction. Template oligonucleotides and anchoring reagents are further described herein. In embodiments, the anchoring reagent comprises a single stranded oligonucleotide. In embodiments, the anchoring reagent comprises a double stranded oligonucleotide. In embodiments, the kit further comprises a labeled probe comprising one or more of a second detectable label, wherein the labeled probe and the extended sequence comprise complementary oligonucleotides. In embodiments, the labeled probe comprises more than one of the second detectable label. In embodiments, the labeled probe comprises 1, 2, 3, 4, 5, 6, 7, 8, 9, 10, or more than 10 of the second detectable label. In embodiments, the second detectable label is an ECL label. In embodiments, the first detectable label is detectably distinct from the second detectable label as described herein.

In embodiments, the detection reagent comprises a first nucleic acid probe, and the signal amplification reagent comprises a second nucleic acid probe. In embodiments, the kit further comprises a reagent for conjugating the first nucleic acid probe to the detection reagent. In embodiments, the kit further comprises a reagent for conjugating the second nucleic acid probe to the signal amplification reagent. First and second nucleic acid probes are described herein. In embodiments, the kit further comprises one or more template oligonucleotides, e.g., for extending the first and second nucleic acid probes. In embodiments, the kit further comprises first and second anchoring reagents that respectively bind first and second extended sequences, as described herein. In embodiments, the kit further comprises a first labeled probe that comprises one or more of a first detectable label, wherein the first labeled probe and the first extended sequence comprise complementary oligonucleotides. In embodiments, the first labeled probe comprises more than one of the first detectable label. In embodiments, the first labeled probe comprises 1, 2, 3, 4, 5, 6, 7, 8, 9, 10, or more than 10 of the first detectable label. In embodiments, the kit further comprises a second labeled probe that comprises one or more of a second detectable label, wherein the second labeled probe and the second extended sequence comprise complementary oligonucleotides. In embodiments, the second labeled probe comprises more than one of the second detectable label. In embodiments, the second labeled probe comprises 1, 2, 3, 4, 5, 6, 7, 8, 9, 10, or more than 10 of the second detectable label. First and second labeled probes are described herein. In embodiments, the first detectable label is an ECL label. In embodiments, the second detectable label is an ECL label. In embodiments, the first detectable label is detectably distinct from the second detectable label as described herein.

In embodiments, the detection reagent or the first and second detection reagents are lyophilized. In embodiments, the detection reagent or the first and second detection reagents are provided in solution. In embodiments, the signal amplification reagent is lyophilized. In embodiments, the signal amplification reagent is provided in solution. In embodiments, the capture reagent is immobilized on a surface provided in the kit. In embodiments, the capture reagent is lyophilized or provided in solution, and the kit further comprises a reagent for immobilizing the capture reagent to a surface. In embodiments comprising an anchoring reagent (e.g., an anchoring for binding to an extended sequence, a first anchoring reagent for binding to a first extended sequence, and/or a second anchoring reagent for binding to a second extended sequence, as described herein), the anchoring reagent is immobilized on a surface provided in the kit. In embodiments, the anchoring reagent is lyophilized or provided in solution, and the kit further comprises a reagent for immobilizing the anchoring reagent to a surface. In embodiments, the capture reagent is immobilized within about 1 nm to about 500 nm, about 5 nm to about 250 nm, about 10 nm to about 200 nm, or about 15 nm to about 150 nm of the anchoring reagent on the surface. In embodiments, the capture reagent is immobilized less than 1 μm from the anchoring reagent on the surface. In embodiments, the capture reagent is immobilized less than 500 nm from the anchoring reagent on the surface. In embodiments, the capture reagent is immobilized less than 200 nm from the anchoring reagent on the surface. Reagents and methods for immobilizing capture and/or anchoring reagents to surfaces, e.g., via targeting agents/targeting agent complements, linking agents/supplemental linking agents, and bridging agents are described herein.

In embodiments, the kits provided herein further comprise a surface. In embodiments, the surface is a plate. In embodiments, the surface is a multi-well plate. In embodiments, the surface is a particle. In embodiments, the kit comprises a particle array. In embodiments, the surface is a cartridge. In embodiments, the surface comprises an electrode. In embodiments, the electrode is a carbon ink electrode.

In embodiments, the capture, detection, and/or signal amplification reagents and other components of the kit are provided separately. In embodiments, the components of the kit are provided separately according to their optimal shipping or storage temperatures.

In embodiments, the kit further comprises a calibration reagent. In embodiments, the calibration reagent comprises a known quantity of the analyte. In embodiments, the kit comprises multiple calibration reagents comprising a range of concentrations of the analyte. In embodiments, the multiple calibration reagents comprise concentrations of the analyte near the upper and lower limits of quantitation for the method. In embodiments, the multiple calibration reagents span the entire dynamic range of the method. In embodiments, the calibration reagent is a positive control reagent. In embodiments, the calibration reagent is a negative control reagent. In embodiments, the positive or negative control reagent is used to provide a basis of comparison for the sample to be tested with the methods of the present invention. In embodiments, the calibration reagent is lyophilized. In embodiments, the calibration reagent is provided in solution.

In embodiments, the kit further comprises a polymerase, a ligase, a buffer, a blocking agent, a co-reactant, a diluent, a stabilizing agent, a calibration agent, an assay consumable, an electrode, or a combination thereof.

In embodiments, the kit further comprises a polymerase, e.g., for performing polymerase chain reaction (PCR), ligase chain reaction (LCR), strand displacement amplification (SDA), self-sustained synthetic reaction (3SR), and/or isothermal amplification (such as, e.g., helicase-dependent amplification or rolling circle amplification). In embodiments, the kit further comprises a ligase, e.g., for ligating the template oligonucleotide.

In embodiments, the kit further comprises a buffer, e.g., an assay buffer, a reconstitution buffer, a storage buffer, a read buffer, or a combination thereof. In embodiments, the kit further comprises a co-reactant, e.g., for performing an electrochemiluminescence measurement. Exemplary co-reactants are described, e.g., in WO 2020/142313.

In embodiments, the kit further comprises a blocking agent, e.g., to decrease non-specific binding by components other than the analyte of interest to the capture reagent and the detection reagent, or the capture reagent and the first and second detection reagents described herein. Exemplary blocking agents include, but are not limited to, mBSA, sheared poly(A), polyBSA-I, mIgG, Tween, polyBSA-II, yeast RNA, mBSA+poly(a), and/or polyBSA+poly(A). In embodiments, the kit further comprises a diluent for one or more components of the kit. In embodiments, a kit comprising the components above includes stock concentrations of the components that are 5×, 10×, 20×, 30×, 40×, 50×, 60×, 70×, 80×, 90×, 100×, 125×, 150× or higher fold concentrations of a working concentration for the methods provided herein. In embodiments, the kit further comprises a stabilizing agent, e.g., for storage of one or more components of the kit.

In embodiments, the kit further comprises an assay consumable, e.g., assay modules, vials, tubes, liquid handling and transfer devices such as pipette tips, covers and seals, racks, labels, and the like. In embodiments, the kit further comprises an electrode, e.g., for performing an electrochemiluminescence measurement. In embodiments, the electrode is applied to the surface provided herein. In embodiments, the kit further comprises an assay instrument and/or instructions for carrying out the methods described herein.

It will be understood by one of ordinary skill in the art that components of the kits described herein, which may be provided in one or more vials, containers, or compartments, are not necessarily included in the same container, e.g., same box, and/or at the same time. In embodiments, the components of the kits described herein are provided in one or more separate containers or compartments either simultaneously or sequentially. It will be further understood by one of ordinary skill in the art that a user may obtain (e.g., purchase or possess) the components of the kit (e.g., the signal amplification reagent described herein) separately, e.g., in one or more separate containers or compartments, but nonetheless the components are considered part of a "kit" when used in combination, e.g., as described in embodiments herein. In some embodiments, a kit comprises multiple containers, vials, or compartments supplied together in a single package or container.

In embodiments, the invention provides a set of kits comprising a plurality of first kits and a second kit, wherein each first kit is for detecting a unique analyte of interest, and wherein each first kit comprises: (a) a capture reagent that specifically binds to a unique analyte; and (b) a detection reagent or first and second detection reagents that each (i) specifically binds to the unique analyte and (ii) comprises a first detectable label; and wherein the second kit comprises a signal amplification reagent that specifically binds to the first detectable label. In embodiments, the first detectable label is an ECL label. In embodiments, the first and/or the second kit further comprises a surface. In embodiments, the set of kits further comprises a third kit comprising a surface. Components of the kits are further described herein.

In embodiments, the invention provides a set of kits comprising a plurality of first kits and a second kit, wherein each first kit is for detecting a unique analyte of interest, and wherein each first kit comprises: (a) a capture reagent that specifically binds to a unique analyte; (b) a detection reagent that (i) specifically binds to the unique analyte and (ii) comprises a first nucleic acid probe; and (c) a first labeled probe comprising a first detectable label; and wherein the second kit comprises a signal amplification reagent that specifically binds to the first detectable label. In embodiments, the first detectable label is an ECL label. In embodiments, the first and/or the second kit further comprises a surface. In embodiments, the set of kits further comprises a third kit comprising a surface. Components of the kits are further described herein.

In embodiments, the set of kits is capable of detecting multiple analytes of interest in a sample, wherein the analytes are present in concentrations that range from about 0.0001 pg/mL to about 100000 pg/mL. In embodiments, the sample comprises one or more analytes with a concentration that is 10, 100, 1000, 10000, 100000, $10^6$, $10^7$, $10^8$, $10^9$, or $10^{10}$ fold higher than the lowest abundance analytes. In embodiments, each first kit is capable of detecting a higher abundance analyte in the sample. In embodiments, each first kit is not capable of detecting a lower abundance analyte in the sample. In embodiments, a combination of the components of a first kit and a second kit is capable of detecting a lower abundance analyte in a sample. In embodiments, the amount of the higher abundance analyte present in the sample is about 1.5-fold, about 2-fold, about 5-fold, about 10-fold, about 25-fold, about 50-fold, about 75-fold, about 100-fold, about 500-fold, about 1000-fold, about 10000-fold, about 100000-fold, about $10^6$-fold, about $10^7$-fold, about $10^8$-fold, about $10^9$-fold, about $10^{10}$-fold, or greater than $10^{10}$-fold higher than the amount of the lower abundance analyte. In embodiments, the amount of the higher abundance analyte is present in the sample at a concentration of about 1 pg/mL to about 100000 pg/mL and the lower abundance analyte is present in the sample at a concentration of about 0.0001 pg/mL to about 1 pg/mL.

In embodiments, a user performs a method as described herein, comprising detecting one or more analytes of interest using components of the one or more first kits; and, if any of the one or more analytes is substantially undetected, adding the signal amplification reagent of the second kit to provide an amplified assay signal for the one or more substantially undetected analytes.

In embodiments, the invention provides a method comprising: providing to a user a first kit for detecting an analyte of interest in a first sample, wherein the first kit comprises, in one or more vials, containers, or compartments: (a) a capture reagent that specifically binds to the analyte; and (b) a detection reagent or first and second detection reagents that each specifically binds to the analyte; providing to the user a second kit for detecting the analyte in a second sample, wherein the second kit comprises a signal amplification reagent; wherein the first sample comprises a higher amount of the analyte as compared to the second sample. In embodiments, the first and/or the second kit further comprises a surface. In embodiments, the set of kits further comprises a third kit comprising a surface. Components of the kits are further described herein. In embodiments, the invention provides a method comprising providing to a user a second kit for detecting an analyte of interest in a sample, wherein the second kit comprises a signal amplification reagent that specifically binds to a label on a labeled detection reagent or labeled first and second detection reagents, and wherein the second kit is designed for use in conjunction with a first kit that comprises (a) a capture reagent that specifically binds to the analyte; and (b) a labeled detection reagent or labeled first and second detection reagents that each specifically binds to the analyte.

All references cited herein, including patents, patent applications, papers, textbooks and the like, and the references cited therein, to the extent that they are not already, are hereby incorporated herein by reference in their entirety.

EXAMPLES

Example 1. Monoclonal Antibody Development Against ECL Label

Experiments were conducted to develop and screen for antibodies against the MSD SULFO-TAG™ ECL label (MESO SCALE DISCOVERY®, Rockville, MD).

a) Reagent Preparation

Unconjugated MSD GOLD SULFO-TAG™ NHS-Ester (hereinafter referred to as "SULFO-TAG") was separately conjugated to keyhole limpet hemocyanin (KLH) using IMJECT™ EDC mcKLH Spin Kit (Thermo Fisher Scientific, Waltham, MA). The SULFO-TAG was separately conjugated to monomeric bovine serum albumin (BSA) using a typical protein conjugation protocol. KLH-conjugated SULFO-TAG was used as immunogen, and BSA-conjugated SULFO-TAG was used as the screening reagent. A 96-well assay plate containing seven distinct binding domains ("spots") in each well was immobilized with goat-anti-mouse ("GAM") antibody in one of the spots, while the remaining spots were coated with BSA. The plates were used for anti-sera or hybridoma screening.

b) Immunizations

Figure 5:
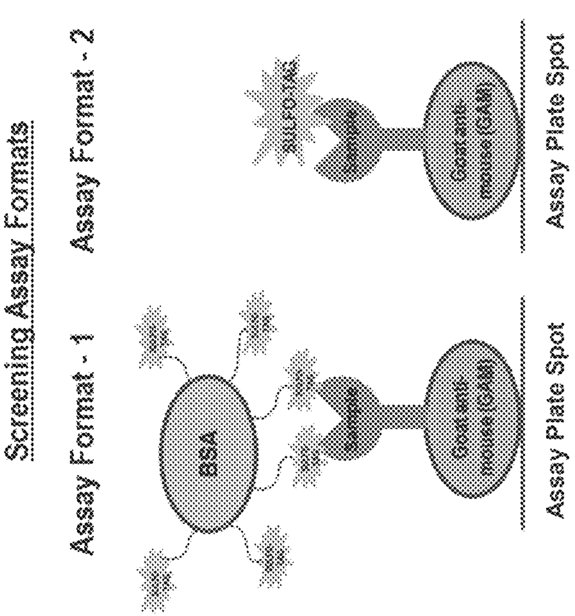
FIG. 5 illustrates an embodiment of methods described herein for screening anti-sera and hybridomas. Goat-anti-mouse (GAM) antibody is immobilized onto a binding domain ("spot") of an assay plate and binds mouse-generated antibodies in a sample. In assay format 1, BSA-conjugated MSD SULFO-TAG™ ECL label ("SULFO-TAG") is used to detect antibodies in the sample that are specific to SULFO-TAG. In assay format 2, unconjugated SULFO-TAG is used to detect antibodies in the sample that are specific to SULFO-TAG.

A group of six 6 to 8 weeks-old female mice (two Balb/C mice, two CFW mice, and two CD-1 mice) were used for immunizations. All mice were injected subcutaneously (SC) and intraperitoneally (IP) with 40 μg of KLH-SULFO-TAG mixed with Complete Freund's Adjuvant on Day 0, and with 20 pg of KLH-SULFO-TAG mixed with Incomplete Freund's Adjuvant on Days 14, 28, 42 and 56. Serum samples collected on Days 36 and 64 were tested for immune response at various dilutions by two different assays. As described above, GAM was immobilized in one of the seven spots in 96-well assay plates, with the remaining spots coated with BSA. After blocking the plates with 1×TBS-T/3% BSA for 30 minutes, various dilutions of anti-sera from the mice were added to the plates and incubated for 1 hour. After washing plates with TBS-T, either BSA-conjugated SULFO-TAG (Assay format 1) or unconjugated SULFO-TAG (Assay format 2) was added to the plates at a concentration of 0.75 μg/ml and then incubated for 1 hour. Plates were then washed and developed using Read Buffer. All incubations were performed at room temperature. Assay formats used for screening are depicted in FIG. 5.

Pre-fusion (final) boosts were performed on Day 77 for mice with the best immune titer by injecting 15 pg of immunogen in the absence of adjuvant. All remaining mice were further boosted on Days 70 and 84 with 20 μg of immunogen mixed with SIGMA ADJUVANT SYSTEM® (MilliporeSigma, St. Louis, MO) and MAGIC™ Mouse Adjuvant (Creative Diagnostics, Shirley, NY). Serum samples collected from these mice on Day 92 were again tested for immune response as described above. Pre-fusion boosts were performed on Day 98 for mice with best antibody titer. Immunizations, serum collection, spleen harvest and animal maintenance were performed at a preclinical contract laboratory in Maryland, US.

Screening data for anti-sera collected on Day 64 (for mice numbers 262 and 265) and Day 92 (for mice numbers 261, 263, 264, and 266) is shown in Table 1. Mice were selected for fusions based on relative ECL signal intensity at 1:37,500 dilution. Out of 6 mice immunized, two Balb/C and two CFW mice showed relatively better immune response and hence selected for fusions. The two CD-1 mice with relatively poor immune response were excluded from the study.

TABLE 1

Sera screening for evaluation of immune response

| | | Serum | Assay format - 1 | | Assay format - 2 | | Mouse selected for |
|---|---|---|---|---|---|---|---|
| Animal ID | Strain | Dilution | GAM | BSA | GAM | BSA | fusion? |
| M05-106-261 | Balb/C | 1:1500 | 42,344 | 77 | 67,602 | 5,418 | Yes |
| | | 1:7500 | 35,772 | 87 | 61,439 | 5,350 | |
| | | 1:37500 | 30,027 | 73 | 48,774 | 5,336 | |
| | | 1:187500 | 18,210 | 86 | 31,180 | 5,491 | |
| M05-106-262 | Balb/C | 1:1500 | 45,756 | 117 | 40,186 | 2,762 | Yes |
| | | 1:7500 | 41,980 | 100 | 37,408 | 2,777 | |
| | | 1:37500 | 27,387 | 129 | 31,248 | 2,678 | |
| | | 1:187500 | 12,499 | 127 | 17,361 | 2,733 | |
| M05-106-263 | CD-1 | 1:1500 | 9,055 | 79 | 23,236 | 5,611 | No |
| | | 1:7500 | 8,109 | 90 | 20,298 | 5,618 | |
| | | 1:37500 | 6,671 | 80 | 19,079 | 5,373 | |
| | | 1:187500 | 4,519 | 75 | 12,370 | 5,516 | |
| M05-106-264 | CD-1 | 1:1500 | 20,778 | 91 | 29,638 | 5,582 | No |
| | | 1:7500 | 17,654 | 78 | 29,891 | 5,572 | |
| | | 1:37500 | 14,587 | 92 | 24,097 | 5,093 | |
| | | 1:187500 | 11,034 | 100 | 16,051 | 5,433 | |
| M05-106-265 | CFW | 1:1500 | 60,114 | 142 | 52,297 | 2,784 | Yes |
| | | 1:7500 | 48,108 | 123 | 44,902 | 2,700 | |
| | | 1:37500 | 33,649 | 137 | 29,564 | 2,622 | |
| | | 1:187500 | 12,623 | 127 | 13,464 | 2,679 | |
| M05-106-266 | CFW | 1:1500 | 71,798 | 76 | 114,809 | 5,355 | Yes |
| | | 1:7500 | 62,955 | 74 | 93,455 | 5,525 | |
| | | 1:37500 | 39,156 | 74 | 74,885 | 5,145 | |
| | | 1:187500 | 19,660 | 99 | 38,633 | 5,293 | |

c) Hybridoma Development

Spleens were collected three days after final boost from mice selected for fusions. Splenocytes were mixed with mouse myeloma cell line P3X63Ag8.653 in 2:1 ratio, and PEG-assisted cell fusions were performed. Post-fusion, cells were seeded in flat-bottom 96-well plates in AH selection medium at a minimum cell density of $20\times10^6$ cells/plate. Hybridoma culture supernatants from all fusion plates were collected 12 days after fusion and tested for antigen specificity by Assay format 1 as described above. All antigen-positive hybridomas were expanded to 48-well plates and re-tested for antigen specificity for further confirmation by the two assay formats described above. These hybridomas were subsequently subcloned by limiting dilution.

From a total of four fusions, 39 plates were screened from which 23 parental hybridoma clones that are specific for SULFO-TAG were identified (Table 2). All antigen-specific clones from fusions F144 and F145 were directly subcloned without performing additional testing at the 48-well stage. Thus, no data was available for these clones in Assay format 2.

As shown in Table 2, although ECL signal intensities varied between two assay formats, no significant differences were observed.

TABLE 2

Hybridoma screening and clone selection at fusion stage

| | | Assay format - 1 | | Assay format - 2 | |
|---|---|---|---|---|---|
| | Clone No. | GAM | BSA | GAM | BSA |
| 1 | F136-1B4 | 50,070 | 109 | 53,298 | 3341 |
| 2 | F136-3A12 | 51,521 | 114 | 55,119 | 3341 |
| 3 | F136-3F10 | 113,694 | 101 | 92,194 | 3292 |
| 4 | F136-5E9 | 78,896 | 108 | 68,946 | 3072 |
| 5 | F136-6F9 | 118,530 | 106 | 96,312 | 3223 |
| 6 | F136-7D11 | 72,914 | 101 | 65,768 | 3386 |
| 7 | F136-7E2 | 49,984 | 109 | 42,597 | 3219 |
| 8 | F136-8E1 | 60,696 | 94 | 50,952 | 3249 |
| 9 | F136-9B7 | 81,463 | 104 | 69,923 | 3166 |
| 10 | F136-10H6 | 68,698 | 98 | 64,043 | 3433 |
| 11 | F137-2F11 | 30,603 | 115 | 97,285 | 3312 |
| 12 | F137-6B9 | 59,177 | 111 | 49,589 | 3288 |
| 13 | F144-2C7 | 28,986 | 74 | | |
| 14 | F144-3C4 | 64,650 | 58 | | |
| 15 | F144-3F4 | 26,587 | 56 | | |
| 16 | F144-4E1 | 18,252 | 46 | | |
| 17 | F144-4G1 | 40,081 | 67 | | |
| 18 | F144-4G7 | 42,006 | 49 | | |
| 19 | F144-5G7 | 18,241 | 79 | | |
| 20 | F144-8B2 | 130,890 | 54 | | |
| 21 | F144-9B2 | 64,554 | 68 | | |
| 22 | F145-10A9 | 18,330 | 58 | | |
| 23 | F145-10H2 | 15,760 | 43 | | |

d) Hybridoma Subcloning and Antibody Purification

Antigen-specific parental hybridomas were subjected to subcloning by limiting dilution in 96-well plates and wells with one, two (indicated by "t" in clone ID) or multiple colonies (indicated by "m") were marked by visual inspection under the microscope. Supernatants from these wells were collected 12 days after seeding and tested for antigen specificity as described above. At least one subclone from each parental line with the best antigen specificity was expanded up to 50 mL in DMEM medium supplemented with ultra-low IgG FBS. Antibody purifications were performed using AMMAG™ Protein A Magnetic Beads from GenScript according to the manufacturer's instructions.

Out of 23 parental hybridomas, 11 clones survived subcloning. Screening data for these clones is shown in Table 3. Consistent with fusion screening results, no significant differences were observed between the two assay formats. A total of 11 purified monoclonal antibodies were generated. Purified anti-SULFO-TAG antibodies are listed in Table 4.

TABLE 3

Hybridoma Screening and Clone Selection at Subclone Stage

| | | Assay format - 1 | | Assay format - 2 | |
|---|---|---|---|---|---|
| | Clone ID | GAM | BSA | GAM | BSA |
| 1 | F136-1B4-8 | 76,376 | 84 | 50,071 | 1,318 |
| 2 | F136-3A12-2 | 75,034 | 121 | 52,344 | 1,511 |
| 3 | F136-3F10-6 | 165,381 | 145 | 117,152 | 1,800 |
| 4 | F136-5E9-2t | 98,044 | 87 | 84,482 | 1,510 |
| 5 | F136-6F9-3 | 129,696 | 88 | 99,565 | 1,397 |
| 6 | F136-7D11-4m | 91,923 | 90 | 55,193 | 1,529 |
| 7 | F136-8E1-1 | 68,167 | 93 | 60,101 | 1,521 |
| 8 | F137-6B9-1 | 33,100 | 85 | 27,858 | 1,488 |

TABLE 3-continued

Hybridoma Screening and Clone Selection at Subclone Stage

| | | Assay format - 1 | | Assay format - 2 | |
|---|---|---|---|---|---|
| | Clone ID | GAM | BSA | GAM | BSA |
| 9 | F144-4G7-3 | 46,464 | 150 | 72,481 | 96,603 |
| 10 | F144-8B2-2 | 145,460 | 145 | 172,353 | 96,246 |
| 11 | F145-10A9-1m | 26,632 | 147 | 91,949 | 93,168 |

TABLE 4

Eleven Anti-SULFO TAG Antibodies

| Antibody clone name | Concentration (mg/mL) | Volume of Antibody Produced (ml) | Amount of Antibody Produced (mg) | Isotype |
|---|---|---|---|---|
| F136-1B4-8 | 1.4 | 2.0 | 2.72 | IgG2b |
| F136-3A12-2 | 1.9 | 2.0 | 3.71 | IgG1 |
| F136-3F10-6 | 1.0 | 2.0 | 1.94 | IgG3 |
| F136-5E9-2t | 0.8 | 2.0 | 1.59 | IgG1 |
| F136-6F9-3 | 1.8 | 2.0 | 3.57 | IgG3 |
| F136-7D11-4m | 1.7 | 2.0 | 3.39 | IgG3 |
| F136-8E1-1 | 1.7 | 2.0 | 3.46 | IgG1 |
| F137-6B9-1 | 1.2 | 0.4 | 0.46 | IgG2b |
| F144-4G7-3 | 1.4 | 2.0 | 2.75 | IgG1 |
| F144-8B2-2 | 2.0 | 2.0 | 3.98 | IgG1 |
| F145-10A9-1m | 1.2 | 0.3 | 0.37 | IgG2b |

The specific germline genes that generated the antibodies were identified. The light chains were produced by the IGLV1*01 F gene, and the heavy chain was produced by the IGHV2-9*02 F gene.

Example 2. Conjugation of Antibodies to Nucleic Acid Probe

Each anti-SULFO-TAG antibody generated in Example 1 was conjugated to a nucleic acid probe, as described in embodiments herein. For nucleic acid probe conjugation, antibodies above 1 mg/mL concentration were diluted to 1 mg/mL in PBS, and antibodies below 1 mg/mL concentration were not concentration adjusted. The buffer for all antibodies was brought to 1 mM EDTA using a 0.5 M EDTA stock solution. Next, each antibody was incubated with a 5-molar excess of a PEGylated SMCC crosslinker, SM(PEG)4, for 1 hour at room temperature. Then, the nucleic acid probe was added in 8-fold molar excess and incubated for 1 hour at room temperature. All conjugation reactions were quenched with a final concentration of 1 mM iodoacetamide and incubated at room temperature for 30 minutes.

Example 3. Antibody Screening

Experiment 1

Anti-SULFO-TAG antibodies conjugated with nucleic acid probe, as described in Example 2, were screened for performance as a signal amplification reagent as described in embodiments herein. Feasibility testing was performed in 96-well streptavidin-coated assay plates with capture and detection antibodies against human ZnT8, human IA-2, human TGM-2, and mouse IL-1b. Assays to detect the concentration of a single analyte were performed as follows:

1) Coat 96-well streptavidin-coated assay plates with 50 μL of biotinylated capture antibody at 0.25 μg/mL and 0.2 ng/mL biotinylated anchoring reagent in coating solution/diluent mixture. Shake at 705 rpm for 1 hour at room temperature.

2) Wash the plate three times, each time with 300 μL of wash buffer.

3) Add 25 μL of blocking solution and 25 μL of calibrator or sample in diluent. Shake at 705 rpm for 1.5 hours at room temperature.

4) Wash the plate three times, each time with 300 μL of wash buffer.

5) Add 50 μL of detection antibody containing SULFO-TAG ("SULFO-TAG-detection antibody") at 1 μg/mL in diluent. Shake at 705 rpm for 1 hour at room temperature.

6) Wash the plate three times, each time with 300 μL of wash buffer.

7) Add 50 μL of anti-SULFO-TAG antibody at 0.125 μg/mL in diluent. Shake at 705 rpm for 1 hour at room temperature.

8) Wash the plate three times, each time with 300 μL of wash buffer.

9) Add 50 μL of enhancement solution containing components for extending the nucleic acid probe of the anti-SULFO-TAG antibody to form an extended sequence.

10) Wash the plate three times, each time with 300 μL of wash buffer.

11) Add 50 μL of detection solution containing components for detecting the extended sequence.

12) Wash the plate three times, each time with 300 μL of wash buffer.

13) Add 150 μL of read buffer.

14) Read plate on plate reader.

Results of the ECL assay signals are shown in FIG. 6. Based on the measured ECL assay signals, anti-SULFO-TAG antibody clones F136-1B4-8, F136-3F10-6, F136-6F9-3, F136-7D11-4m, F136-8E1-1, and F137-6B9-1 were selected for calibrator titration in subsequent experiments.

Experiment 2

Anti-SULFO-TAG antibody clones F136-1B4-8, F136-3F10-6, F136-6F9-3, F136-7D11-4m, F136-8E1-1, and F137-6B9-1 were tested for performance as signal amplification reagents in a calibrator titration immunoassay with biotinylated capture antibody and SULFO-TAG-detection antibodies against human ZnT8 and TGM-2 in immunoassays. Experimental protocol was as outlined in Experiment 1. The antibodies used in the human ZnT8 assay were biotinylated anti-human ZnT8 capture antibody clone number F67-7C2-8 and anti-human ZnT8 SULFO-TAG-detection antibody clone number F67-1A7-6. The antibodies used in the human TGM-2 assay were biotinylated anti-human TGM-2 capture antibody clone number F74-6A5-6 and anti-human TGM-2 SULFO-TAG-detection antibody clone number F69-5E8-3t.

The results of the ECL assay signals, coefficient of variation (CV), Hill slope, R squared value, lowest limit of detection (LLOD), signal-to-background ratio (S/B) for standard 4 (STD 04), and signal-to-noise ratio (S/N) for STD 04 are shown in FIGS. 7 and 8. S/B and S/N were determined from the value of STD 04/STD 08 (blank). FIG. 9 shows the comparative results from immunoassays performed using the same capture and detection antibodies against ZnT8 and TGM-2 but without the anti-SULFO-TAG antibody.

As demonstrated by the data, the use of anti-SULFO-TAG antibodies provided strong enhancement of the assay signals and >10-fold reduction of LLOD for both assays compared to the assays performed without using anti-SULFO-TAG antibody.

Experiment 3

Anti-SULFO-TAG antibody clones F136-1B4-8, F136-3F10-6, F136-6F9-3, F136-7D11-4m, F136-8E1-1, and F137-6B9-1 were tested for performance as signal amplification reagents in calibrator titration with biotinylated capture antibody and SULFO-TAG-detection antibodies against mouse IL-23 and mouse IL-17C in immunoassays. Experimental protocol was as outlined in Experiment 1. The antibodies used in the mouse IL-23 assay were biotinylated anti-mouse IL-23 capture antibody and SULFO-TAG-anti-mouse IL-23 detection antibody from commercial sources. The antibodies used in the mouse IL-17C assay were biotinylated anti-mouse IL-17C capture antibody and SULFO-TAG-anti-mouse IL-17C detection antibody from commercial sources.

The results of the ECL assay signals, coefficient of variation (CV), Hill slope, R squared value, lowest limit of detection (LLOD), signal-to-background ratio (S/B) for standard 2 (STD 02), and signal-to-noise ratio (S/N) for STD 02 are shown in FIGS. 10 and 11. S/B and S/N were determined from the value of STD 02/STD 04 (blank). FIG. 12 shows the comparative results from immunoassays performed using the same capture and detection antibodies against mouse IL-23 and mouse IL-17C but without the anti-SULFO-TAG antibody.

As demonstrated by the data, the use of anti-SULFO-TAG antibodies provided strong enhancement of the assay signals and 40- to 230-fold reduction of LLOD for mouse IL-23 assay and 4- to 120-fold reduction of LLOD for mouse IL-17C assay compared to the assays performed without using anti-SULFO-TAG antibody.

Experiment 4

Anti-SULFO-TAG antibody clones F136-1B4-8, F136-3F10-6, F136-6F9-3, F136-7D11-4m, F136-8E1-1, and F137-6B9-1 were tested for performance in calibrator titration with biotinylated capture antibody and SULFO-TAG-detection antibodies against human IL-10 in immunoassays. Experimental protocol was as outlined in Experiment 1, except that in step 5), SULFO-TAG-detection antibody was added at 0.5 μg/mL. The antibodies used in the human IL-10 assay were biotinylated anti-human IL-10 capture antibody clone number 2108-A82-8 and SULFO-TAG anti-human IL-10 detection antibody clone number 1299-A06-5.

The results of the ECL assay signals, coefficient of variation (CV), Hill slope, R squared value, lowest limit of detection (LLOD), signal-to-background ratio (S/B) for standard 2 (STD 02), and signal-to-noise ratio (S/N) for STD 02 are shown in FIG. 13. S/B and S/N were determined from the value of STD 02/STD 04 (blank). FIG. 14 shows the comparative results from immunoassays performed using the same capture and detection antibodies against human IL-10 but without the anti-SULFO-TAG antibody.

As demonstrated by the data, the use of anti-SULFO-TAG antibodies provided strong enhancement of the assay signals and 50- to 140-fold reduction of LLOD for human IL-10 assay compared to the assays performed without using anti-SULFO-TAG antibody.

Example 4. Signal Inhibition and Enhancement by Anti-SULFO-TAG Antibody

A multiplexed sandwich assay panel was used to assess the signal inhibition and signal enhancement of the eleven anti-SULFO-TAG antibody (also referred to herein as "a-STAG Ab") clones shown in FIG. 6, which were identified from the screen of Example 3. The assay panel, which utilizes a detection antibody mixture containing SULFO-TAG labeled detection antibodies for each of the analytes in the panel, was performed using the provided calibrator blend for the assay. The calibrator blend was prepared by diluting reconstituted lyophilized calibrator approximately 2.43-fold to provide approximately 100 pg/mL of IL-4, one of the analytes in the panel. A standard sandwich assay protocol was performed, summarized briefly as follows:

1) wash the assay panel plate with wash buffer;
2) add calibrator to each well of the plate;
3) wash the assay panel plate with wash buffer;
4) add the detection antibody mixture to form a sandwich complex with the capture antibody, analyte, and SULFO-TAG-labeled detection antibody ("cAb-Analyte-dAb") in each well;
5) wash the assay panel plate with wash buffer.

After formation of the sandwich complexes, the plate was divided into three sections: Standard Signal; Signal Inhibition; and Signal Enhancement. The subsequent components added to the wells of each section are summarized as follows:

| Protocol Step | Standard Signal | Signal Inhibition | Signal Enhancement |
|---|---|---|---|
| 6 | add diluent | add anti-SULFO-TAG antibody with oligonucleotide binding moiety (1 μg/mL) | add anti-SULFO-TAG antibody with oligonucleotide binding moiety (1 μg/mL) |
| 7 | add diluent | add diluent | add SULFO-TAG-labeled oligonucleotide complementary to the binding moiety (50 nM) |

Thus, the Standard Signal section did not have any anti-SULFO-TAG antibody added to the sandwich complexes. The Signal Inhibition section had a cAb-Analyte-dAb complex bound to an anti-SULFO-TAG antibody. The Signal Enhancement section had a cAb-Analyte-dAb complex bound to an anti-SULFO-TAG antibody, and the SULFO-TAG-labeled oligonucleotide bound to the nucleic acid probe of the anti-SULFO-TAG antibody. For the Signal Inhibition and Signal Enhancement sections, each of the eleven anti-SULFO-TAG antibody clones was tested. The assay was performed with nine replicates.

The assay panel plate was incubated at room temperature for 1 hour with shaking at 705 rpm for each of steps 6 and 7 and washed with wash buffer after incubation. Incubation of the Standard Signal and Signal Inhibition conditions with diluent for one or both of steps 6 and 7 ensured that the signal measured in all three sections were equivalent with respect to antibody off rate in the diluent over all incubation steps. ECL read buffer was added to the plate, and the plate was read on an imager.

The results are shown in FIGS. 16A-16C. FIG. 16A shows the percent (%) signal inhibition and % signal increase for each of the anti-SULFO-TAG antibody clones. FIGS. 16B and 16C show bar graph plots of the % signal inhibition and % signal increase, respectively. Percent (%) signal inhibition was calculated as 1−(Signal Inhibition/Standard Signal). Linear percent (%) signal increase was calculated as (Signal Enhancement−Signal Inhibition)/[MAX of (Signal Enhancement−Signal Inhibition) across all eleven anti-SULFO-TAG antibodies]. The ratio % signal increase can be calculated as (Signal Enhancement/Standard Signal)−1. The ratio of signal with or without SULFO-TAG-labeled oligo can be calculated as (Signal Enhancement/Signal Inhibition).

As shown in FIGS. 16A-16C, anti-SULFO-TAG antibody clones F136-1B4-8, F136-3F10-6, and F136-6F9-3 had the highest % signal inhibition and highest % signal increase, demonstrating specificity to the SULFO-TAG label. Affinity of each of the anti-SULFO-TAG antibody clones was calculated, as shown in Table 5.

TABLE 5

% Signal Increase with Anti-SULFO-TAG Antibody Clones

| Antibody clone name | % Signal Increase |
|---|---|
| F136-1B4-8 | 71% |
| F136-3A12-2 | 20% |
| F136-3F10-6 | 87% |
| F136-5E9-2t | 27% |
| F136-6F9-3 | 100% |
| F136-7D11-4m | 21% |
| F136-8E1-1 | 39% |
| F137-6B9-1 | 12% |
| F144-4G7-3 | 11% |
| F144-8B2-2 | 22% |
| F145-10A9-1m | 10% |

Example 5. Anti-SULFO-TAG Antibody Epitope Recognition Study

An epitope recognition study was performed on the eleven anti-SULFO-TAG antibody clones described in Example 4. To study the epitope recognition of these antibody clones, four organometallic $Ru^{2+}$ compounds ("TAG compounds") with varying numbers of sulfomethyl-bipyridine ("SM") or bipyridine ("Bpy") ligands as shown in FIG. 18A were prepared. The SULFO-TAG is denoted as $Ru^{+2}(SM)_2A1$, which includes an acid ligand ("A") in one of the Bpy groups and is more similar in structure with Bpy than SM. ECL generation from each TAG compound was verified by spiking the TAG compounds into ECL read buffer, and the ECL signal from each free TAG compound was measured on 96-well bare carbon plates. The results are shown in FIG. 18B and indicate that all TAG compounds produce roughly equal ECL signals when normalized to concentration of the TAG compound, demonstrating that modification of the bipyridine ligand has minimal effect on ECL generation efficiency. The $Ru(Bpy)_3$ ECL signal, when normalized for concentration, would be 248,576 ECL units, similar to the other TAG compounds.

To study the anti-SULFO-TAG antibody specificity and affinity for the TAG compounds, the antibodies were coated on MSD® 96-well Small Spot Streptavidin plates, then exposed to varying concentrations of the four TAG compounds. ECL signal from the anti-SULFO-TAG antibodies were measured as described in Example 4, with higher signal indicative of stronger binding affinity. The results are shown in FIGS. 19A-19G. The results show that the anti-SULFO-TAG antibody clones can be grouped according to their affinity for TAG compounds with different ligands. Four antibodies (clone numbers 1, 3, 5, and 7) had <1 nM affinity ($K_D$) for SULFO-TAG, while the remaining antibodies had $K_D$>20 nM, with some possibly in the micromolar range. For $Ru^{+2}(SM)_3$, which has three SM ligands, the same affinity pattern was observed. For $Ru^{+2}(Bpy)_2(SM)$, which only has one SM ligand and two Bpy ligands, antibody clones 1, 3, and 5 retained a relatively high affinity, but antibody clone 7 had significantly reduced affinity of <100 nM. Further replacement of the remaining SM ligand with Bpy, $Ru^{+2}(Bpy)_3$, nearly eliminated recognition by all antibody clones. These results demonstrate that the SM ligand is at least partly responsible for strong binding to antibody clones 1, 3, 5, and 7. Uniquely, antibody clone 7 required two SM ligands for recognition.

To further verify the role of ligands in antibody recognition, the antibodies were coated on MSD® 96-well Small Spot Streptavidin plates and first exposed to 2 μM of ligands SM, Bpy, or A, then exposed to different concentrations of the TAG compounds as a competition assay. The competition assay results are shown in FIGS. 20A-20I. The results show that the SM ligand on the TAG compounds is a key epitope for strong binding in antibody clones 1, 3, 5, and 7. Of these four antibody clones, clones 1, 3, and 5 required only one SM ligand in the TAG compound for strong binding, but clone 7 required two SM ligands for strong binding. All antibody clones did not recognize TAG compounds with three Bpy ligands. The ligand competition studies further demonstrated that the SM ligand, which had the strongest binding, is the dominant ligand recognized by the antibodies, while the Bpy and A ligands were unable to significantly outcompete antibody binding to the $Ru^{+2}(SM)_3$ and SULFO-TAG compounds.

Example 6. Further Epitope Recognition Studies

A further epitope recognition study is performed to determine whether the sulfonate functional groups on the SM ligand are required for antibody recognition, and whether addition of different charged functionality to the methylene groups alters antibody recognition. Organometallic $Ru^{2+}$ compounds for this study are shown in FIG. 21.

What is claimed is:

1. A method of detecting an analyte of interest in a sample, comprising:

(I):

a. contacting a first complex that comprises (A) a first detectable label, wherein the first detectable label is an electrochemiluminescent (ECL) label, and (B) the analyte of interest, with a signal amplification reagent that specifically binds to the first detectable label, wherein the signal amplification reagent comprises a nucleic acid probe, thereby forming a second complex comprising the first complex and the signal amplification reagent;

b. extending the nucleic acid probe to form an extended sequence; and c. measuring the amount of extended sequence, thereby detecting the analyte of interest;

or (II):

d. forming a first complex on a surface comprising the analyte of interest, a capture reagent that specifically binds to the analyte, wherein the capture reagent is immobilized on the surface or wherein the capture reagent is capable of being immobilized to the surface; and a detection reagent that specifically binds to the analyte and that comprises a first nucleic acid probe;

e. extending the first nucleic acid probe to form a first extended sequence comprising a first anchoring region, wherein the first anchoring region binds a first anchoring reagent that is immobilized on the surface;

f. binding the first extended sequence to a first labeled probe comprising a first detectable label, wherein the first detectable label is an electrochemiluminescent (ECL) label;

g. contacting the first labeled probe bound to the first extended sequence with a signal amplification reagent that specifically binds to the first detectable label, wherein the signal amplification reagent comprises a second nucleic acid probe, thereby forming a second complex comprising the signal amplification reagent and the first labeled probe;

h. extending the second nucleic acid probe to form a second extended sequence comprising a second anchoring region, wherein the second anchoring region binds a second anchoring reagent that is immobilized on the surface; and;

i. measuring the amount of (I) the second extended sequence or (II) the first extended sequence and the second extended sequence bound to the surface, thereby detecting the analyte of interest.

2. The method of claim 1, wherein the first complex of (I) is on a surface, optionally wherein the surface comprises a particle or a well of a multi-well plate.

3. The method of claim 2, wherein the first complex of (I) comprises:

a capture reagent that specifically binds to the analyte, wherein the capture reagent is immobilized on the surface prior to the contacting of (a); and a detection reagent that specifically binds to the analyte and that comprises the first detectable label.

4. The method of claim 3, wherein the capture reagent, the detection reagent, and the signal amplification reagent each comprises an antibody or antigen-binding fragment thereof, antigen, ligand, receptor, oligonucleotide, hapten, epitope, mimotope, or aptamer.

5. The method of claim 3, wherein the first detectable label is linked to the detection reagent via a conjugation linker.

6. The method of claim 2, wherein the first complex of (I) comprises:

a capture reagent that specifically binds to the analyte, wherein the capture reagent is immobilized on the surface prior to the contacting of (a);

a first detection reagent that specifically binds to the analyte; and a second detection reagent that specifically binds to the analyte, wherein the first complex comprises at least two first detectable labels, and wherein each of the first detection reagent and the second detection reagent comprises one of the at least two first detectable labels.

7. The method of claim 6, wherein the first detectable label is linked to the second detection reagent via a conjugation linker, and wherein the signal amplification reagent is capable of binding simultaneously to the first detectable label on the first detection reagent and to the first detectable label on the second detection reagent.

8. The method of claim 2, wherein the surface comprises an electrode, and the measuring further comprises applying a voltage waveform to the electrode to generate an electrochemiluminescence signal; or wherein the surface comprises a particle, and the method further comprises collecting the particle on an electrode, and the measuring further comprises applying a voltage waveform to the electrode to generate an electrochemiluminescence signal.

9. The method of claim 1, wherein the extending of (b), (e), or (h) comprises polymerase chain reaction (PCR), ligase chain reaction (LCR), strand displacement amplification (SDA), self-sustained synthetic reaction (3SR), isothermal amplification, or combination thereof; and when the extending of (b), (e), or (h) comprises PCR, the extending comprises binding the nucleic acid probe to a template oligonucleotide and extending the nucleic acid probe by PCR;

when the extending of (b), (e), or (h) comprises isothermal amplification, the extending comprises binding the nucleic acid probe to a template oligonucleotide, forming a circular template, and extending the nucleic acid probe by rolling circle amplification (RCA).

10. The method of claim 9, wherein the first complex of (I) is on a surface, and wherein the surface comprises an anchoring reagent that is immobilized on the surface prior to or during the extending of (b), wherein the anchoring reagent binds to an anchoring region of the extended sequence.

11. The method of claim 10, wherein the anchoring reagent and the anchoring region comprise complementary oligonucleotides, and wherein the measuring of (c) comprises measuring the amount of extended sequence bound to the surface via the anchoring reagent.

12. The method of claim 1, wherein the first complex of (I) comprises at least two first detectable labels;

wherein the signal amplification reagent is a first signal amplification reagent, and the contacting of (a) further comprises contacting the first complex with a second signal amplification reagent that comprises a nucleic acid probe, wherein the first and second signal amplification reagents each binds to a distinct first detectable label, and the second complex comprises the first complex and the first and second signal amplification reagents.

13. The method of claim 12, wherein the extending of (b) comprises:

binding one or both of the nucleic acid probes of the first and second signal amplification reagents to a template oligonucleotide, forming a circular template, and extending one or both nucleic acid probes by RCA, wherein:

each nucleic acid probe is bound to a distinct template oligonucleotide; a circular template is formed from each template oligonucleotide; and each nucleic acid probe is extended by RCA; or both nucleic acid probes are contacted with two template oligonucleotides, wherein each template oligonucleotide binds to a portion of each nucleic acid probe; the two template oligonucleotides are ligated to form a circular template; and one or both of the nucleic acid probes are extended by RCA.

14. The method of claim 13, wherein the nucleic acid probes of the first and second signal amplification reagents comprise or consist of a same sequence.

15. The method of claim 1, wherein the method further comprises, prior to the contacting of (a) or (g) detecting the first complex, wherein detecting the first complex comprises measuring the amount of the first detectable label.

16. The method of claim 1, wherein the signal amplification reagent is an antibody or antigen-binding fragment thereof comprising an antigen binding domain specific to an electrochemiluminescent (ECL) label or to an ECL label and a conjugation linker.

17. The method of claim 1, wherein the measuring comprises binding the extended sequence of (I) to a labeled probe or binding the second extended sequence of (II) to a second labeled probe, wherein the labeled probe or the second labeled probe comprises a second detectable label, and measuring the amount of (i) the second detectable label or (ii) the first and second detectable labels on the surface.

18. The method of claim 17, wherein the second detectable label is capable of being measured using light scattering, optical absorbance, fluorescence, chemiluminescence, electrochemiluminescence, bioluminescence, phosphorescence, radioactivity, magnetic field, or combinations thereof.

19. The method of claim 18, wherein each of the first detectable label and the second detectable label is an ECL label, and wherein the ECL label of the first and/or the second detectable label comprises an organometallic complex comprising at least one substituted bipyridine ligand, wherein the substituted bipyridine ligand comprises at least one sulfonate group, and optionally wherein:

the organometallic complex comprises at least two substituted bipyridine ligands, wherein each substituted bipyridine ligand comprises at least one sulfonate group;

the organometallic complex comprises ruthenium, osmium, or rhenium; and/or the substituted bipyridine ligand is a compound of Formula I:

(I)

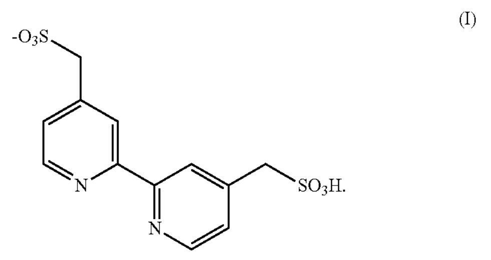

20. The method of claim 18, wherein each of the first detectable label and the second detectable label is an ECL label, and wherein the ECL label of the first and the second detectable label is a compound of Formula II:

(II)

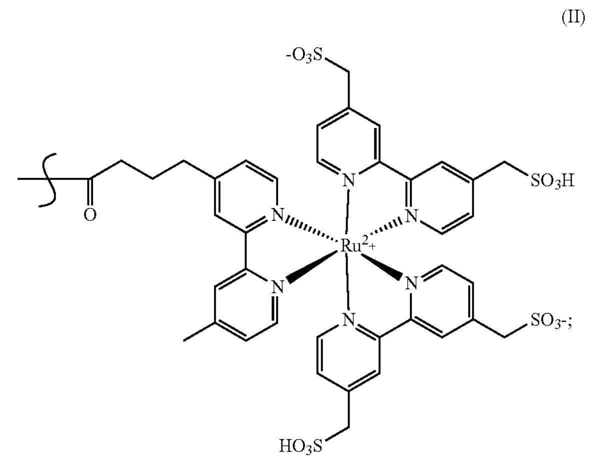

or wherein the first detectable label comprises a compound of Formula II, and the second detectable label comprises a compound of any one of Formulas III, IV, V, or VI:

(III)

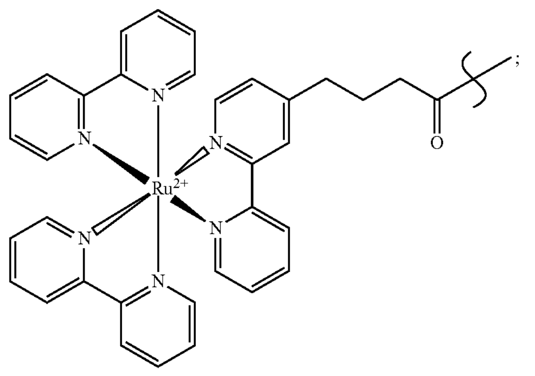

(VI)

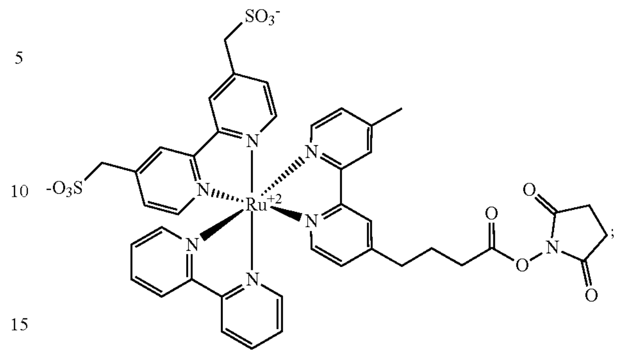

(IV)

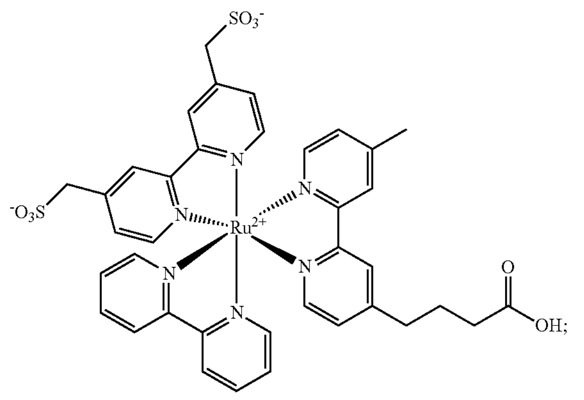

(V)

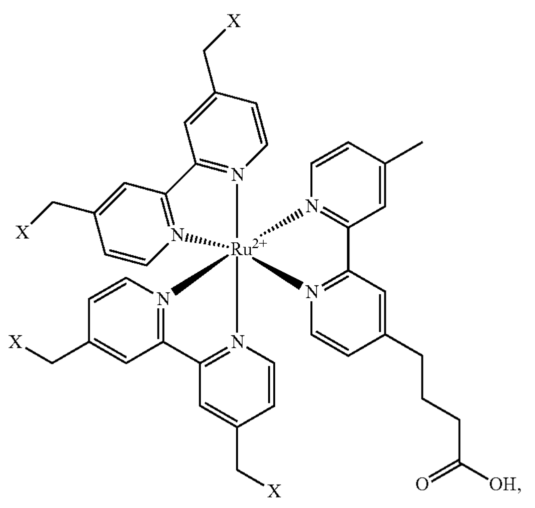

wherein X is a phosphate, a carbonate, a borate, or combination thereof;

or wherein the first detectable label comprises a compound of Formula III, and the second detectable label comprises a compound of any one of Formulas II, IV, V, or VI; or wherein the first detectable label comprises a compound of Formula IV, and the second detectable label comprises a compound of any one of Formulas II, III, V, or VI; or wherein the first detectable label comprises a compound of Formula V, and the second detectable label comprises a compound of any one of Formulas II, III, IV, or VI; or wherein the first detectable label comprises a compound of Formula VI, and the second detectable label comprises a compound of any one of Formulas II, III, IV, or V.

21. The method of claim 1, wherein the surface of (II) comprises an electrode, and the measuring further comprises applying a voltage waveform to the electrode to generate an electrochemiluminescence signal; or wherein the surface of (II) comprises a particle, and the method further comprises collecting the particle on an electrode, and the measuring further comprises applying a voltage waveform to the electrode to generate an electrochemiluminescence signal.

22. The method of claim 1, wherein, in the first complex of (II), the capture reagent, the detection reagent, and the signal amplification reagent each comprises an antibody or antigen-binding fragment thereof, antigen, ligand, receptor, oligonucleotide, hapten, epitope, mimotope, or aptamer.

23. The method of claim 1, wherein the first extended sequence of (II) binds to at least two first labeled probes that each comprise a first detectable label;

wherein the signal amplification reagent of (II) is a first signal amplification reagent, and the contacting of (g) further comprises contacting the first extended sequence with a second signal amplification reagent that comprises a third nucleic acid probe, wherein the first and second signal amplification reagents each binds to a distinct first detectable label, and the second complex comprises the first and second signal amplification reagents each bound to a first labeled probe.

24. The method of claim 23, wherein the extending of (h) comprises:

binding one or both of the second and third nucleic acid probes of the first and second signal amplification reagents to a template oligonucleotide, forming a circular template, and extending one or both second nucleic acid probes by RCA, wherein:

each second nucleic acid probe is bound to a distinct template oligonucleotide; a circular template is formed from each template oligonucleotide; and each second nucleic acid probe is extended by RCA; or both second nucleic acid probes are contacted with two template oligonucleotides, wherein each template oligonucleotide binds to a portion of each second nucleic acid probe; the two template oligonucleotides are ligated to form a circular template; and one or both of the second nucleic acid probes are extended by RCA.

* * * * *